(12) United States Patent  
Shinohata et al.

(10) Patent No.: US 8,053,595 B2  
(45) Date of Patent: Nov. 8, 2011

(54) PROCESS FOR PRODUCING ISOCYANATES

(75) Inventors: Masaaki Shinohata, Tokyo (JP);  
Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 36 days.

(21) Appl. No.: 12/514,737

(22) PCT Filed: Nov. 16, 2007

(86) PCT No.: PCT/JP2007/072268  
§ 371 (c)(1),  
(2), (4) Date: May 13, 2009

(87) PCT Pub. No.: WO2008/059953  
PCT Pub. Date: May 22, 2008

(65) Prior Publication Data  
US 2010/0029981 A1  Feb. 4, 2010

(30) Foreign Application Priority Data

| Nov. 17, 2006 | (JP) | 2006-311048 |
| Nov. 17, 2006 | (JP) | 2006-311049 |
| Nov. 17, 2006 | (JP) | 2006-311054 |
| Nov. 17, 2006 | (JP) | 2006-311057 |
| Mar. 30, 2007 | (JP) | 2007-091382 |
| Mar. 30, 2007 | (JP) | 2007-091403 |

(51) Int. Cl.  
*C07C 263/00* (2006.01)

(52) U.S. Cl. .................................................. 560/345

(58) Field of Classification Search .................. None  
See application file for complete search history.

(56) References Cited

U.S. PATENT DOCUMENTS

| 2,692,275 A | 10/1954 | Bortnick |
| 3,125,598 A | 3/1964 | Kühle et al. |
| 3,734,941 A | 5/1973 | Sydor |
| 3,992,430 A | 11/1976 | Bacskai |
| 4,081,472 A | 3/1978 | Tsumura et al. |
| 4,097,676 A | 6/1978 | Romano |
| 4,123,450 A | 10/1978 | Weber, Jr. .................. 260/453 P |
| 4,290,970 A | 9/1981 | Merger et al. |
| 4,354,979 A * | 10/1982 | Schwendemann et al. ... 560/344 |
| 4,386,033 A | 5/1983 | Konig et al. |
| 4,388,238 A | 6/1983 | Heitkamper et al. |
| 4,388,246 A | 6/1983 | Sundermann et al. |
| 4,388,426 A | 6/1983 | Schure et al. |
| 4,430,505 A | 2/1984 | Heitkamper et al. |
| 4,480,110 A | 10/1984 | Heitkamper et al. |
| 4,482,499 A | 11/1984 | Merger et al. |
| 4,497,963 A | 2/1985 | Merger et al. |
| 4,596,678 A | 6/1986 | Merger et al. |
| 4,596,679 A | 6/1986 | Hellbach et al. |
| 4,613,466 A | 9/1986 | Merger et al. |
| 4,659,845 A | 4/1987 | Rivetti et al. |
| 4,692,550 A | 9/1987 | Engbert et al. |
| 4,925,971 A | 5/1990 | Aoki et al. |
| 5,087,739 A | 2/1992 | Bohmholdt et al. |
| 5,315,034 A | 5/1994 | Mizia et al. |
| 5,386,053 A | 1/1995 | Otterbach et al. |
| 5,616,784 A | 4/1997 | Schwarz et al. |
| 5,883,291 A * | 3/1999 | Schleenstein et al. ........ 560/345 |
| 6,143,917 A | 11/2000 | Harada et al. |
| 6,992,214 B2 | 1/2006 | Cesti et al. |
| 7,446,218 B2 | 11/2008 | Miyake et al. |
| 2003/0055282 A1 | 3/2003 | Bosman et al. |
| 2005/0080274 A1 | 4/2005 | Miyake et al. |
| 2007/0055042 A1 | 3/2007 | Miyake et al. |
| 2008/0275262 A1 | 11/2008 | Miyake et al. |

FOREIGN PATENT DOCUMENTS

| CN | 1419538 A | 5/2003 |
| DE | 925 496 | 3/1955 |
| EP | 0 320 235 | 6/1989 |
| EP | 0 355 443 A2 | 2/1990 |
| EP | 0 446 514 A1 | 9/1991 |
| EP | 0 957 073 A1 | 11/1999 |
| EP | 1 640 357 A1 | 3/2006 |
| GB | 1217122 | 12/1970 |
| JP | 46-27593 | 8/1971 |
| JP | 52-71443 | 6/1977 |
| JP | 52-136147 A | 11/1977 |
| JP | 60-231640 A | 11/1985 |

| JP | 61-183257 | | 8/1986 |
| --- | --- | --- | --- |
| JP | 1-230550 | A | 9/1989 |
| JP | 4-026665 | A | 1/1992 |
| JP | 6-25136 | | 2/1994 |
| JP | 06-056984 | | 3/1994 |
| JP | 6-192204 | A | 7/1994 |
| JP | 10-316645 | | 12/1998 |
| JP | 11-5774 | A | 1/1999 |
| JP | 2001-323106 | A | 11/2001 |
| JP | 3238201 | B | 12/2001 |
| JP | 2002-500654 | A | 1/2002 |
| JP | 3382289 | | 12/2002 |
| JP | 2003-055332 | A | 2/2003 |
| JP | 2003-525267 | A | 8/2003 |
| JP | 2004-244349 | A | 9/2004 |
| JP | 2004-262834 | A | 9/2004 |
| JP | 2004-262835 | A | 9/2004 |
| JP | 2006-69941 | | 3/2006 |
| WO | WO95/23484 | A | 8/1995 |
| WO | WO 98/54128 | | 12/1998 |
| WO | WO 03/055840 | A1 | 7/2003 |
| WO | WO 2004/014840 | A1 | 2/2004 |
| WO | WO 2005/000783 | A | 1/2005 |
| WO | WO 2005/111049 | A1 | 11/2005 |

OTHER PUBLICATIONS

STN Accession No. 127:247849 CASREACT structure diagram for Schleenstein et al. US 5883291.* xylenol printout http://en.wikipedia.org/wiki/Xylenol.*
Edited by Kagaku Daijiten Henshu Iinkai, Kagaku Daijiten, 7, reduced-size edition 32nd print, Kyoritsu Shuppan Co., Ltd., Aug. 15, 1989, pp. 725 to 728.
Berchte der Deutechen Chemischen Gesellschaft, vol. 3, p. 653, 1870.
Elizabeth Dyer et al., "Thermal Degradation of Alkyl N-Phenylcarbamates" Journal of the American Chemical Society, vol. 81, p. 2138-2143, 1959.
Kosa, Cs. et al., "New combined phenol-hindered amine stabilizers for polymers based on diphenylmethane-4, 4'-diisocyanate and dicyclohexylmethane-4,4'-diisocyanate", Polymer Degradation and Stability, 86(3), p. 391-400, 2004.
Habicher et al., "Synthesis and Antioxidative Properties of Novel Multifunctional Stabilizers" Journal of Vinyl & Additives Technology, vol. 7, No. 1, pp. 4-18, 2001.
Kovacic et al., "Reactions of t-Butylperoxy Isopropyl Carbonate with Aromatic Compounds under Friedel- Crafts Conditions", Journal of Organic Chemistry, vol. 31, No. 8, pp. 2459-2467, 1966.
Petersen, Siegfried, Polyurethans. V. Low-molecular conversion products of diisocyanates, Ann., 562, pp. 205-229, 1949.
Noboru Yamazaki et al., "The Reaction of Diphenyl Carbonate with Amines and Its Application to Polymer Synthesis", Journal of Polymer Science, Polymer Chemistry Edition, vol. 17, p. 835-841, 1979.
D.S. Tarbell et al., "Acidic and Basic Catalysis in Urethan Formation", Journal of the American Chemical Society, vol. 64(9), p. 2229-2230, 1942.
Leuckart, R., *Ueber Einige Synthesen Mittelst Phenylcyanat*, Journal für Praktische Chemie, vol. 41, pp. 301-329.
Ohme, V. et al., *Synthesen Mit Brenzcatechincarbonat*, Journal für Praktische Chemie, vol. 313, 1971, pp. 626-635.

* cited by examiner

*Primary Examiner* — Daniel Sullivan
*Assistant Examiner* — Jennifer C Sawyer
(74) *Attorney, Agent, or Firm* — Morgan, Lewis & Bockius LLP

(57) ABSTRACT

An object of the present invention is to provide a process that enables isocyanates to be stably produced over a long period of time at high yield without encountering various problems as found in the prior art when producing isocyanates without using phosgene. The present invention discloses a process for producing an isocyanate, comprising the steps of: reacting a carbamic acid ester and an aromatic hydroxy compound to obtain an aryl carbamate having a group derived from the aromatic hydroxy compound; and subjecting the aryl carbamate to a decomposition reaction, wherein the aromatic hydroxy compound is an aromatic hydroxy compound which is represented by the following formula (1) and which has a substituent $R^1$ at least one ortho position of a hydroxyl group:

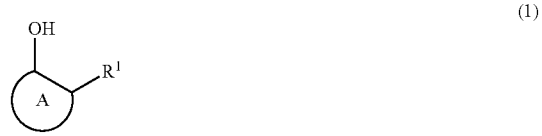

(1)

(wherein ring A represents an aromatic hydrocarbon ring in a form of a single or multiple rings which may have a substitute and which have 6 to 20 carbon atoms;
$R^1$ represents a group other than a hydrogen atom in a form of an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the group containing an atom selected from a carbon atom, an oxygen atom and a nitrogen atom; and $R^1$ may bond with A to form a ring structure).

16 Claims, 7 Drawing Sheets

PROCESS FOR PRODUCING ISOCYANATES

TECHNICAL FIELD

The present invention relates to a process for producing isocyanate.

BACKGROUND ART

Isocyanates are widely used as production raw materials of such products as polyurethane foam, paints and adhesives. The main industrial production process of isocyanates involves reacting amines with phosgene (phosgene method), and nearly the entire amount of isocyanates produced throughout the world are produced according to the phosgene method. However, the phosgene method has numerous problems.

Firstly, this method requires the use of a large amount of phosgene as raw material. Phosgene is extremely toxic and requires special handling precautions to prevent exposure of handlers thereof, and also requires special apparatuses to detoxify waste.

Secondly, since highly corrosive hydrogen chloride is produced in large amounts as a by-product of the phosgene method, in addition to requiring a process for detoxifying the hydrogen chloride, in many cases hydrolytic chlorine is contained in the isocyanates produced, which may have a detrimental effect on the weather resistance and heat resistance of polyurethane products in the case of using isocyanates produced using the phosgene method.

On the basis of this background, a process for producing isocyanates has been sought that does not use phosgene. One example of a method for producing isocyanate compounds without using phosgene that has been proposed involves thermal decomposition of carbamic acid esters. Isocyanates and hydroxy compounds have long been known to be obtained by thermal decomposition of carbamic acid esters (see, for example, Berchte der Deutechen Chemischen Gesellschaft, Vol. 3, p. 653, 1870). The basic reaction is illustrated by the following formula:

(wherein R represents an organic residue having a valence of a, R' represents a monovalent organic residue, and a represents an integer of 1 or more).

The thermal decomposition reaction represented by the above-mentioned formula is reversible, and in contrast to the equilibrium thereof being towards the carbamic acid ester on the left side at low temperatures, the isocyanate and hydroxy compound side becomes predominant at high temperatures. Thus, it is necessary to carry out the carbamic acid ester thermal decomposition reaction at high temperatures. In addition, in the case of alkyl carbamates in particular, since the reaction rate is faster for the reverse reaction of thermal decomposition, namely the reaction by which alkyl carbamate is formed from isocyanate and alcohol, the carbamic acid ester ends up being formed before the isocyanate and alcohol formed by thermal decomposition are separated, thereby frequently leading to an apparent difficulty in the progression of the thermal decomposition reaction.

On the other hand, thermal decomposition of alkyl carbamates is susceptible to the simultaneous occurrence of various irreversible side reactions such as thermal denaturation reactions undesirable for alkyl carbamates or condensation of isocyanates formed by the thermal decomposition. Examples of these side reactions include a reaction in which urea bonds are formed as represented by the following formula (2), a reaction in which carbodiimides are formed as represented by the following formula (3), and a reaction in which isocyanurates are formed as represented by the following formula (4) (see, Berchte der Deutechen Chemischen Gesellschaft, Vol. 3, p. 653, 1870 and Journal of American Chemical Society, Vol. 81, p. 2138, 1959):

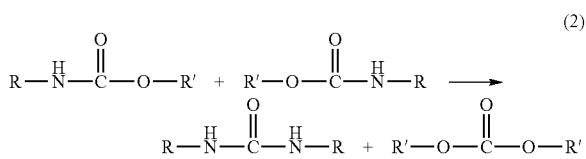

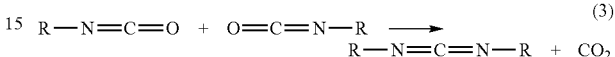

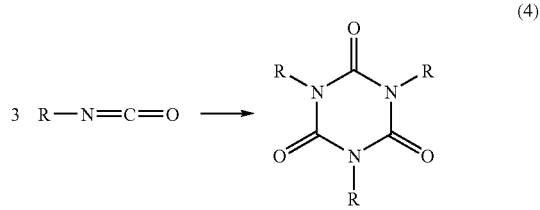

In addition to these side reactions leading to a decrease in yield and selectivity of the target isocyanate, in the production of polyisocyanates in particular, these reactions may make long-term operation difficult as a result of, for example, causing the precipitation of polymeric solids that clog the reaction vessel.

Various methods have been proposed to solve such problems. For example, a method for producing polyisocyanate has been proposed in which an alkyl polycarbamate, in which ester groups are composed of alkoxy groups corresponding to a primary alcohol, is subjected to a transesterification reaction with a secondary alcohol to produce an alkyl polycarbamate in which the ester groups are composed of alkoxy groups corresponding to the secondary alcohol, followed by thermal decomposition of the alkyl polycarbamate (see, for example, International Publication No. WO 95/23484). It is described in this method that the thermal decomposition temperature of the alkyl polycarbamate can be set to a lower temperature by going through an alkyl polycarbamate in which the ester groups are composed of alkoxy groups corresponding to the secondary alcohol, thereby resulting in the effect of being able to inhibit precipitation of polymeric solid. However, the reverse reaction rate between the polyisocyanate formed by the thermal decomposition reaction of the alkyl polycarbamate and the secondary alcohol is still fast, thereby leaving the problem of inhibiting the formation of alkyl polycarbamate by the reverse reaction unsolved.

An alternative method has been disclosed whereby, in the production of aromatic isocyanates, for example, an aromatic alkyl polycarbamate and an aromatic hydroxy compound are subjected to a transesterification reaction to produce an aromatic aryl polycarbamate followed by thermal decomposition of the aromatic aryl polycarbamate to product an aromatic isocyanate (see, for example, U.S. Pat. No. 3,992,430). This method describes the effect of being able to set the thermal decomposition temperature to a lower temperature by going through an aromatic aryl polycarbamate. However, in the case of this aromatic aryl polycarbamate as well, under temperatures like those at which the transesterification reaction or thermal decomposition reaction is carried out, there are many cases in which side reactions like those described above still occur, there leaving the problem of improving isocyanate yield unsolved. Moreover, thermal decomposition of N-substituted aromatic urethanes in the gaseous phase or liquid phase is known to frequently result in the occurrence of various undesirable side reactions (see, for example, U.S. Pat. No. 4,613,466).

DISCLOSURE OF INVENTION

Problems to be Solved by the Invention

As has been described above, there are currently hardly any methods for industrially producing polyisocyanates at favorable yield without using extremely toxic phosgene.

An object of the present invention is to provide a process that enables isocyanates to be stably produced over a long period of time at high yield without encountering various problems as found in the prior art when producing isocyanates without using phosgene.

Means for Solving the Problems

In view of the above, as a result of conductive extensive studies on the above-mentioned problems, the inventors of the present invention found that a production process in which a carbamic acid ester and a specific aromatic hydroxy compound are subjected to a transesterification reaction to produce an aryl carbamate followed by subjecting the aryl carbamate to a thermal decomposition reaction to produce isocyanate enables the above-mentioned problems to be solved, thereby leading to completion of the present invention.

Namely, the present invention provides the followings:

[1] a process for producing an isocyanate, comprising the steps of:

reacting a carbamic acid ester and an aromatic hydroxy compound to obtain an aryl carbamate having a group derived from the aromatic hydroxy compound; and subjecting the aryl carbamate to a decomposition reaction, wherein the aromatic hydroxy compound is an aromatic hydroxy compound which is represented by the following formula (5) and which has a substituent $R^1$ at least one ortho position of a hydroxyl group:

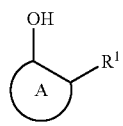
(5)

(wherein ring A represents an aromatic hydrocarbon ring in a form of a single or multiple rings which may have a substituent and which have 6 to 20 carbon atoms;

$R^1$ represents a group other than a hydrogen atom in a form of an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the group containing an atom selected from a carbon atom, an oxygen atom and a nitrogen atom; and $R^1$ may bond with A to form a ring structure),

[2] the process according to item [1], wherein the aromatic hydroxy compound is a compound represented by the following formula (6):

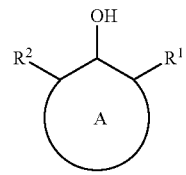
(6)

(wherein ring A and $R^1$ are the same as defined above, $R^2$ represents a hydrogen atom or an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or aralkyloxy group having 7 to 20 atoms, the aliphatic alkyl, the aliphatic alkoxy, the aryl, the aryloxy, the aralkyl and the aralkyloxy groups containing an atom selected from a carbon atom, an oxygen atom and a nitrogen atom, and $R^2$ may bond with A to form a ring structure),

[3] the process according to item [2], wherein in the formula (6), a total number of the carbon atoms constituting $R^1$ and $R^2$ is 2 to 20,

[4] the process according to any one of items [1] to [3], wherein the ring A of the aromatic hydroxy compound comprises a structure containing at least one structure selected from the group consisting of a benzene ring, a naphthalene ring and an anthracene ring,

[5] the process according to item [4], wherein the aromatic hydroxy compound is a compound represented by the following formula (7):

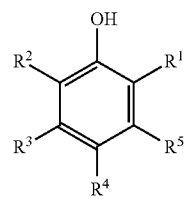
(7)

(wherein $R^1$ and $R^2$ are the same as defined above, and each of $R^3$, $R^4$ and $R^5$ independently represents a hydrogen atom or an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the aliphatic alkyl, the aliphatic alkoxy, the aryl, the aryloxy, the aralkyl and the aralkyloxy groups containing an atom selected from a carbon atom, an oxygen atom and a nitrogen atom),

[6] the process according to item [5], wherein the aromatic hydroxy compound is such that in the formula (7), each of $R^1$ and $R^4$ independently represents a group represented by the following formula (8), and $R^2$, $R^3$ and $R^5$ represent a hydrogen atom:

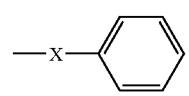
(8)

(wherein X represents a branched structure selected from the structures represented by the following formulas (9) and (10):

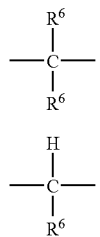
(9)
(10)

(wherein $R^6$ represents a linear or branched alkyl group having 1 to 3 carbon atoms),

[7] the process according to item [5], wherein the aromatic hydroxy compound is such that in the formula (3), $R^1$ represents a linear or branched alkyl group having 1 to 8 carbon atoms, and each of $R^2$ and $R^4$ independently represents a hydrogen atom or a linear or branched alkyl group having 1 to 8 carbon atoms,

[8] the process according to any one of items [1] to [7], wherein the carbamic acid ester is an aliphatic carbamic acid ester, and a low boiling point component formed with the aryl carbamate is an aliphatic alcohol,

[9] the process according to item [8], wherein the aliphatic carbamic acid ester is an aliphatic polycarbamic acid ester,

[10] the process according to item [8], further comprising the steps of:

continuously supplying the aliphatic carbamic acid ester and the aromatic hydroxy compound to a reaction vessel so as to react the aliphatic carbamic acid ester and the aromatic hydroxy compound inside the reaction vessel;

recovering a formed low boiling point component in a form of a gaseous component; and continuously extracting a reaction liquid containing the aryl carbamate and the aromatic hydroxy compound from a bottom of the reaction vessel,

[11] the process according to any one of items [1] to [10], wherein the decomposition reaction is a thermal decomposition reaction, and is a reaction in which a corresponding isocyanate and aromatic hydroxy compound are formed from the aryl carbamate,

[12] the process according to item [11], wherein at least one compound of the isocyanate and aromatic hydroxy compound formed by the thermal decomposition reaction of the aryl carbamate is recovered in a form of a gaseous component,

[13] the process according to item [8], wherein the aliphatic carbamic acid ester is a compound represented by the following formula (11):

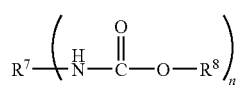
(11)

(wherein $R^7$ represents a group selected from the group consisting of an aliphatic group having 1 to 20 carbon atoms and an aromatic group having 6 to 20 carbon atoms, the group containing an atom selected from a carbon atom, an oxygen atom and a nitrogen atoms, and having a valence of n, $R^8$ represents an aliphatic group which has 1 to 8 carbon atoms and which contains an atom selected from a carbon atom, an oxygen atom and a nitrogen atom, and n represents an integer of 1 to 10),

[14] the process according to item [13], wherein the aliphatic carbamic acid ester is such that $R^8$ in the compound represented by the formula (11) is a group selected from the group consisting of an alkyl group having 1 to 20 carbon atoms and a cycloalkyl group having 5 to 20 carbon atoms,

[15] the process according to item [14], wherein the aliphatic carbamic acid ester is at least one compound selected from the group consisting of compounds represented by the following formulas (12), (13) and (14):

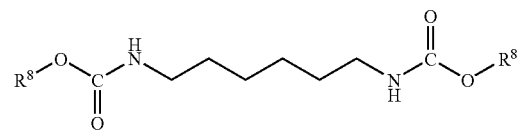
(12)

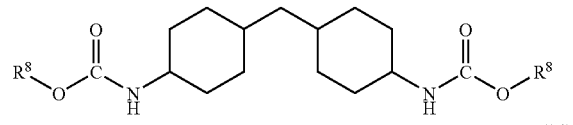
(13)

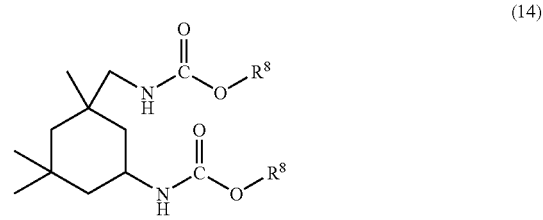
(14)

(wherein $R^8$ is the same as defined above),

[16] an aryl polycarbamate represented by the following formula (15), (16) or (17):

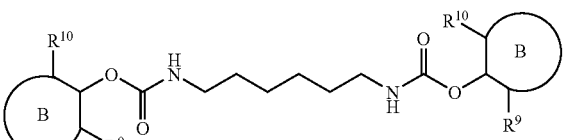
(15)

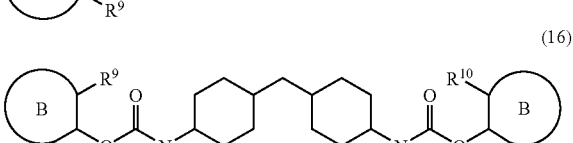
(16)

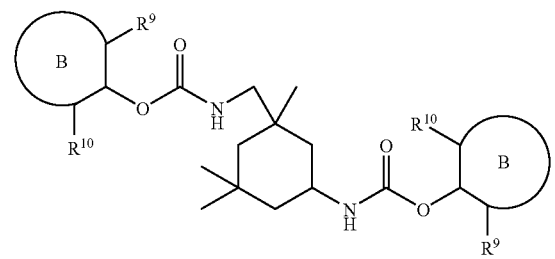
(17)

(wherein a ring B represents a structure which may have a substituent and which contains at least one structure selected from the group consisting of a benzene ring, a naphthalene ring and an anthracene ring, $R^9$ represents a group other than a hydrogen atom in a form of an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the group containing an atom selected from a carbon atom, an oxygen atom and a nitrogen atom, and $R^{10}$ represents an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the aliphatic alkyl, the aliphatic alkoxy, the aryl, the aryloxy, the aralkyl and aralkyloxy groups containing an atom selected from a carbon atom, an oxygen atom and a nitrogen atom),

[17] the aryl polycarbamate according to item [16], which is represented by the following formula (18), (19) or (20):

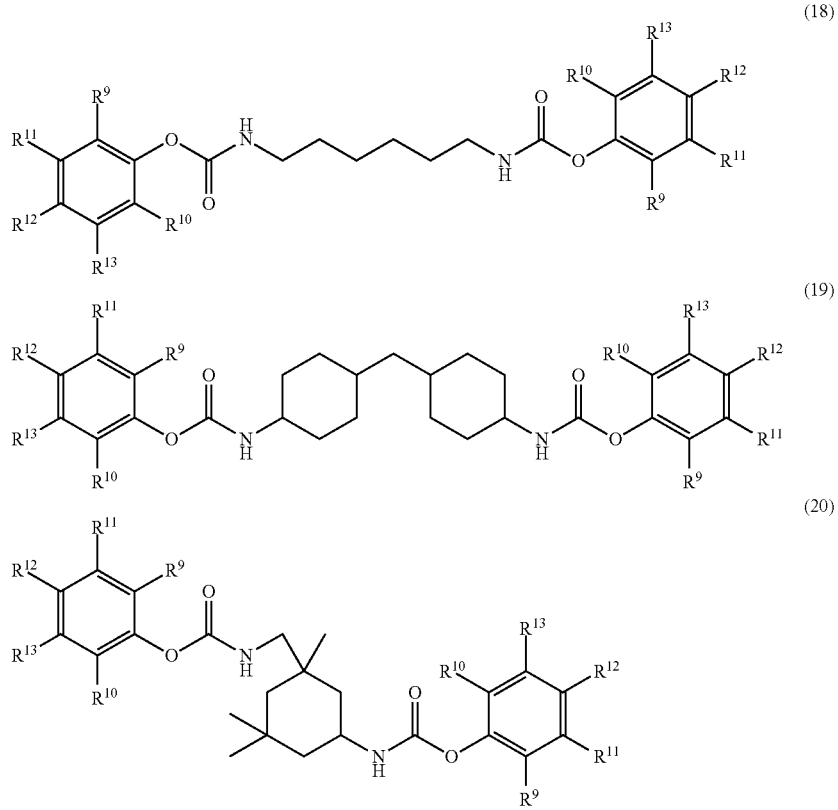

(wherein $R^9$ represents a group other than a hydrogen atom in a form of an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the group containing an atom selected from a carbon atom, an oxygen atom and a nitrogen atom, and each of $R^{10}$, $R^{11}$, $R^{12}$ and $R^{13}$ independently represents a hydrogen atom or an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the aliphatic alkyl, the aliphatic alkoxy, the aryl, the aryloxy, the aralkyl, and the aralkyloxy groups containing an atom selected from a carbon atom, an oxygen atom and a nitrogen atoms).

Advantageous Effect of the Invention

According to the present invention, an isocyanate can be produced efficiently without using phosgene.

9
DESCRIPTION OF REFERENCE NUMERICALS (FIG. 1)
101, 107: distillation column, 102: column-type reaction vessel, 103, 106: thin film evaporator, 104: autoclave, 105: decarbonization tank, 111, 112, 117: reboiler, 121, 123, 126, 127: condenser, 1, 9: supply line, 2, 4, 5, 6, 7, 8, 10, 11, 12, 13, 14: transfer line, 3, 15: recovery line, 16: extraction line, 17: feed line.

Figure 2:
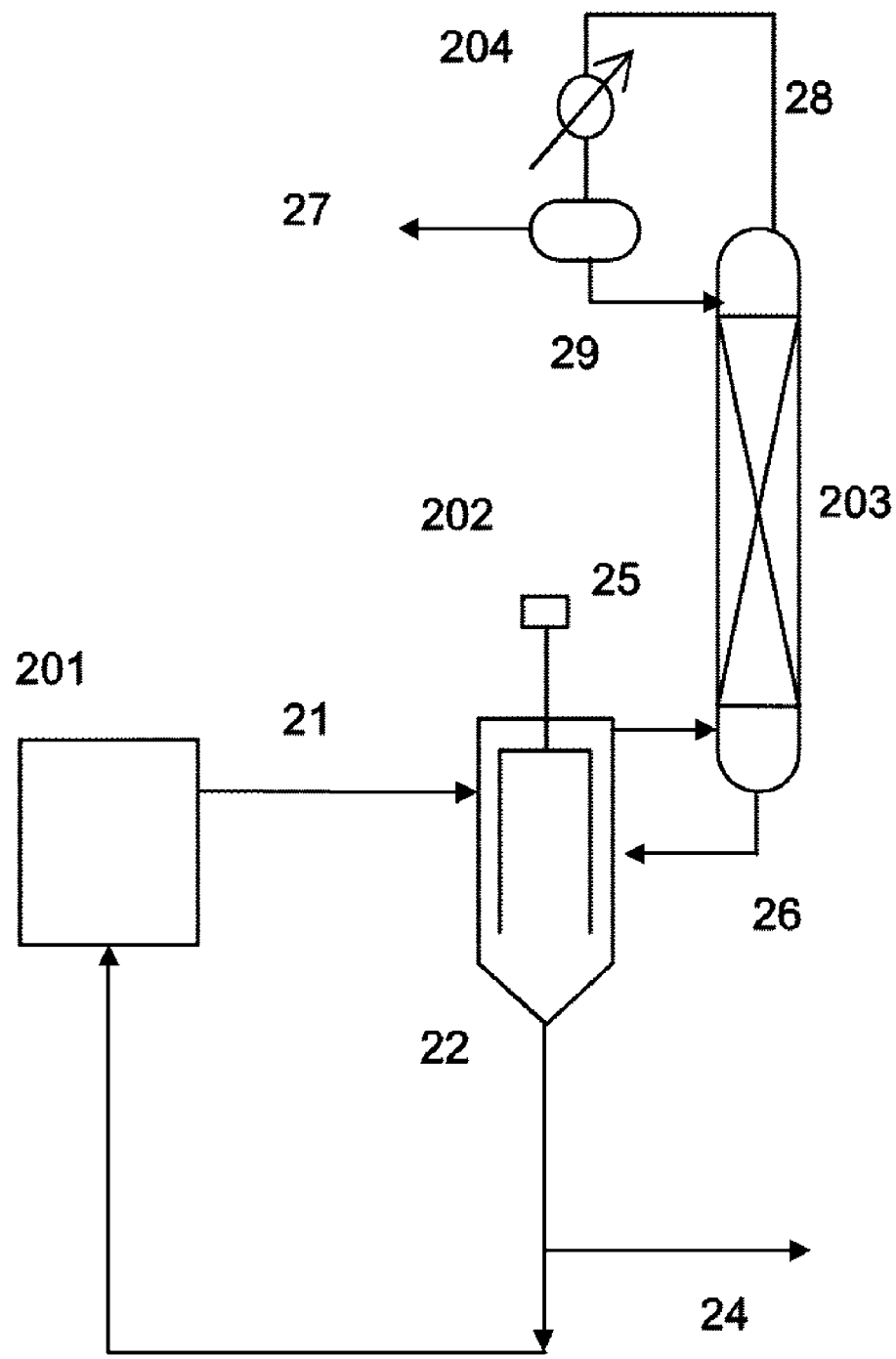
FIG. 2 shows a conceptual drawing showing a transesterification reaction apparatus according to an embodiment of the present invention.
Figure 3:
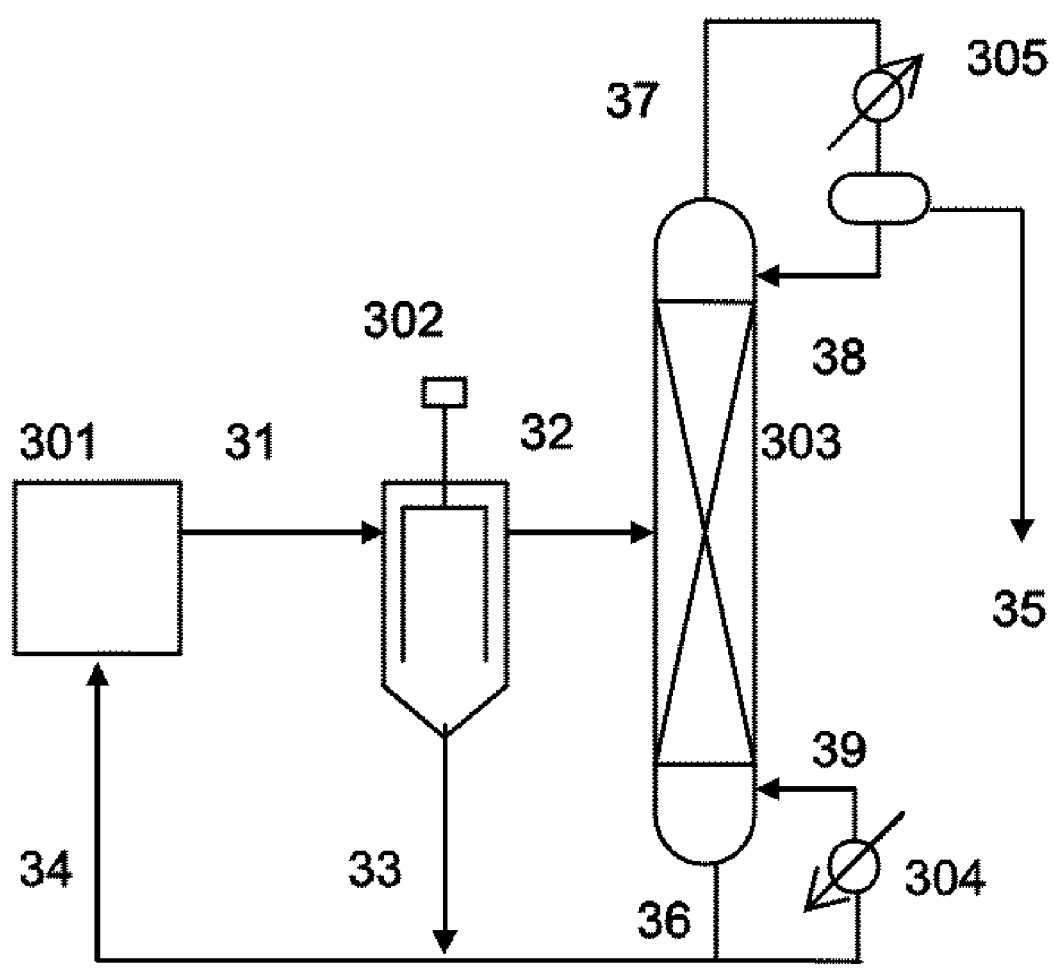
FIG. 3 shows a conceptual drawing showing a thermal decomposition reaction apparatus according to an embodiment of the present invention.
Figure 4:
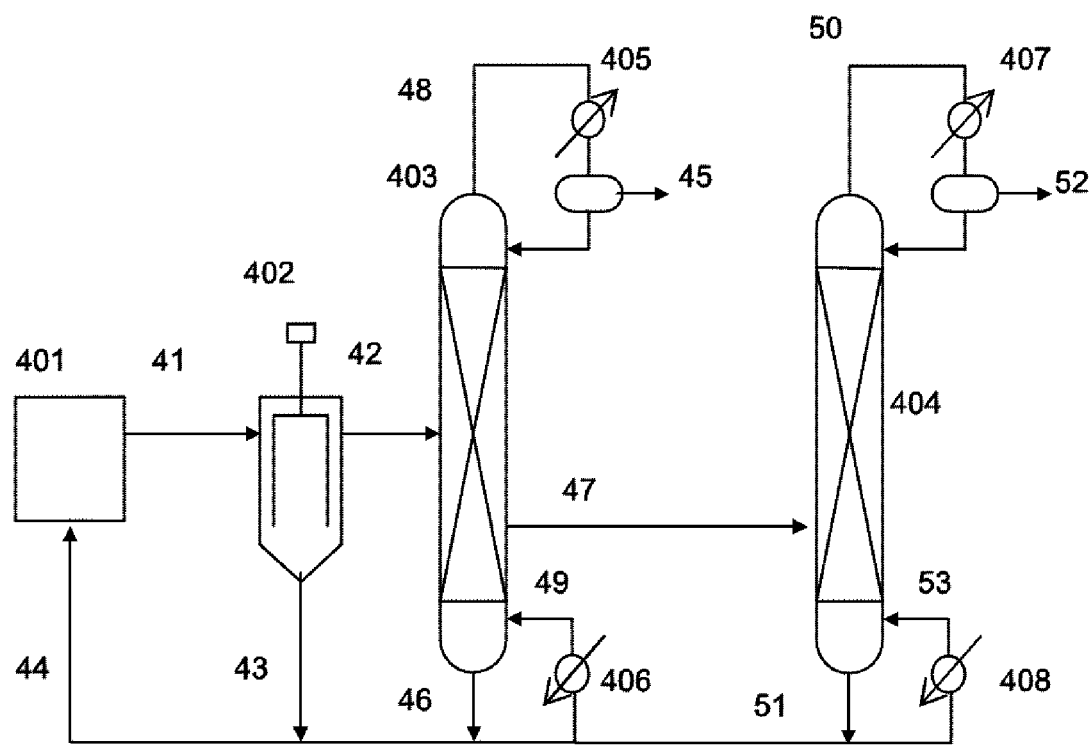
FIG. 4 shows a conceptual drawing showing a thermal decomposition reaction apparatus according to an embodiment of the present invention.

(FIG. 2)
201: feed tank, 202: thin film evaporator, 203: distillation column, 204 condenser, 21, 22, 23, 24, 25, 26, 27, 28, 29: transfer line (FIG. 3)
301: feed tank, 302: thin film evaporator, 303: distillation column, 304 reboiler, 305: condenser, 31, 32, 33, 34, 35, 36, 37, 38, 39, transfer line (FIG. 4)
401: feed tank, 402: thin film evaporator, 403, 404: distillation column, 405, 407, condenser, 406, 408: reboiler, 41, 42, 43, 44, 45, 46, 47, 48, 49, 50, 51, 52, 53: transfer line (FIG. 5)
601, 604: stirring tank, 602, 605, 608: tank, 603, 606, 609: thin film evaporator, 607, 610: distillation column, 611, 613: condenser, 612: reboiler, 61, 62, 63, 64, 65, 66, 67, 68, 69, 70, 71, 72, 73, 74, 75, 76, 77, 78, 79, 80, 81: transfer line

BEST MODE FOR CARRYING OUT THE INVENTION

The following provides a detailed explanation of the best mode for carrying out the present invention (to be referred to as the present embodiment). Furthermore, the present invention is not limited to the following present embodiment, but rather can be modified in various ways within the scope of the gist thereof.

The isocyanate production process of the present embodiment is a process for producing isocyanates which comprises the steps of: reacting a carbamic acid ester and an aromatic hydroxy compound to obtain an aryl carbamate having a group derived from the aromatic hydroxy compound; and subjecting the aryl carbamate to a decomposition reaction; wherein the aromatic hydroxy compound uses an aromatic compound having a specific composition.

The following indicates an example of the detailed reaction scheme of the present embodiment. However, the isocyanate production process as claimed in the present invention is not limited to the following reaction scheme.

TABLE 1

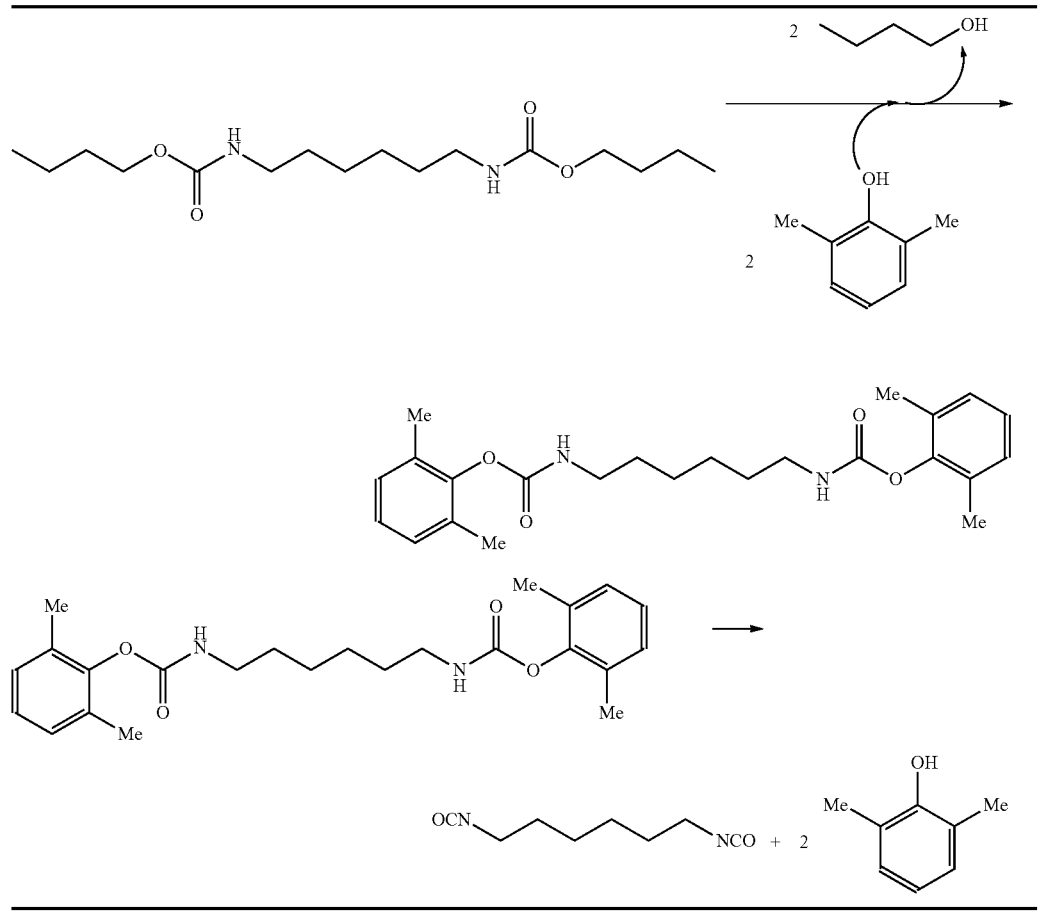

To begin with, an explanation is provided of those compounds used in the isocyanate production process of the present embodiment.

<Aromatic Hydroxy Compounds>

The aromatic hydroxy compounds used in the isocyanate production process of the present embodiment are aromatic hydroxy compounds which are represented by the following formula (5) and which have a substituent at least one site ortho to a hydroxyl group:

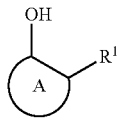

(5)

(wherein ring A represents an aromatic hydrocarbon ring in a form of a single or multiple rings and which have a substitute and which have 6 to 20 carbon atoms;

$R^1$ represents a group other than a hydrogen atom in a form of an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the group containing an atom selected from a carbon atom, an oxygen atom and a nitrogen atom, and $R^1$ may bond with A to form a ring structure).

Examples of $R^1$ in formula (1) above include aliphatic alkyl groups in which the number of carbon atoms constituting the group is a number selected from integers of 1 to 20, such as a methyl group, an ethyl group, a propyl group (isomers), a butyl group (isomers), a pentyl group (isomers), a hexyl group (isomers), a heptyl group (isomers), an octyl group (isomers), a nonyl group (isomers), a decyl group (isomers), a dodecyl group (isomers), an octadecyl group (isomers) or the like; aliphatic alkoxy groups in which the number of carbon atoms constituting the group is a number selected from integers of 1 to 20, such as a methoxy group, an ethoxy group, a propoxy group (isomers), a butyloxy group (isomers), a pentyloxy group (isomers), a hexyloxy group (isomers), a heptyloxy group (isomers), an octyloxy group (isomers), a nonyloxy group (isomers), a decyloxy group (isomers), a dodecyloxy group (isomers), an octadecyloxy group (including isomers) or the like; aryl groups in which the number of carbon atoms constituting the group is 6 to 20, such as a phenyl group, a methylphenyl group (isomers), an ethylphenyl group (isomers), a propylphenyl group (isomers), a butylphenyl group (isomers), a pentylphenyl group (isomers), a hexylphenyl group (isomers), a heptylphenyl group (isomers), an octylphenyl group (isomers), a nonylphenyl group (isomers), a decylphenyl group (isomers), a biphenyl group (isomers), a dimethylphenyl group (isomers), a diethylphenyl group (isomers), a dipropylphenyl group (isomers), a dibutylphenyl group (isomers), a dipentylphenyl group (isomers), a dihexylphenyl group (isomers), a diheptylphenyl group (isomers), a terphenyl group (isomers), a trimethylphenyl group (isomers), a triethylphenyl group (isomers), a tripropylphenyl group (isomers), a tributylphenyl group (isomers) or the like; aryloxy groups in which the number of carbon atoms constituting the group is 6 to 20, such as a phenoxy group, a methylphenoxy group (isomers), an ethylphenoxy group (isomers), a propylphenoxy group (isomers), a butylphenoxy group (isomers), a pentylphenoxy group (isomers), a hexylphenoxy group (isomers), a heptylphenoxy group (isomers), an octylphenoxy group (isomers), a nonylphenoxy group (isomers), a decylphenoxy group (isomers), a phenylphenoxy group (isomers), a dimethylphenoxy group (isomers), a diethylphenoxy group (isomers), a dipropylphenoxy group (isomers), a dibutylphenoxy group (isomers), a dipentylphenoxy group (isomers), a dihexylphenoxy group (isomers), a diheptylphenoxy group (isomers), a diphenylphenoxy group (isomers), a trimethylphenoxy group (isomers), a triethylphenoxy group (isomers), a tripropylphenoxy group (isomers), a tributylphenoxy group (isomers) or the like; aralkyl groups in which the number of carbon atoms constituting the group is 7 to 20, such as a phenylmethyl group, a phenylethyl group (isomers), a phenylpropyl group (isomers), a phenylbutyl group (isomers), a phenylpentyl group (isomers), a phenylhexyl group (isomers), a phenylheptyl group (isomers), a phenyloctyl group (isomers), phenylnonyl group (isomers) or the like; and aralkyloxy groups in which the number of carbon atoms constituting the group is 7 to 20, such as a phenylmethoxy group, a phenylethoxy group (isomers), a phenylpropyloxy group (isomers), a phenylbutyloxy group (isomers), a phenylpentyloxy group (isomers), a phenylhexyloxy group (isomers), a phenylheptyloxy group (isomers), a phenyloctyloxy group (isomers), a phenylnonyloxy group (isomers) or the like.

Examples of ring A in formula (1) above include a benzene ring, a naphthalene ring, an anthracene ring, a phenanthrene ring, a naphthacene ring, a chrysene ring, a pyrene ring, a triphenylene ring, a pentalene ring, an azulene ring, a heptalene ring, an indacene ring, a biphenylene ring, an acenaphthylene ring, an aceanthrylene ring, an acephenanthrylene ring or the like, preferable examples include rings selected from the group consisting of a benzene ring, a naphthalene ring and an anthracene ring. In addition, these rings may have a substituent other than the above-mentioned $R^1$, examples of which include aliphatic alkyl groups in which the number of carbon atoms constituting the group is a number selected from integers of 1 to 20, such as a methyl group, an ethyl group, a propyl group (isomers), a butyl group (isomers), a pentyl group (isomers), a hexyl group (isomers), a heptyl group (isomers), an octyl group (isomers), a nonyl group (isomers), a decyl group (isomers), a dodecyl group (isomers), an octadecyl group (isomers) or the like; aliphatic alkoxy groups in which the number of carbon atoms constituting the group is a number selected from integers of 1 to 20, such as a methoxy group, an ethoxy group, a propoxy group (isomers), a butyloxy group (isomers), a pentyloxy group (isomers), a hexyloxy group (isomers), a heptyloxy group (isomers), an octyloxy group (isomers), a nonyloxy group (isomers), a decyloxy group (isomers), a dodecyloxy group (isomers), an octadecyloxy group (isomers) or the like; aryl groups in which the number of carbon atoms constituting the group is 6 to 20, such as a phenyl group, a methylphenyl group (isomers), an ethylphenyl group (isomers), a propylphenyl group (isomers), a butylphenyl group (isomers), a pentylphenyl group (isomers), a hexylphenyl group (isomers), a heptylphenyl group (isomers), an octylphenyl group (isomers), a nonylphenyl group (isomers), a decylphenyl group (isomers), a biphenyl group (isomers), a dimethylphenyl group (isomers), a diethylphenyl group (isomers), a dipropylphenyl group (isomers), a dibutylphenyl group (isomers), a dipentylphenyl group (isomers), a dihexylphenyl group (isomers), a diheptylphenyl group (isomers), a terphenyl group (isomers), a trimethylphenyl group (isomers), a triethylphenyl group (isomers), a tripropylphenyl group (isomers), a tributylphenyl group (isomers) or the like; aryloxy groups in which the number of carbon atoms constituting the group is 6 to 20, such as a phenoxy group, a methylphenoxy group (isomers), an ethylphenoxy group (isomers), a propylphenoxy group (isomers), a butylphenoxy group (isomers), a pentylphenoxy group (isomers), a hexylphenoxy group (isomers), a heptylphenoxy group (isomers), an octylphenoxy group (isomers), a nonylphenoxy group (isomers), a decylphenoxy group (isomers), a phenylphenoxy group (isomers), a dimethylphenoxy group (isomers), a diethylphenoxy group (isomers), a dipropylphenoxy group (isomers), a dibutylphenoxy group (isomers), a dipentylphenoxy group (isomers), a dihexylphenoxy group isomers), a diheptylphenoxy group (isomers), a diphenylphenoxy group (isomers), a trimethylphenoxy group (isomers), a triethylphenoxy group (isomers), a tripropylphenoxy group (isomers), a tributylphenoxy group (isomers) or the like; aralkyl groups in which the number of carbon atoms constituting the group is 7 to 20, such as a phenylmethyl group, a phenylethyl group (isomers), a phenylpropyl group (isomers), a phenylbutyl group (isomers), a phenylpentyl group (isomers), a phenylhexyl group (isomers), a phenylheptyl group (isomers), a phenyloctyl group (isomers), a phenylnonyl group (isomers) or the like; and aralkyloxy groups in which the number of carbon atoms constituting the group is 7 to 20, such as a phenylmethoxy group, a phenylethoxy group (isomers), a phenylpropyloxy group (isomers), a phenylbutyloxy group (isomers), a phenylpentyloxy group (isomers), a phenylhexyloxy group (isomers), a phenylheptyloxy group (isomers), a phenyloctyloxy group (isomers), a phenylnonyloxy group (isomers).

In addition, the aromatic hydroxy compounds can be used preferably whether it is an aromatic hydroxy compound having a substituent at one ortho position to a hydroxyl group or an aromatic hydroxy compound having substituents at two ortho positions to a hydroxyl group as in compounds represented by the following formula (6):

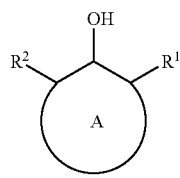

(6)

(wherein ring A and $R^1$ are the same as defined above, $R^2$ represents an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 atoms, the aliphatic alkyl, the aliphatic alkoxy, the aryl, the aryloxy, the aralkyl, and the aralkyloxy groups containing atoms selected from a carbon atom, an oxygen atom and a nitrogen atom, and $R^2$ may bond with A to form a ring structure).

Examples of $R^2$ in the above-mentioned formula (6) include a hydrogen atom; aliphatic alkyl groups in which the number of carbon atoms constituting the group is a number selected from integers of 1 to 20, such as a methyl group, an ethyl group, a propyl group (isomers), a butyl group (isomers), a pentyl group (isomers), a hexyl group (isomers), a heptyl group (isomers), an octyl group (isomers), a nonyl group (isomers), a decyl group (isomers), a dodecyl group (isomers), an octadecyl group (isomers) or the like; aliphatic alkoxy groups in which the number of carbon atoms constituting the group is a number selected from integers of 1 to 20, such as a methoxy group, an ethoxy group, a propoxy group (isomers), a butyloxy group (isomers), a pentyloxy group (isomers), a hexyloxy group (isomers), a heptyloxy group (isomers), an octyloxy group (isomers), a nonyloxy group (isomers), a decyloxy group (isomers), a dodecyloxy group (isomers), an octadecyloxy group (isomers) or the like; aryl groups in which the number of carbon atoms constituting the group is 6 to 20, such as a phenyl group, a methylphenyl group (isomers), an ethylphenyl group (isomers), a propylphenyl group (isomers), a butylphenyl group (isomers), a pentylphenyl group (isomers), a hexylphenyl group (isomers), a heptylphenyl group (isomers), an octylphenyl group (isomers), a nonylphenyl group (isomers), a decylphenyl group (isomers), a biphenyl group (isomers), a dimethylphenyl group (isomers), a diethylphenyl group (isomers), a dipropylphenyl group (isomers), a dibutylphenyl group (isomers), a dipentylphenyl group (isomers), a dihexylphenyl group (isomers), a diheptylphenyl group (isomers), a terphenyl group (isomers), a trimethylphenyl group (isomers), a triethylphenyl group (isomers), a tripropylphenyl group (isomers), a tributylphenyl group (isomers) or the like; aryloxy groups in which the number of carbon atoms constituting the group is 6 to 20, such as a phenoxy group, a methylphenoxy group (isomers), an ethylphenoxy group (isomers), a propylphenoxy group (isomers), a butylphenoxy group (isomers), a pentylphenoxy group (isomers), a hexylphenoxy group (isomers), a heptylphenoxy group (isomers), an octylphenoxy group (isomers), a nonylphenoxy group (isomers), a decylphenoxy group (isomers), a phenylphenoxy group (isomers), a dimethylphenoxy group (isomers), a diethylphenoxy group (isomers), a dipropylphenoxy group (isomers), a dibutylphenoxy group (isomers), a dipentylphenoxy group (isomers), a dihexylphenoxy group (isomers), a diheptylphenoxy group (isomers), a diphenylphenoxy group (isomers), a trimethylphenoxy group (isomers), a triethylphenoxy group (isomers), a tripropylphenoxy group (isomers), a tributylphenoxy group (isomers) or the like; aralkyl groups in which the number of carbon atoms constituting the group is 7 to 20, such as a phenylmethyl group, a phenylethyl group (isomers), a phenylpropyl group (isomers), a phenylbutyl group (isomers), a phenylpentyl group (isomers), a phenylhexyl group (isomers), a phenylheptyl group (isomers), a phenyloctyl group (isomers), a phenylnonyl group (isomers) or the like; and aralkyloxy groups in which the number of carbon atoms constituting the group is 7 to 20, such as a phenylmethoxy group, a phenylethoxy group (isomers), a phenylpropyloxy group (isomers), a phenylbutyloxy group (isomers), a phenylpentyloxy group (isomers), a phenylhexyloxy group (isomers), a phenylheptyloxy group (isomers), a phenyloctyloxy group (isomers), a phenylnonyloxy group (isomers) or the like.

In the case the aromatic hydroxy compound used in the isocyanate production process of the present embodiment are aromatic hydroxy compounds having substituents at two ortho positions to a hydroxyl group, aromatic hydroxy compounds in which the total number of carbon atoms constituting $R^1$ and $R^2$ is 2 to 20 are used preferably among the compounds represented by the above-mentioned formula (6). There are no particular limitations on the combinations of $R^1$ and $R^2$ provided the total number of carbon atoms constituting $R^1$ and $R^2$ is 2 to 20.

Examples of such aromatic hydroxy compounds include compounds represented by the following formula (7):

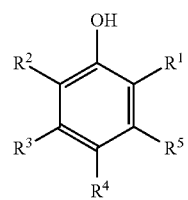

(7)

(wherein $R^1$ and $R^2$ are the same as defined above, and
each of $R^3$, $R^4$ and $R^5$ independently represents a hydrogen atom or an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the aliphatic alkyl, the aliphatic alkoxy, the aryl, the aryloxy, the aralkyl, and the aralkyloxy groups containing an atom selected from a carbon atom, an oxygen atom and a nitrogen atoms).

In particular, aromatic hydroxy compounds in which each of $R^1$ and $R^4$ in the above-mentioned formula (7) independently represents a group represented by the following formula (8) and $R^2$, $R^3$ and $R^5$ represent hydrogen atoms, or aromatic hydroxy compounds in which $R^1$ in the above-mentioned formula (7) is a linear or branched alkyl group having 1 to 8 carbon atoms and each of $R^2$ and $R^4$ independently represents a hydrogen atom or a linear or branched alkyl group having 1 to 8 carbon atoms, are used preferably:

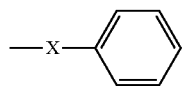

(8)

(wherein X represents a branched structure selected from the structures represented by the following formulas (9) and (10):

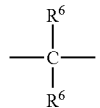

(9)

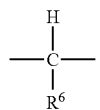

(10)

(wherein $R^6$ represents a linear or branched alkyl group having 1 to 3 carbon atoms).

Examples of such aromatic hydroxy compounds include 2-ethylphenol, 2-propylphenol (isomers), 2-butylphenol (isomers), 2-pentylphenol (isomers), 2-hexylphenol (isomers), 2-heptylphenol (isomers), 2,6-dimethylphenol, 2,4-diethylphenol, 2,6-diethylphenol, 2,4-dipropylphenol (isomers), 2,6-dipropylphenol (isomers), 2,4-dibutylphenol (isomers), 2,4-dipentylphenol (isomers), 2,4-dihexylphenol (isomers), 2,4-diheptylphenol (isomers), 2-methyl-6-ethylphenol, 2-methyl-6-propylphenol (isomers), 2-methyl-6-butylphenol (isomers), 2-methyl-6-pentylphenol (isomers), 2-ethyl-6-propylphenol (isomers), 2-ethyl-6-butylphenol (isomers), 2-ethyl-6-pentylphenol (isomers), 2-propyl-6-butylphenol (isomers), 2-ethyl-4-methylphenol (isomers), 2-ethyl-4-propylphenol (isomers), 2-ethyl-4-butylphenol (isomers), 2-ethyl-4-pentylphenol (isomers), 2-ethyl-4-hexylphenol (isomers), 2-ethyl-4-heptylphenol (isomers), 2-ethyl-4-octylphenol (isomers), 2-ethyl-4-phenylphenol (isomers), 2-ethyl-4-cumylphenol (isomers), 2-propyl-4-methylphenol (isomers), 2-propyl-4-ethylphenol (isomers), 2-propyl-4-butylphenol (isomers), 2-propyl-4-pentylphenol (isomers), 2-propyl-4-hexylphenol (isomers), 2-propyl-4-heptylphenol (isomers), 2-propyl-4-octylphenol (isomers), 2-propyl-4-phenylphenol (isomers), 2-propyl-4-cumylphenol (isomers), 2-butyl-4-methylphenol (isomers), 2-butyl-4-ethylphenol (isomers), 2-butyl-4-propylphenol (isomers), 2-butyl-4-pentylphenol (isomers), 2-butyl-4-hexylphenol (isomers), 2-butyl-4-heptylphenol (isomers), 2-butyl-4-octylphenol (isomers), 2-butyl-4-phenylphenol (isomers), 2-butyl-4-cumylphenol (isomers), 2-pentyl-4-methylphenol (isomers), 2-pentyl-4-ethylphenol (isomers), 2-pentyl-4-propylphenol (isomers), 2-pentyl-4-butylphenol (isomers), 2-pentyl-4-hexylphenol (isomers), 2-pentyl-4-heptylphenol (isomers), 2-pentyl-4-octylphenol (isomers), 2-pentyl-4-phenylphenol (isomers), 2-pentyl-4-cumylphenol (isomers), 2-hexyl-4-methylphenol (isomers), 2-hexyl-4-ethylphenol (isomers), 2-hexyl-4-propylphenol (isomers), 2-hexyl-4-butylphenol (isomers), 2-hexyl-4-pentylphenol (isomers), 2-hexyl-4-heptylphenol (isomers), 2-hexyl-4-octylphenol (isomers), 2-hexyl-4-phenylphenol (isomers), 2-hexyl-4-cumylphenol (isomers), 2-heptyl-4-methylphenol (isomers), 2-heptyl-4-ethylphenol (isomers), 2-heptyl-4-propylphenol (isomers), 2-heptyl-4-butylphenol (isomers), 2-heptyl-4-pentylphenol (isomers), 2-heptyl-4-hexylphenol (isomers), 2-heptyl-4-octylphenol (isomers), 2-heptyl-4-phenylphenol (isomers), 2-heptyl-4-cumylphenol (isomers), 2,4,6-trimethylphenol, 2,6-dimethyl-4-ethyl phenol, 2,6-dimethyl-4-propylphenol (isomers), 2,6-dimethyl-4-butylphenol (isomers), 2,6-dimethyl-4-pentylphenol (isomers), 2,6-dimethyl-4-hexylphenol (isomers), 2,6-dimethyl-4-phenylphenol (isomers), 2,6-dimethyl-4-cumylphenol (isomers), 2,4,6-triethylphenol, 2,6-diethyl-4-methylphenol, 2,6-diethyl-4-propylphenol (isomers), 2,6-diethyl-4-butylphenol (isomers), 2,6-diethyl-4-pentylphenol (isomers), 2,6-diethyl-4-hexylphenol (isomers), 2,6-diethyl-4-phenylphenol (isomers), 2,6-diethyl-4-cumylphenol (isomers), 2,4,6-tripropylphenol (isomers), 2,6-dipropyl-4-ethylphenol (isomers), 2,6-dipropyl-4-methylphenol (isomers), 2,6-dipropyl-4-butylphenol (isomers), 2,6-dipropyl-4-pentylphenol (isomers), 2,6-dipropyl-4-hexylphenol (isomers), 2,6-dipropyl-4-phenylphenol (isomers), 2,6-dipropyl-4-cumylphenol (isomers), 2,4-dimethyl-6-ethylphenol, 2-methyl-4,6-diethylphenol, 2-methyl-4-propyl-6-ethylphenol (isomers), 2-methyl-4-butyl-6-ethylphenol (isomers), 2-methyl-4-pentyl-6-ethylphenol (isomers), 2-methyl-4-hexyl-6-ethylphenol (isomers), 2-methyl-4-phenyl-6-ethylphenol (isomers), 2-methyl-4-cumyl-6-ethylphenol (isomers), 2,4-dimethyl-6-propylphenol (isomers), 2-methyl-4,6-dipropylphenol (isomers), 2-methyl-4-ethyl-6-propylphenol (isomers), 2-methyl-4-butyl-6-propylphenol (isomers), 2-methyl-4-pentyl-6-propylphenol (isomers), 2-methyl-4-hexyl-6-propylphenol (isomers), 2-methyl-4-phenyl-6-propylphenol (isomers), 2-methyl-4-cumyl-6-propylphenol (isomers), 2,4-dimethyl-6-butylphenol (isomers), 2-methyl-4,6-dibutylphenol (isomers), 2-methyl-4-propyl-6-butylphenol (isomers), 2-methyl-4-ethyl-6-butylphenol (isomers), 2-methyl-4-pentyl-6-butylphenol (isomers), 2-methyl-4-hexyl-6-butylphenol (isomers), 2-methyl-4-phenyl-6-butyl phenol (isomers), 2-methyl-4-cumyl-6-butyl phenol (isomers), 2,4-dimethyl-6-pentylphenol, 2-methyl-4,6-dipentylphenol, 2-methyl-4-propyl-6-pentylphenol, 2-methyl-4-butyl-6-pentylphenol (isomers), 2-methyl-4-ethyl-6-pentylphenol (isomers), 2-methyl-4-hexyl-6-pentylphenol (isomers), 2-methyl-4-phenyl-6-pentylphenol (isomers), 2-methyl-4-cumyl-6-pentylphenol (isomers), 2,4-dimethyl-6-hexylphenol, 2-methyl-4,6-dihexylphenol, 2-methyl-4-propyl-6-hexylphenol (isomers), 2-methyl-4-butyl-6-hexylphenol (isomers), 2-methyl-4-pentyl-6-hexylphenol (isomers), 2-methyl-4-ethyl-6-hexylphenol (isomers), 2-methyl-4-phenyl-6-hexylphenol (isomers), 2-methyl-4-cumyl-6-hexylphenol (isomers), 2-ethyl-4-methyl-6-propylphenol (isomers), 2,4-diethyl-6-propylphenol (isomers), 2-ethyl-4,6-dipropylphenol (isomers), 2-ethyl-4-butyl-6-propylphenol (isomers), 2-ethyl-4-pentyl-6-propylphenol (isomers), 2-ethyl-4-hexyl-6-propylphenol (isomers), 2-ethyl-4-heptyl-6-propylphenol (isomers), 2-ethyl-4-octyl-6-propylphenol (isomers), 2-ethyl-4-phenyl-6-propylphenol (isomers), 2-ethyl-4-cumyl-6-propylphenol (isomers), 2-ethyl-4-methyl-6-butylphenol (isomers), 2,4-diethyl-6-butylphenol (isomers), 2-ethyl-4,6-dibutylphenol (isomers), 2-ethyl-4-propyl-6-butylphenol (isomers), 2-ethyl-4-pentyl-6-butylphenol (isomers), 2-ethyl-4-hexyl-6-butylphenol (isomers), 2-ethyl-4-heptyl-6-butylphenol (isomers), 2-ethyl-4-octyl-6-butylphenol (isomers), 2-ethyl-4-phenyl-6-butylphenol (isomers), 2-ethyl-4-cumyl-6-butylphenol (isomers), 2-ethyl-4-methyl-6-pentylphenol (isomers), 2,4-diethyl-6-pentylphenol (isomers), 2-ethyl-4,6-dipentylphenol (isomers), 2-ethyl-4-butyl-6-pentyl phenol (isomers), 2-ethyl-4-propyl-6-pentyl phenol (isomers), 2-ethyl-4-hexyl-6-pentylphenol (isomers), 2-ethyl-4-heptyl-6-pentylphenol (isomers), 2-ethyl-4-octyl-6-pentylphenol (isomers), 2-ethyl-4-phenyl-6-pentylphenol (isomers), 2-ethyl-4-cumyl-6-pentylphenol (isomers), 2-ethyl-4-methyl-6-hexylphenol (isomers), 2,4-diethyl-6-hexylphenol (isomers), 2-ethyl-4,6-dihexylphenol (isomers), 2-ethyl-4-propyl-6-hexylphenol (isomers), 2-ethyl-4-pentyl-6-hexylphenol (isomers), 2-ethyl-4-butyl-6-hexylphenol isomers), 2-ethyl-4-heptyl-6-hexylphenol (isomers), 2-ethyl-4-octyl-6-hexylphenol (isomers), 2-ethyl-4-phenyl-6-hexylphenol (isomers), 2-ethyl-4-cumyl-6-hexylphenol (isomers), 2-propyl-4-methyl-6-butylphenol (isomers), 2,4-dipropyl-6-butylphenol (isomers), 2-propyl-4,6-dibutylphenol (isomers), 2-propyl-4-ethyl-6-butylphenol (isomers), 2-propyl-4-pentyl-6-butylphenol (isomers), 2-propyl-4-hexyl-6-butylphenol (isomers), 2-propyl-4-heptyl-6-butylphenol (isomers), 2-propyl-4-octyl-6-butylphenol (isomers), 2-propyl-4-phenyl-6-butylphenol (isomers) and 2-propyl-4-cumyl-6-butylphenol (isomers) or the like.

The inventors of the present invention surprisingly found that by using the specific aromatic hydroxy compounds as described above, aromatic carbamic acid esters, which were conventionally considered to be unstable, are able to inhibit side reactions like those described above in a transesterification reaction and/or thermal decomposition reaction to be described later. Although the mechanism by which the aromatic hydroxy compound inhibits the side reactions is unclear, the inventors of the present invention presumed that in the case, for example, R' is a group derived from the aromatic hydroxy compound in the reaction by which a urea bond represented by the above-mentioned formula (2) is formed, the substituent at the ortho position relative to the hydroxyl group sterically protects the urethane bond, thereby hindering the reaction between a different carbamic acid ester and the urethane bond.

The aromatic hydroxy compounds are preferably aromatic hydroxy compounds having a standard boiling point higher than the standard boiling point of a hydroxy compound corresponding to an aliphatic alkoxy group, aryloxy group or aralkyloxy group that composes the ester group of the carbamic acid ester described below. The term "standard boiling point" as referred to in the present invention indicates the boiling point at 1 atmosphere.

<Carbamic Acid Esters>

There are no particular limitations on the carbamic acid ester used in the isocyanate production process of the present embodiment, and an aliphatic carbamic acid ester is used preferably. Examples of aliphatic carbamic acid esters include compounds represented by the following formula (11):

(wherein $R^7$ represents a group selected from the group consisting of an aliphatic group having 1 to 20 carbon atoms and an aromatic group having 6 to 20 carbon atoms, the group containing an atom selected from a carbon atom and an oxygen atom, and having a number of atoms equal to n, $R^8$ represents an aliphatic group having 1 to 8 carbon atoms containing an atom selected from a carbon atom and an oxygen atom, and n represents an integer of 1 to 10).

In formula (11) above, n is preferably a number selected from integers of 2 or more, and more preferably an aliphatic polycarbamic acid ester in which n is 2.

Examples of $R^7$ in formula (11) include linear hydrocarbon groups such as methylene, dimethylene, trimethylene, tetramethylene, pentamethylene, hexamethylene, octamethylene or the like; unsubstituted acyclic hydrocarbon groups such as cyclopentane, cyclohexane, cycloheptane, cyclooctane, bis(cyclohexyl)alkane or the like; alkyl-substituted cyclohexanes such as methylcyclopentane, ethylcyclopentane, methylcyclohexane (isomers), ethylcyclohexane (isomers), propylcyclohexane (isomers), butylcyclohexane (isomers), pentylcyclohexane (isomers), hexylcyclohexane (isomers) or the like; dialkyl-substituted cyclohexanes such as dimethylcyclohexane (isomers), diethylcyclohexane (isomers), dibutylcyclohexane (isomers) or the like; trialkyl-substituted cyclohexanes such as 1,5,5-trimethylcyclohexane, 1,5,5-triethylcyclohexane, 1,5,5-tripropylcyclohexane (isomers), 1,5,5-tributylcyclohexane (isomers) or the like; monoalkyl-substituted benzenes such as toluene, ethylbenzene, propylbenzene or the like; dialkyl-substituted benzenes such as xylene, diethylbenzene, dipropylbenzene or the like; and aromatic hydrocarbons such as diphenylalkane, benzene or the like. In particular, hexamethylene, phenylene, diphenylmethane, toluene, cyclohexane, xylene, methylcyclohexane, isophorone and dicyclohexylmethane are used preferably.

Examples of $R^8$ include alkyl groups in which the number of carbon atoms constituting the group is selected from an integer of 1 to 8, such as a methyl group, an ethyl group, a propyl group (isomers), a butyl group (isomers), a pentyl group (isomers), a hexyl group (isomers), a heptyl group (isomers), an octyl group (isomers) or the like; and cycloalkyl groups in which the number of carbon atoms constituting the group is selected from an integer of 5 to 14, such as a cyclopentyl group, a cyclohexyl group, a cycloheptyl group, a cyclooctyl group, a dicyclopentyl group (isomers), a dicyclohexyl group (isomers), a cyclohexyl-cyclopentyl group or the like.

Examples of alkyl polycarbamates represented by the above-mentioned formula (11) include alkyl carbamates such as N,N'-hexanediyl-bis-carbamic acid dimethyl ester, N,N'-hexanediyl-bis-carbamic acid diethyl ester, N,N'-hexanediyl-bis-carbamic acid dibutyl ester (isomers), N,N'-hexanediyl-bis-carbamic acid dipentyl ester (isomers), N,N'-hexanediyl-bis-carbamic acid dihexyl ester (isomers), N,N'-hexanediyl-bis-carbamic acid dioctyl ester (isomers), dimethyl-4,4'-methylene-dicyclohexyl carbamate, diethyl-4,4'-methylene-dicyclohexyl carbamate, dipropyl-4,4'-methylene-dicyclohexyl carbamate (isomers), dibutyl-4,4'-methylene-dicyclohexyl carbamate (isomers), dipentyl-4,4'-methylenedicyclohexyl carbamate (isomers), dihexyl-4,4'-methylene-dicyclohexyl carbamate (isomers), diheptyl-4,4'-methylene-dicyclohexyl carbamate (isomers), dioctyl-4,4'-methylene-dicyclohexyl carbamate (isomers), 3-(methoxycarbonylamino-methyl)-3,5,5-trimethylcyclohexyl carbamic acid methyl ester, 3-(ethoxycarbonylamino-methyl)-3,5,5-trimethylcyclohexyl carbamic acid ethyl ester, 3-(propyloxycarbonylamino-methyl)-3,5,5-trimethylcyclohexyl carbamic acid propyl ester (isomers), 3-(butyloxycarbonylamino-methyl)-3,5,5-trimethylcyclohexyl carbamic acid butyl ester (isomers), 3-(pentyloxycarbonylamino-methyl)-3,5,5-trimethylcyclohexyl carbamic acid pentyl ester (isomers), 3-(hexyloxycarbonylamino-methyl)-3,5,5-trimethylcyclohexyl carbamic acid hexyl ester (isomers), 3-(heptyloxycarbonylamino-methyl)-3,5,5-trimethylcyclohexyl carbamic acid heptyl ester (isomers), 3-(octyloxycarbonylamino-methyl)-3,5,5-trimethylcyclohexyl carbamic acid octyl ester (isomers), toluene-dicarbamic acid dimethyl ester (isomers), toluene-dicarbamic acid diethyl ester (isomers), toluene-dicarbamic acid dipropyl ester (isomers), toluene-dicarbamic acid dibutyl ester (isomers), toluene-dicarbamic acid dipentyl ester (isomers), toluene-dicarbamic acid dihexyl ester (isomers), toluene-dicarbamic acid diheptyl ester (isomers), toluene-dicarbamic acid dioctyl ester (isomers), N,N'-(4,4'-methanediyl-diphenyl)-biscarbamic acid dimethyl ester, N,N'-(4,4'-methanediyl-diphenyl)-biscarbamic acid diethyl ester, N,N'-(4,4'-methanediyl-diphenyl)-biscarbamic acid dipropyl ester, N,N'-(4,4'-methanediyl-diphenyl)-biscarbamic acid dibutyl ester, N,N'-(4,4'-methanediyl-diphenyl)-biscarbamic acid dipentyl ester, N,N'-(4,4'-methanediyl-diphenyl)-biscarbamic acid dihexyl ester, N,N'-(4,4'-methanediyl-diphenyl)-biscarbamic acid diheptyl ester, N,N'-(4,4'-methanediyl-diphenyl)-biscarbamic acid dioctyl ester or the like.

Among these, alkyl carbamates in which $R^7$ in formula (11) above is a group selected from the group consisting of an alkyl group having 1 to 20 carbon atoms and a cycloalkyl group having 5 to 20 carbon atoms are used preferably, while alkyl carbamates represented by any of the following formulas (12) to (14) are used particularly preferably:

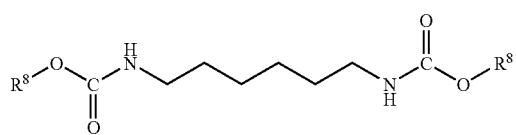

(12)

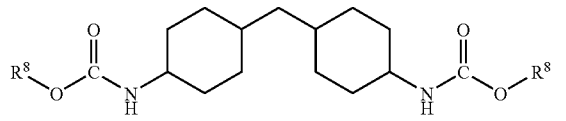

(13)

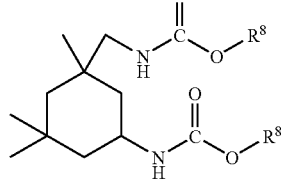

(14)

(wherein $R^8$ is the same as defined above).

Examples of alkyl polycarbamates represented by formula (12) include N,N'-hexanediyl-bis-carbamic acid dimethyl ester, N,N'-hexanediyl-bis-carbamic acid diethyl ester, N,N'-hexanediyl-bis-carbamic acid dibutyl ester (isomers), N,N'-hexanediyl-bis-carbamic acid dipentyl ester (isomers), N,N'-hexanediyl-bis-carbamic acid dihexyl ester (isomers) and N,N'-hexanediyl-bis-carbamic acid dioctyl ester (including isomers). In addition, examples of alkyl polycarbamates represented by formula (13) include dimethyl-4,4'-methylene-dicyclohexyl carbamate, diethyl-4,4'-methylene-dicyclohexyl carbamate, dipropyl-4,4'-methylene-dicyclohexyl carbamate (isomers), dibutyl-4,4'-methylene-dicyclohexyl carbamate (isomers), dipentyl-4,4'-methylene-dicyclohexyl carbamate (isomers), dihexyl-4,4'-methylene-dicyclohexyl carbamate (isomers), diheptyl-4,4'-methylene-dicyclohexyl carbamate (isomers) and dioctyl-4,4'-methylene-dicyclohexyl carbamate (isomers). Moreover, examples of alkyl polycarbamates represented by formula (14) include alkyl polycarbamates such as 3-(methoxycarbonylamino-methyl)-3,5,5-trimethylcyclohexyl carbamic acid methyl ester, 3-(ethoxycarbonylamino-methyl)-3,5,5-trimethylcyclohexyl carbamic acid ethyl ester, 3-(propyloxycarbonylamino-methyl)-3,5,5-trimethylcyclohexyl carbamic acid propyl ester (isomers), 3-(butyloxycarbonylamino-methyl)-3,5,5-trimethylcyclohexyl carbamic acid butyl ester (isomers), 3-(pentyloxycarbonylamino-methyl)-3,5,5-trimethylcyclohexyl carbamic acid pentyl ester (isomers), 3-(hexyloxycarbonylamino-methyl)-3,5,5-trimethylcyclohexyl carbamic acid hexyl ester (isomers), 3-(heptyloxycarbonylamino-methyl)-3,5,5-trimethylcyclohexyl carbamic acid heptyl ester (isomers), 3-(octyloxycarbonylamino-methyl)-3,5,5-trimethylcyclohexyl carbamic acid octyl ester (isomers) or the like.

A known method can be used to produce the carbamic acid esters. For example, carbamic esters may be produced by reacting amine compounds with carbon monoxide, oxygen and aliphatic alcohols or aromatic hydroxy compounds, or reacting amine compounds with urea and aliphatic alcohols or aromatic hydroxy compounds. In the present embodiment, the carbamic acid esters are preferably produced by reacting carbonic acid esters and amine compounds.

The following provides an explanation of the production of alkyl carbamates by reacting dialkyl carbonates and amine compounds.

Dialkyl carbonates represented by the following formula (21) can be used for the dialkyl carbonates:

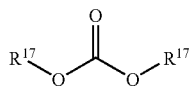

(21)

(wherein $R^{17}$ represents a linear or branched alkyl group having 1 to 8 carbon atoms).

Examples of $R^{17}$ include alkyl groups in a form of aliphatic hydrocarbon groups in which the number of carbon atoms constituting the group is a number selected from an integer of 1 to 8, such as a methyl group, an ethyl group, a propyl group (isomers), a butyl group (isomers), a pentyl group (isomers), a hexyl group (isomers), a heptyl group (isomers), an octyl group (isomers) or the like. Examples of such dialkyl carbonates include dimethyl carbonate, diethyl carbonate, dipropyl carbonate (isomers), dibutyl carbonate (isomers), dipentyl carbonate (isomers), dihexyl carbonate (isomers), diheptyl carbonate (isomers) and dioctyl carbonate (isomers). Among these, a dialkyl carbonate in which the number of carbon atoms constituting the alkyl groups is a number selected from an integer of 4 to 6 is used particularly preferably.

Amine compounds represented by the following formula (22) are preferably used for the amine compounds:

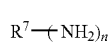
(22)

(wherein $R^7$ represents a group selected from the group consisting of an aliphatic group having 1 to 20 carbon atoms and an aromatic group having 6 to 20 carbon atoms, the group containing an atom selected from a carbon atom and an oxygen atom, and having a valence of n, and n represents an integer of 1 to 10).

In formula (22) above, a polyamine compound is used in which n is preferably 1 to 3 and more preferably n is 2.

Examples of such polyamine compounds include aliphatic diamines such as hexamethylene diamine, 4,4'-methylenebis (cyclohexylamine) (isomers), cyclohexane diamine (isomers), 3-aminomethyl-3,5,5-trimethylcyclohexyl amine (isomers) or the like; and aromatic diamines such as phenylene diamine (isomers), toluene diamine (isomers), 4,4'-methylene dianiline (isomers) or the like. Among these, aliphatic diamines such as hexamethylene diamine, 4,4'-methylenebis(cyclohexylamine) (isomers), cyclohexane diamine (isomers), 3-aminomethyl-3,5,5-trimethylcyclohexyl amine (isomers) or the like are used preferably, while hexamethylene diamine, 4,4'-methylenebis(cyclohexylamine) and 3-aminomethyl-3,5,5-trimethylcyclohexyl amine are used more preferably.

Reaction conditions vary according to the reacted compounds, and although the dialkyl carbonate is preferably in excess based on the amino groups of the amine compound to accelerate the reaction rate and complete the reaction quickly at a stoichiometric ratio of the dialkyl carbonate to amino groups of the amine compound within a range of from 2 to 1000 times, the range is preferably from 2 to 100 times and more preferably from 2.5 to 30 times in consideration of the size of the reaction vessel. The reaction temperature is generally within the range of from normal temperature (20° C.) to 300° C., and although higher temperatures are preferable in order to accelerate the reaction rate, since undesirable reactions may conversely occur at high temperatures, the reaction temperature is preferably within the range of from 50 to 150° C. A known cooling apparatus or heating apparatus may be installed in the reaction vessel to maintain a constant reaction temperature. In addition, although varying according to the types of compounds used and reaction temperature, the reaction pressure may be decreased pressure, normal pressure or increased pressure, and the reaction is generally carried out at a pressure within the range of from 20 to $1 \times 10^6$ Pa. There are no particular limitations on the reaction time (residence time in the case of a continuous method), and is generally from 0.001 to 50 hours, preferably from 0.01 to 10 hours and more preferably from 0.1 to 5 hours. In addition, the reaction can also be completed by confirming that a desired amount of alkyl carbamate has been formed by, for example, liquid chromatography after sampling the reaction liquid. In the present embodiment, a catalyst can be used as necessary, and examples of catalysts that can be used include organic metal compounds and inorganic metal compounds of tin, lead, copper or titanium, and basic catalysts such as alkylates of alkaline metals or alkaline earth metals in the form of methylates, ethylates and butyrates (isomers) of lithium, sodium, potassium, calcium, or barium. Although the use of a reaction solvent is not necessarily required in the present embodiment, a suitable inert solvent is preferably used as a reaction solvent for the purpose of facilitating the reaction procedure, examples of which include alkanes such as hexane (isomers), heptane (isomers), octane (isomers), nonane (isomers), decane (isomers) or the like; aromatic hydrocarbons and alkyl-substituted aromatic hydrocarbons such as benzene, toluene, xylene (isomers), ethyl benzene, diisopropyl benzene (isomers), dibutyl benzene (isomers), naphthalene or the like; aromatic compounds substituted with a halogen or nitro group such as chlorobenzene, dichlorobenzene (isomers), bromobenzene, dibromobenzene (isomers), chloronaphthalene, bromonaphthalene, nitrobenzene, nitronaphthalene or the like; polycyclic hydrocarbon compounds such as diphenyl, substituted diphenyl, diphenyl methane, terphenyl, anthracene, dibenzyl toluene or the like; aliphatic hydrocarbons such as cyclohexane, cyclopentane, cyclooctane, ethylcyclohexane or the like; ketones such as methyl ethyl ketone, acetophenone or the like; esters such as dibutyl phthalate, dihexyl phthalate, dioctyl phthalate, benzylbutyl phthalate or the like; ethers and thioethers such as diphenyl ether, diphenyl sulfide or the like; and sulfoxides such as dimethylsulfoxide, diphenylsulfoxide or the like. These solvents can be used alone or two or more types can be used as a mixture. In addition, the dialkyl carbonate used in excess based on amino groups of the amine compound is also preferably used as a solvent in the reaction.

A known tank reactor, column reactor or distillation column can be used for the reaction vessel, and although known materials may be used for the reaction vessel and lines provided they do not have a detrimental effect on the starting substances or reactants, SUS304, SUS316 or SUS316L and the like can be used preferably since they are inexpensive.

<Transesterification Reaction>

In the isocyanate production process of the present embodiment, carbamic acid esters and aromatic hydroxy compounds are first reacted to obtain aryl carbamates having a group derived from the aromatic hydroxy compounds. This reaction involves an exchange between an aliphatic alkoxy group or aralkyloxy group constituting the ester group of the carbamic acid ester and an aryloxy group derived from the aromatic hydroxy compounds resulting in the formation of the corresponding aryl carbamate and a hydroxy compound derived from the carbamic acid ester (and is referred to as a transesterification reaction in the present description).

Although varying according to the reacted compounds, the reaction conditions of this transesterification reaction are such that the aromatic hydroxy compound is used within the range of from 2 to 1000 times the ester group of the carbamic acid ester when expressed as the stoichiometric ratio. As a result of conducting extensive studies, the inventors of the present invention surprisingly found that by using the aromatic hydroxy compounds having a substituent at least one ortho position with respect to the hydroxyl group in this transesterification reaction as described above, side reactions as previously-described attributable to the carbamic acid ester and/or product in the form of the aryl carbamate can be inhibited in the transesterification reaction. In the transesterification reaction, although the aromatic hydroxy compound is preferably used in excess based on the ester group of the carbamic acid ester in order to inhibit side reactions attributable to the carbamic acid ester and/or product in the form of the aryl carbamate as well as allow the reaction to be completed quickly, the aromatic hydroxy compound is preferably used within the range of from 2 to 100 times and preferably within the range of from 5 to 50 times in consideration of the size of the reaction vessel. The reaction temperature is generally within the range of from 100 to 300° C., and although high temperatures are preferable in order to increase the reaction rate, since there conversely may be greater susceptibility to the occurrence of side reactions at high temperatures, the reaction temperature is preferably within the range of from 150 to 250° C. A known cooling apparatus or heating apparatus may be installed in the reaction vessel to maintain a constant reaction temperature. In addition, although varying according to the types of compounds used and reaction temperature, the reaction pressure may be decreased pressure, normal pressure or increased pressure, and the reaction is generally carried out at a pressure within the range of from 20 to $1\times10^6$ Pa. There are no particular limitations on the reaction time (residence time in the case of a continuous method) and is generally from 0.001 to 100 hours, preferably from 0.01 to 50 hours and more preferably from 0.1 to 30 hours. In addition, the reaction can also be completed by confirming that a desired amount of aryl carbamate has been formed by, for example, liquid chromatography after sampling the reaction liquid. In the present embodiment, the catalyst is used at from 0.01 to 30% by weight and preferably at from 0.5 to 20% by weight based on the weight of the carbamic acid ester. For example, organic metal catalysts such as dibutyl tin dilaurate, ferrous octoate or stannous octoate, or amines such as 1,4-diazabicyclo[2,2,2]octane, triethylenediamine or triethylamine are suitable for use, while organic metal catalysts such as dibutyl tin dilaurate, ferrous octoate or stannous octoate are particularly preferable. These compounds may be used alone or two or more types may be used as a mixture. Although the use of a reaction solvent is not necessarily required in the present embodiment, a suitable inert solvent is preferably used as a reaction solvent for the purpose of facilitating the reaction procedure, examples of which include alkanes such as hexane (isomers), heptane (isomers), octane (isomers), nonane (isomers), decane (isomers) or the like; aromatic hydrocarbons and alkyl-substituted aromatic hydrocarbons such as benzene, toluene, xylene (isomers), ethylbenzene, diisopropylbenzene (isomers), dibutylbenzene (isomers), naphthalene or the like; aromatic compounds substituted with a halogen or nitro group such as chlorobenzene, dichlorobenzene (isomers), bromobenzene, dibromobenzene (isomers), chloronaphthalene, bromonaphthalene, nitrobenzene, nitronaphthalene or the like; polycyclic hydrocarbon compounds such as diphenyl, substituted diphenyl, diphenyl methane, terphenyl, anthracene, dibenzyltoluene (isomers) or the like; aliphatic hydrocarbons such as cyclohexane, cyclopentane, cyclooctane, ethylcyclohexane or the like; ketones such as methyl ethyl ketone, acetophenone or the like; esters such as dibutyl phthalate, dihexyl phthalate, dioctyl phthalate, benzylbutyl phthalate or the like; ethers and thioethers such as diphenyl ether, diphenyl sulfide or the like; and sulfoxides such as dimethylsulfoxide, diphenylsulfoxide or the like; and, silicone oil. These solvents can be used alone or two or more types can be used as a mixture.

As has been described above, although the transesterification reaction in the present embodiment involves the exchange between the aliphatic alkoxy group constituting the ester group of the carbamic acid ester and the aryloxy group derived from the aromatic hydroxy compound resulting in the formation of the corresponding aryl carbamates and the alcohols, the transesterification reaction is an equilibrium reaction. Thus, in order to efficiently produce the aryl carbamates by this transesterification reaction, it is preferable to remove the products from the reaction system. Since the compounds having the lowest standard boiling point in the reaction system are the alcohols formed by the transesterification reaction, the alcohols are preferably removed from the reaction system by a method such as distillative separation.

In addition, the transesterification reaction is preferably carried out with a continuous method to allow the transesterification reaction to proceed efficiently. Namely, a method is preferably used in which the carbamic acid esters and the aromatic hydroxy compounds are supplied continuously to the reaction vessel to carry out the transesterification reaction, the alcohols formed are removed from the reaction vessel in the form of the gaseous components, and reaction liquids containing the formed aryl carbamates and the aromatic hydroxy compounds are continuously removed from the bottom of the reaction vessel. In the case of carrying out the transesterification reaction according to this method, in addition to promoting the transesterification reaction, there is also the surprisingly effect of being able to improve the final yield of isocyanates by inhibiting side reactions as previously described.

Although known materials may be used for the reaction vessel and lines used to carry out the transesterification reaction provided they do not have a detrimental effect on the starting substances or reactants, SUS304, SUS316 or SUS316L and the like can be used preferably since they are inexpensive. There are no particular limitations on the type of reaction vessel, and a known tank reactor or column reactor can be used. A reaction vessel is preferably used that is provided with lines for extracting a low boiling point reaction mixture containing alcohol formed in the transesterification reaction from the reaction vessel in the form of the gaseous components, and for removing mixed liquids containing the produced aryl carbamates and aromatic hydroxy compounds from the lower portion of the reaction vessel in the form of a liquid. Various known methods are used for such a reaction vessel, examples of which include types using reaction vessels containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor, a bubble column, and types using combinations thereof. Methods using the thin film evaporator or columnar reactor are preferable from the viewpoint of efficiently shifting the equilibrium to the products side, while a structure having a large gas-liquid contact area is preferable for being able to rapidly transfer the alcohol formed to the gaseous phase.

The multistage distillation column refers to a distillation column having multiple stages in which the number of theoretical plates of distillation is 2 or more, and any multistage distillation column may be used provided it allows continuous distillation. Any multistage distillation column can be used for the multistage distillation column provided it is ordinarily used as a multistage distillation column, examples of which include tray column types using a bubble tray, a porous plate tray, a valve tray, a counter-current tray or the like, and packed column types packed with various types of packing materials such as a raschig ring, a lessing ring, a pole ring, a Berl saddle, an Interlock saddle, a Dixon packing, a McMahon packing, Helipack, a Sulzer packing, Mellapak or the like. Any packed column can be used provided the column is packed with known packing materials as described above. Moreover, a combination tray-packed column type is also used preferably that combines a tray portion with the portion packed with the packing materials. The reaction vessel is preferably provided with a line for supplying a mixture containing the carbamic acid esters and the aromatic hydroxy compounds, a line for removing the gaseous phase components containing alcohols formed by the transesterification reaction, and a line for extracting mixed liquids containing the carbamic acid esters and aromatic hydroxy compounds, and the line for removing the gaseous phase components containing the alcohols is preferably at a location that allows the gaseous phase components in the reaction vessel to be removed, and the line for extracting the mixed liquids containing the aryl carbamates and the aromatic hydroxy compounds is particularly preferably located there below.

A line for supplying inert gas and/or liquid inert solvent from the lower portion of the reaction vessel may be separately attached, and in the case the mixed liquids containing the formed aryl carbamates and the aromatic hydroxy compounds contain unreacted carbamic acid esters, a line may be attached for recirculating all or a portion of the mixed liquids to the reaction vessel. Note that in the case of using the above-mentioned inert solvent, the inert solvent may be in the form of a gas and/or a liquid.

The gaseous components containing alcohols extracted from the reaction vessel may be purified using a known method such as a distillation column, and the azeotropic and/or accompanying aromatic hydroxy compound and the like may be recycled. Equipment for warming, cooling or heating may be added to each line in consideration of clogging and the like.

<Aryl Carbamates>

The aryl carbamates preferably produced by the transesterification reaction are aryl carbamates represented by any of the following formulas (15) to (17):

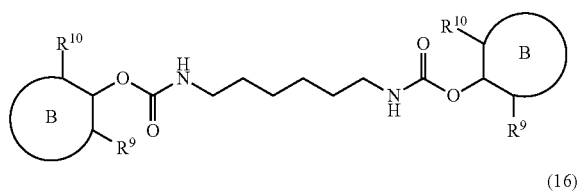

(15)

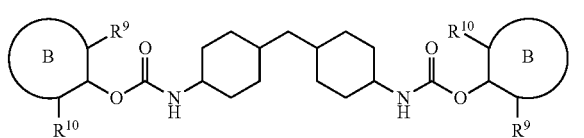

(16)

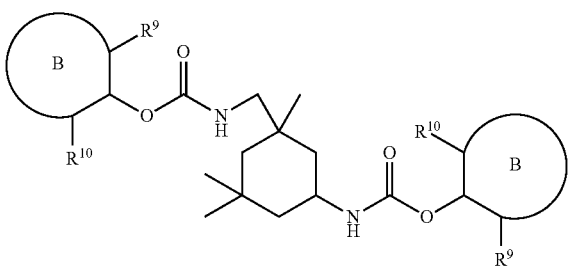

(17)

(wherein ring B represents a structure which may have a substituent and which contains at least one structure selected from the group consisting of a benzene ring, a naphthalene ring and an anthracene ring, $R^9$ represents a group other than a hydrogen atom in a form of an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the group containing an atom selected from a carbon atom, an oxygen atom and a nitrogen atom, and $R^{10}$ represents an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the aliphatic alkyl, the aliphatic alkoxy, the aryl, the aryloxy, the aralkyl and aralkyloxy groups containing an atom selected from a carbon atom, an oxygen atom and a nitrogen atoms).

Among these, more preferably produced aryl carbamates are aryl carbamates represented by any of the following formulas (18) to (20):

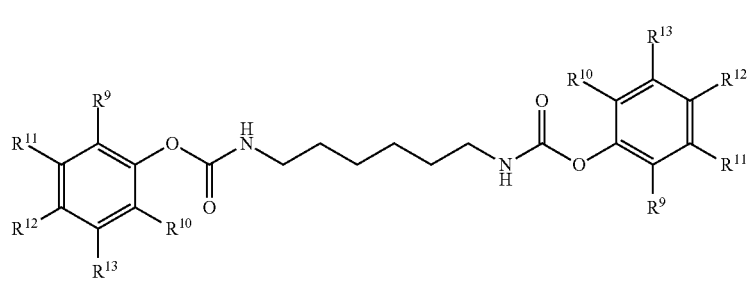

(18)

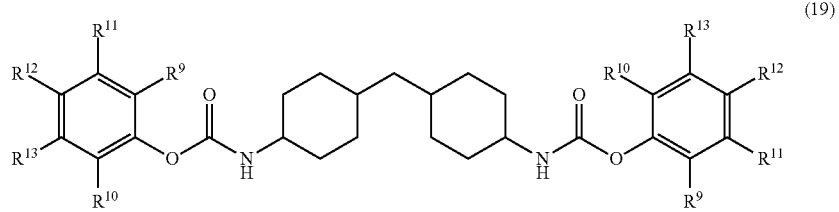

(19)

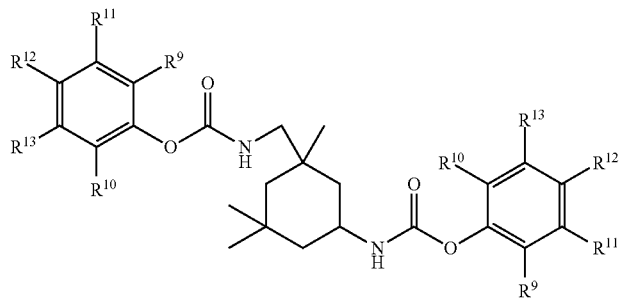

(20)

(wherein $R^9$ represents a group other than a hydrogen atom in a form of an alkyl group having 1 to 20 carbon atoms, an alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the group containing an atom selected from a carbon atom, an oxygen atom and a nitrogen atoms, and each of $R^{10}$, $R^{11}$, $R^{12}$ and $R^{13}$ independently represents a hydrogen atom or an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the aliphatic alkyl, the aliphatic alkoxy, the aryl, the aryloxy, the aralkyl, and the aralkyloxy groups containing an atom selected from a carbon atom, an oxygen atom and a nitrogen atom).

Examples of aryl polycarbamates represented by formula (18) include N,N'-hexanediyl-bis-carbamic acid bis(2-ethylphenyl)ester, N,N'-hexanediyl-bis-carbamic acid bis(2-propylphenyl)ester (isomers), N,N'-hexanediyl-bis-carbamic acid bis(2-butylphenyl)ester (isomers), N,N'-hexanediyl-bis-carbamic acid bis(2-pentylphenyl)ester (isomers), N,N'-hexanediyl-bis-carbamic acid bis(2-hexylphenyl)ester (isomers), N,N'-hexanediyl-bis-carbamic acid bis(2-octylphenyl)ester (isomers), N,N'-hexanediyl-bis-carbamic acid bis(2-cumylphenyl)ester, N,N'-hexanediyl-bis-carbamic acid bis(2,4-diethylphenyl)ester, N,N'-hexanediyl-bis-carbamic acid bis(2,4-dipropylphenyl)ester (isomers), N,N'-hexanediyl-bis-carbamic acid bis(2,4-dibutylphenyl)ester (isomers), N,N'-hexanediyl-bis-carbamic acid bis(2,4-dipentylphenyl)ester (isomers), N,N'-hexanediyl-bis-carbamic acid bis(2,4-dihexylphenyl)ester (isomers), N,N'-hexanediyl-bis-carbamic acid bis(2,4-dioctylphenyl)ester (isomers), N,N'-hexanediyl-bis-carbamic acid bis(2,4-dicumylphenyl)ester (isomers), N,N'-hexanediyl-bis-carbamic acid bis(2,6-dimethylphenyl)ester, N,N'-hexanediyl-bis-carbamic acid bis(2,6-diethylphenyl)ester (isomers), N,N'-hexanediyl-bis-carbamic acid bis(2,6-dipropylphenyl)ester (isomers), N,N'-hexanediyl-bis-carbamic acid bis(2,4,6-trimethylphenyl)ester, N,N'-hexanediyl-bis-carbamic acid bis(2,3,6-trimethylphenyl)ester, N,N'-hexanediyl-bis-carbamic acid bis(2,4,6-triethylphenyl)ester, and N,N'-hexanediyl-bis-carbamic acid bis(2,4,6-tripropylphenyl)ester (isomers). In addition, examples of alkyl polycarbamates represented by formula (19) include bis(2-ethylphenyl)-4,4'-methylene-dicyclohexyl carbamate, bis(2-propylphenyl)-4,4'-methylene-dicyclohexyl carbamate (isomers), bis(2-butylphenyl)-4,4'-methylene-dicyclohexyl carbamate (isomers), bis(2-pentylphenyl)-4,4'-methylene-dicyclohexyl carbamate (isomers), bis(2-hexylphenyl)-4,4'-methylene-dicyclohexyl carbamate (isomers), bis(2-heptylphenyl)-4,4'-methylene-dicyclohexyl carbamate (isomers), bis(2-octylphenyl)-4,4'-methylene-dicyclohexyl carbamate (isomers), bis(2-cumylphenyl)-4,4'-methylene-dicyclohexyl carbamate (isomers), bis(2,4-diethylphenyl)-4,4'-methylene-dicyclohexyl carbamate, bis(2,4-dipropylphenyl)-4,4'-methylene-dicyclohexyl carbamate (isomers), bis(2,4-dibutylphenyl)-4,4'-methylene-dicyclohexyl carbamate (isomers), bis(2,4-dipentylphenyl)-4,4'-methylene-dicyclohexyl carbamate (isomers), bis(2,4-dihexylphenyl)-4,4'-methylene-dicyclohexyl carbamate (isomers), bis(2,4-diheptylphenyl)-4,4'-methylene-dicyclohexyl carbamate (isomers), bis(2,4-dioctylphenyl)-4,4'-methylene-dicyclohexyl carbamate (isomers), bis(2,4-dicumylphenyl)-4,4'-methylene-dicyclohexyl carbamate, bis(2,6-dimethylphenyl)-4,4'-methylene-dicyclohexyl carbamate (isomers), bis(2,6-diethylphenyl)-4,4'-methylene-dicyclohexyl carbamate (isomers), bis(2,6-dipropylphenyl)-4,4'-methylene-dicyclohexyl carbamate (isomers), bis(2,4,6-trimethylphenyl)-4,4'-methylene-dicyclohexyl carbamate (isomers), bis(2,4,6-triethylphenyl)-4,4'-methylene-dicyclohexyl carbamate (isomers) and bis(2,4,6-tripropylphenyl)-4,4'-methylene-dicyclohexyl carbamate (isomers). Moreover, examples of alkyl polycarbamates represented by formula (20) include 3-((2-ethyl phenoxy)carbonylamino-methyl)-3,5,5-trimethylcyclohexyl carbamic acid (2-ethylphenyl)ester, 3-((2-propylphenoxy)carbonylamino-methyl)-3,5,5-trimethylcyclohexyl carbamic acid (2-propylphenyl)ester (isomers), 3-((2-butylphenoxy)carbonylamino-methyl)-3,5,5-trimethylcyclohexyl carbamic acid (2-butylphenyl)ester (isomers), 3-((2-pentylphenoxy)carbonylamino-methyl)-3,5,5-trimethylcyclohexyl carbamic acid (2-pentylphenyl)ester (isomers), 3-((2-hexylphenoxy)carbonylamino-methyl)-3,5,5-trimethylcyclohexyl carbamic acid (2-hexylphenyl)ester (isomers), 3-((2-heptylphenoxy)carbonylamino-methyl)-3,5,5-trimethylcyclohexyl carbamic acid (2-heptylphenyl)ester (isomers), 3-((2-octylphenoxy)carbonylamino-methyl)-3,5,5-trimethylcyclohexyl carbamic acid (2-octylphenyl)ester (isomers), 3-((2-cumylphenoxy)carbonylamino-methyl)-3,5,5-trimethylcyclohexyl carbamic acid (2-cumylphenyl)ester (isomers), 3-((2,4-diethylphenoxy)carbonylamino-methyl)-3,5,5-trimethylcyclohexyl carbamic acid (2,4-diethylphenyl)ester, 3-((2,4-dipropylphenoxy)carbonylamino-methyl)-3,5,5-trimethylcyclohexyl carbamic acid (2,4-dipropylphenyl)ester (isomers), 3-((2,4-dibutylphenoxy)carbonylamino-methyl)-3,5,5-trimethylcyclohexyl carbamic acid (2,4-dibutylphenyl)ester (isomers), 3-((2,4-dipentylphenoxy)carbonylamino-methyl)-3,5,5-trimethylcyclohexyl carbamic acid (2,4-dipentylphenyl)ester (isomers), 3-((2,4-dihexylphenoxy)carbonylamino-methyl)-3,5,5-trimethylcyclohexyl carbamic acid (2,4-dihexylphenyl)ester (isomers), 3-((2,4-diheptylphenoxy)carbonylamino-methyl)-3,5,5-trimethylcyclohexyl carbamic acid (2,4-diheptylphenyl)ester (isomers), 3-((2,4-dioctylphenoxy)carbonylamino-methyl)-3,5,5-trimethylcyclohexyl carbamic acid (2,4-dioctylphenyl)ester (isomers), 3-((2,4-dicumylphenoxy)carbonylamino-methyl)-3,5,5-trimethylcyclohexyl carbamic acid (2,4-dicumylphenyl)ester, 3-((2,6-dimethylphenoxy)carbonylamino-methyl)-3,5,5-trimethylcyclohexyl carbamic acid (2,6-dimethylphenyl)ester, 3-((2,6-diethylphenoxy)carbonylamino-methyl)-3,5,5-trimethylcyclohexyl carbamic acid (2,6-diethylphenyl)ester, 3-((2,6-dipropylphenoxy)carbonylamino-methyl)-3,5,5-trimethylcyclohexyl carbamic acid (2,6-dipropylphenyl)ester (isomers), 3-((2,4,6-trimethylphenoxy)carbonylamino-methyl)-3,5,5-trimethylcyclohexyl carbamic acid (2,4,6-trimethylphenyl)ester, 3-((2,4,6-triethylphenoxy)carbonylamino-methyl)-3,5,5-trimethylcyclohexyl carbamic acid (2,4,6-triethylphenyl)ester, and 3-((2,4,6-tripropylphenoxy)carbonylamino-methyl)-3,5,5-trimethylcyclohexyl carbamic acid (2,4,6-tripropylphenyl)ester (isomers).

The aryl carbamates produced in the transesterification reaction may be subjected to the subsequent thermal decomposition reaction while still as a mixed liquid containing aryl carbamates and aromatic hydroxy compounds which are removed from the reactor, or the aryl carbamates may be subjected to the thermal decomposition reaction after purifying from the mixed liquid. A known method can be used to purify the aryl carbamate from the reaction liquid, examples of which include removal of the aromatic hydroxy compounds by distillation, washing with solvents and purification of the aryl carbamates by crystallization.

Since the aryl carbamates of the present embodiment are carbamic acid esters composed of aromatic hydroxy compounds and isocyanates, the thermal decomposition temperature is low as is generally known. In addition, the aryl carbamates of the present embodiment are surprisingly extremely resistant to the occurrence of side reactions (such as a reaction resulting in the formation of a urea bond as previously described) at high temperatures (such as 180° C.) at which thermal decomposition is carried out. Although the mechanism by which side reactions are inhibited is unclear, as was previously described, it is presumed that a substituent at the ortho position relative to the hydroxyl group sterically protects a urethane bond, thereby hindering the reaction between a different carbamic acid ester and the urethane bond.

Moreover, although the aromatic hydroxy compounds formed by the thermal decomposition reaction of the aryl carbamates of the present embodiment are aromatic hydroxy compounds having a substituent at the ortho position relative to a hydroxyl group, since the reaction rate between the aromatic hydroxy compounds and isocyanates are surprisingly late, namely the reverse reaction rate in the thermal decomposition reaction is slow, when carrying out the thermal decomposition reaction on the aryl carbamates, there is the advantage of being able to easily separate the aromatic hydroxy compounds and the isocyanates.

<Thermal Decomposition Reaction of Aryl Carbamates>

The following provides an explanation of the aryl carbamate decomposition reaction of the present embodiment.

The decomposition reaction of the present embodiment is a thermal decomposition reaction by which corresponding isocyanates and aromatic hydroxy compounds are formed from the aryl carbamates.

The reaction temperature is generally within the range of from 100 to 300° C., and although a high temperature is preferable for increasing the reaction rate, since side reactions as described above may be conversely caused by the aryl carbamates and/or the reaction products in the form of the isocyanates, the reaction temperature is preferably within the range of from 150 to 250° C. A known cooling apparatus or heating apparatus may be installed in the reaction vessel to maintain a constant reaction temperature. In addition, although varying according to the types of compounds used and reaction temperature, the reaction pressure may be decreased pressure, normal pressure or increased pressure, and the reaction is normally carried out at a pressure within the range of from 20 to $1 \times 10^6$ Pa. There are no particular limitations on the reaction time (residence time in the case of a continuous method) and is generally from 0.001 to 100 hours, preferably from 0.01 to 50 hours and more preferably from 0.1 to 30 hours. A catalyst can be used in the present embodiment, and the catalyst is used at from 0.01 to 30% by weight and preferably at from 0.5 to 20% by weight based on the weight of the aryl carbamates. For example, organic metal catalysts such as dibutyl tin dilaurate, ferrous octoate, stannous octoate or the like, or amines such as 1,4-diazabicyclo[2,2,2]octane, triethylenediamine, triethylamine or the like are suitable for use as catalysts, while organic metal catalysts such as dibutyl tin dilaurate, ferrous octoate, stannous octoate or the like are particularly preferable. These compounds may be used alone or two or more types may be used as a mixture. In the case of using the catalysts in the above-mentioned transesterification reaction, the catalysts contained in the mixed liquid following the transesterification reaction may be used as a catalyst in the thermal decomposition reaction or catalysts may be freshly added to the aryl carbamates when the thermal decomposition reaction is carried out. Although the use of a reaction solvent is not necessarily required in the present embodiment, a suitable inert solvent can be used as a reaction solvent for the purpose of facilitating the reaction procedure, examples of which include alkanes such as hexane (isomers), heptane (isomers), octane (isomers), nonane (isomers), decane (isomers) or the like; aromatic hydrocarbons and alkyl-substituted aromatic hydrocarbons such as benzene, toluene, xylene (isomers), ethyl benzene, diisopropyl benzene (isomers), dibutyl benzene (isomers), naphthalene or the like; aromatic compounds substituted with a halogen or nitro group such as chlorobenzene, dichlorobenzene (isomers), bromobenzene, dibromobenzene (isomers), chloronaphthalene, bromonaphthalene, nitrobenzene, nitronaphthalene or the like; polycyclic hydrocarbon compounds such as diphenyl, substituted diphenyl, diphenyl methane, terphenyl, anthracene, dibenzyl toluene (isomers) or the like; aliphatic hydrocarbons such as cyclohexane, cyclopentane, cyclooctane, ethylcyclohexane or the like; ketones such as methyl ethyl ketone, acetophenone or the like; esters such as dibutyl phthalate, dihexyl phthalate, dioctyl phthalate, benzylbutyl phthalate or the like; ethers and thioethers such as diphenyl ether, diphenyl sulfide or the like; and sulfoxides such as dimethylsulfoxide, diphenylsulfoxide or the like; and, silicone oil. These solvents can be used alone or two or more types can be used as a mixture.

As was previously described, although the thermal decomposition reaction of the present embodiment is a reaction by which the corresponding isocyanates and the aromatic hydroxy compounds are formed from the aryl carbamates, the thermal decomposition reaction is an equilibrium reaction. Thus, in order to efficiently obtain isocyanates in this thermal decomposition reaction, it is preferable to remove at least one of the products of this thermal decomposition reaction in the form of the isocyanates and the aromatic hydroxy compounds from the thermal decomposition reaction system in the form of a gaseous component by a method such as distillation.

Whether the isocyanates or aromatic hydroxy compounds are removed as the gaseous components can be arbitrarily determined according to the compounds used, and for example, the respective standard boiling points of the isocyanates and the aromatic hydroxy compounds are compared followed by removing the compounds having the lower standard boiling point in the form of the gaseous components.

The aryl carbamates are also susceptible to the occurrence of side reactions as described above in the case of being held at a high temperature for a long period of time, although to a much lower degree than carbamic acid esters. In addition, the above-mentioned side reactions may also be induced by the isocyanates formed by the thermal decomposition reaction. Thus, the time during which the aryl carbamates and the isocyanates are held at a high temperature is preferably as short as possible, and the thermal decomposition reaction is preferably carried out by the continuous method. The continuous method refers to a method in which the aryl carbamates are continuously supplied to a reaction vessel where it is subjected to a thermal decomposition reaction, and at least either the formed isocyanates or aromatic hydroxy compounds are removed from the reaction vessel in the form of a gaseous component.

Although known materials may be used for the reaction vessel and lines used to carry out the thermal decomposition reaction provided they do not have a detrimental effect on the aryl carbamate or the products in the form of the aromatic hydroxy compounds and isocyanates, SUS304, SUS316 or SUS316L and the like can be used preferably since they are inexpensive. There are no particular limitations on the type of reaction vessel, and a known tank reactor or column reactor can be used. A reaction vessel is preferably used that is provided with lines for extracting a low boiling point mixture containing at least either the isocyanates or aromatic hydroxy compounds formed in the thermal decomposition reaction from the reaction vessel in the form of the gaseous components, and for removing mixed liquids containing unreacted aryl carbamates and the compounds not extracted in the form of the gaseous components from the lower portion of the reaction vessel. Various known methods are used for such reaction vessels, examples of which include types using reaction vessels containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using the thin film evaporator or columnar reactor are preferable from the viewpoint of rapidly removing low boiling point components from the reaction system, while a structure having a large gas-liquid contact area is preferable for rapidly transferring the low boiling point components formed to the gaseous phase.

The reaction vessel is preferably provided with a line for supplying the aryl carbamates, a line for removing a gaseous component containing at least either the isocyanates or aromatic hydroxy compounds formed by the thermal decomposition reaction, and a line for removing a mixed liquid containing the compounds not removed as a gaseous component and unreacted aryl carbamates, the line for removing the gaseous components containing at least either the isocyanates or aromatic hydroxy compounds is preferably located at a location that allows the gaseous components in the reaction vessel to be removed, and the line for extracting the mixed liquids containing the compounds not removed as the gaseous components and the unreacted aryl carbamates is particularly preferably located there below.

In addition, a line for supplying inert gas and/or liquid inert solvent from the lower portion of the reaction vessel may be separately attached, and a line may also be attached for recirculating all or a portion of the mixed liquid containing the unreacted aryl carbamates and the compounds not removed as the gaseous components to the reaction vessel. Equipment for warming, cooling or heating may be added to each line in consideration of clogging and the like. Furthermore, in the case of using the above-mentioned inert solvent, the inert solvent may be in the form of a gas and/or a liquid.

The isocyanate obtained by the above-mentioned production process can be preferably used as a production raw material of polyurethane foam, paints, adhesives and the like. Since this process enables isocyanates to be efficiently produced without using extremely toxic phosgene, the present invention is industrially extremely significant.

EXAMPLES

Although the following provides a detailed explanation of the present invention based on examples thereof, the scope of the present invention is not limited by these examples.
<Analytical Methods>
1) NMR Analysis
  Apparatus: JNM-A400 FT-NMR system, JEOL Ltd., Japan
(1) Preparation of $^1$H and $^{13}$C-NMR Analysis Samples
  About 0.3 g of sample solution were weighed followed by the addition of about 0.7 g of heavy chloroform (99.8%, Aldrich Corp., USA) and about 0.05 g of internal standard in the form of tetramethyl tin (guaranteed reagent, Wako Pure Chemical Industries, Ltd., Japan) and mixing to uniformity to obtain solutions used as NMR analysis samples.
(2) Quantitative Analysis
  Analyses were performed for each standard and quantitative analyses were performed on the analysis sample solutions based on the resulting calibration curve.
2) Liquid Chromatography
  Apparatus: LC-10AT system, Shimadzu Corp., Japan
  Column: Silica-60 column, Tosoh Corp., Japan, two columns connected in series
  Developing solvent: Mixed liquid of hexane/tetrahydrofuran (80/20) (v/v)
  Solvent flow rate: 2 mL/min
  Column temperature: 35° C.
  Detector: R.I. (refractometer)
(1) Liquid Chromatography Analysis Samples
  About 0.1 g of sample were weighed followed by the addition of about 1 g of tetrahydrofuran (dehydrated, Wako Pure Chemical Industries, Ltd., Japan) and about 0.02 g of internal standard in the form of bisphenol A (guaranteed reagent, Wako Pure Chemical Industries, Ltd., Japan) and mixing to uniformity to obtain solutions used as liquid chromatography analysis samples.
(2) Quantitative Analysis
  Analyses were performed for each standard and quantitative analyses were performed on the analysis sample solutions based on the resulting calibration curve.
3) Gas Chromatography
  Apparatus: GC-2010, Shimadzu Corp., Japan
  Column: DB-1 column, Agilent Technologies Corp., USA, length: 30 m, inner diameter: 0.250 mm, film thickness: 1.00 µm Column temperature: Held at 50° C. for 5 minutes followed by increasing at the rate of 10° C./min to 200° C.; held at 200° C. for 5 minutes followed by increasing at the rate of 10° C./min to 300° C.

Detector: FID (1) Gas Chromatography Analysis Samples

About 0.05 g of sample were weighed followed by the addition of about 1 g of acetone (dehydrated, Wako Pure Chemical Industries, Ltd., Japan) and about 0.02 g of internal standard in the form of toluene (dehydrated, Wako Pure Chemical Industries, Ltd., Japan) and mixing to uniformity to obtain solutions used as gas chromatography analysis samples.

(2) Quantitative Analysis

Analyses were performed for each standard and quantitative analyses were performed on the analysis sample solutions based on the resulting calibration curve.

Reference Example 1

Production of Bis(3-methylbutyl)Carbonate

Step (I-1): Production of Dialkyl Tin Catalyst 625 g (2.7 mol) of di-n-butyl tin oxide (Sankyo Organic Chemicals Co., Ltd., Japan) and 2020 g (22.7 mol) of 3-methyl-1-butanol (Kuraray Co., Ltd., Japan) were placed in a 5000 mL volumetric pear-shaped flask. The flask was connected to an evaporator (R-144, Shibata Co., Ltd., Japan) to which was connected an oil bath (OBH-24, Masuda Corp., Japan) equipped with a temperature controller, a vacuum pump (G-50A, Ulvac Inc., Japan) and a vacuum controller (VC-10S, Okano Seisakusho Co., Ltd., Japan). The purge valve outlet of this evaporator was connected to a line containing nitrogen gas flowing at a normal pressure. After closing the purge valve of the evaporator to reduce pressure inside the system, the purge valve was opened gradually to allow nitrogen to flow into the system and return to normal pressure. The oil bath temperature was set to about 145° C., the flask was immersed in the oil bath and rotation of the evaporator was started. After heating for about 40 minutes in the presence of atmospheric pressure nitrogen with the purge valve of the evaporator left open, distillation of 3-methyl-1-butanol containing water began. After maintaining in this state for 7 hours, the purge valve was closed, pressure inside the system was gradually reduced, and excess 3-methyl-1-butanol was distilled with the pressure inside the system at 74 to 35 kPa. After the fraction no longer appeared, the flask was taken out of the oil bath. After allowing the flask to cool to the vicinity of room temperature (25° C.), the flask was taken out of the oil bath, the purge valve was opened gradually and the pressure inside the system was returned to atmospheric pressure. 1173 g of reaction liquid were obtained in the flask. Based on the results of $^{119}$Sn-, $^1$H- and $^{13}$C-NMR analyses, 1,1,3,3-tetra-n-butyl-1,3-bis(3-methylbutyloxy) distannoxane was confirmed to have been obtained at a yield of 99% based on di-n-butyl tin oxide. The same procedure was then repeated 12 times to obtain a total of 10335 g of 1,1,3,3-tetra-n-butyl-1,3-bis(3-methylbutyloxy) distannoxane.

Step (I-2): Production of Bis(3-methylbutyl)Carbonate

Figure 1:
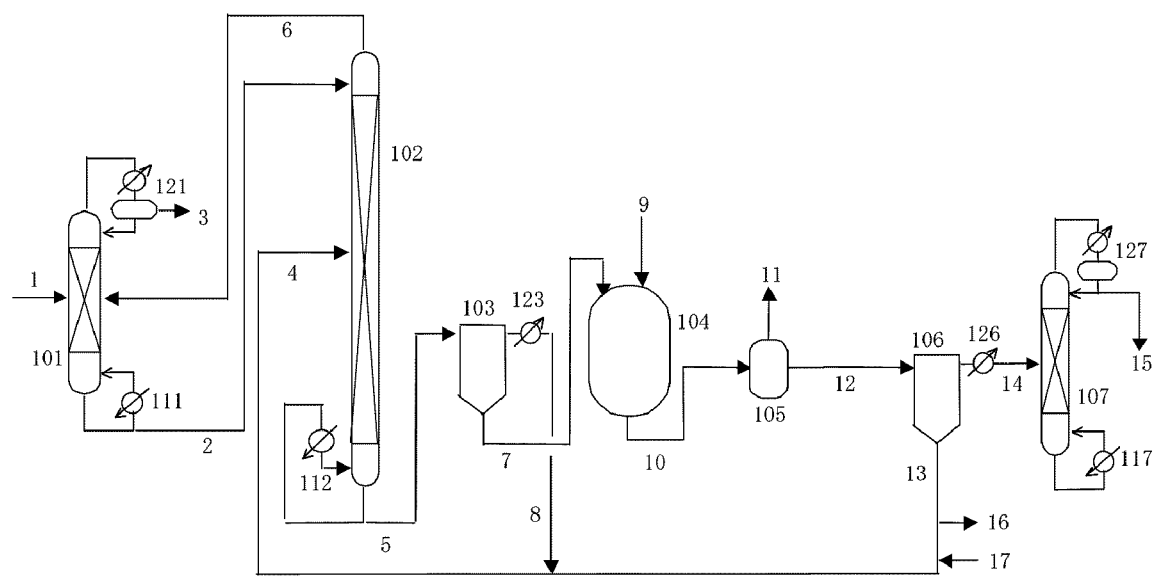
FIG. 1 shows a conceptual drawing showing a continuous production apparatus for producing carbonic acid ester according to an embodiment of the present invention.

Bis(3-methylbutyl)carbonate was produced in a continuous production apparatus like that shown in FIG. 1. 1,1,3,3-tetrabutyl-1,3-bis(3-methylbutyloxy) distannoxane produced in the manner described above was supplied at the rate of 4388 g/hr from a transfer line 4 into a column-type reaction vessel 102 packed with Metal Gauze CY Packing (Sulzer Chemtech Ltd., Switzerland) and having an inner diameter of 151 mm and effective length of 5040 mm, and 3-methyl-1-butanol purified with a distillation column 101 was supplied at the rate of 14953 g/hr from a transfer line 2. The liquid temperature inside reaction vessel 102 was controlled to 160° C. by a heater and a reboiler 112, and the pressure was adjusted to about 120 kPa-G with a pressure control valve. The residence time in the reaction vessel was about 17 minutes. 3-Methyl-1-butanol containing water at the rate of 15037 g/hr from the top of the reaction vessel via a transfer line 6, and 3-methyl-1-butanol at the rate of 825 g/hr via feed line 1, were pumped to distillation column 101 packed with Metal Gauze CY Packing and provided with a reboiler 111 and a condenser 121 to carry out distillative purification. In the top of distillation column 101, a fraction containing a high concentration of water was condensed by condenser 121 and recovered from a recovery line 3. Purified 3-methyl-1-butanol was pumped to column-type reaction vessel 102 via transfer line 2 located in the bottom of distillation column 101. An alkyl tin alkoxide catalyst composition containing di-n-butyl-bis(3-methylbutyloxy) tin and 1,1,3,3-tetra-n-butyl-1,3-bis(3-methylbutyloxy) distannoxane was obtained from the bottom of column-type reaction vessel 102, and supplied to a thin film evaporator 103 (Kobelco Eco-Solutions Co., Ltd., Japan) via a transfer line 5. The 3-methyl-1-butanol was distilled off in thin film evaporator 103 and returned to column-type reaction vessel 102 via a condenser 123, a transfer line 8 and transfer line 4. The alkyl tin alkoxide catalyst composition was pumped from the bottom of thin film evaporator 103 via a transfer line 7 and supplied to an autoclave 104 while adjusting the flow rate of di-n-butyl-bis(3-methylbutyloxy) tin and 1,1,3,3-tetra-n-butyl-1,3-bis(3-methylbutyloxy) distannoxane to about 5130 g/hr. Carbon dioxide was supplied to the autoclave by a transfer line 9 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the alkyl tin alkoxide catalyst composition was carried out to obtain a reaction liquid containing bis(3-methylbutyl)carbonate. This reaction liquid was transferred to a decarbonization tank 105 via a transfer line 10 and a control valve to remove residual carbon dioxide, and the carbon dioxide was recovered from a transfer line 11. Subsequently, the reaction liquid was transferred to a thin film evaporator (Kobelco Eco-Solutions Co., Ltd., Japan) 106 set to about 142° C. and about 0.5 kPa via a transfer line 12 and supplied while adjusting the flow rate of 1,1,3,3-tetra-n-butyl-1,3-bis(3-methylbutyloxy) distannoxane to about 4388 g/hr to obtain a fraction containing bis(3-methylbutyl)carbonate. On the other hand, the evaporation residue was circulated to column-type reaction vessel 102 via transfer line 13 and transfer line 4 while adjusting the flow rate of 1,1,3,3-tetra-n-butyl-1,3-bis(3-methylbutyloxy) distannoxane to about 4388 g/hr. The fraction containing bis(3-methylbutyl) carbonate was supplied to a distillation column 107 packed with Metal Gauze CY packing and equipped with a reboiler 117 and a condenser 127 via a condenser 126 and a transfer line 14 at the rate of 959 g/hr followed by distillative purification to obtain 99 wt % bis(3-methylbutyl)carbonate from a recovery line 16 at the rate of 944 g/hr. When the alkyl tin alkoxide catalyst composition of a transfer line 13 was analyzed by $^{119}$Sn-, $^1$H- and $^{13}$C-NMR analysis, it was found to contain 1,1,3,3-tetra-n-butyl-1,3-bis(3-methylbutyloxy) distannoxane but not contain di-n-butyl-bis(3-methylbutyloxy) tin. After carrying out the above-mentioned continuous operation for about 240 hours, alkyl tin alkoxide catalyst composition was extracted from an extraction line 16 at the rate of 18 g/hr, while 1,1,3,3-tetra-n-butyl-1,3-bis(3-methyl-butyloxy) distannoxane produced according to the above process was supplied from a feed line 17 at the rate of 18 g/hr.

Reference Example 2

Production of Dibutyl Carbonate

Step (II-1): Production of Dialkyl Tin Catalyst 692 g (2.78 mol) of di-n-butyl tin oxide and 2000 g (27 mol) of 1-butanol (Wako Pure Chemical Industries, Ltd., Japan) were placed in a 3000 mL volumetric pear-shaped flask. The flask containing the white, slurry-like mixture was attached to an evaporator to which was connected an oil bath equipped with a temperature controller, a vacuum pump and a vacuum controller. The purge valve outlet of this evaporator was connected to a line containing nitrogen gas flowing at normal pressure. After closing the purge valve of the evaporator to reduce pressure inside the system, the purge valve was opened gradually to allow nitrogen to flow into the system and return to normal pressure. The oil bath temperature was set to about 126° C., the flask was immersed in the oil bath and rotation of the evaporator was started. After rotating and heating for about 30 minutes at normal pressure with the purge valve of the evaporator left open, the mixture boiled and distillation of the low boiling point component began. After maintaining in this state for 8 hours, the purge valve was closed, pressure inside the system was gradually reduced, and residual low boiling point component was distilled off with the pressure inside the system at 76 to 54 kPa. After the low boiling point component no longer appeared, the flask was taken out of the oil bath. The reaction liquid was in the form of a clear liquid. The flask was subsequently taken out of the oil bath, the purge valve was opened gradually and the pressure inside the system was returned to normal pressure. 952 g of reaction liquid were obtained in the flask. Based on the results of $^{119}$Sn-, $^{1}$H- and $^{13}$C-NMR analyses, a product in the form of 1,1,3,3-tetra-n-butyl-1,3-di(n-butyloxy) distannoxane was obtained at a yield of 99% based on di-n-butyl tin oxide. The same procedure was then repeated 12 times to obtain a total of 11480 g of 1,1,3,3-tetra-n-butyl-1,3-di(butyloxy) distannoxane.

Step (II-2): Production of Dibutyl Carbonate

Carbonic acid ester was produced in a continuous production apparatus like that shown in FIG. 1. 1,1,3,3-Tetra-n-butyl-1,3-di(n-butyloxy) distannoxane produced in step (II-1) was supplied at the rate of 4201 g/hr from transfer line 4 into a column-type reaction vessel packed with Mellapak 750Y packing (Sulzer Chemtech Ltd., Switzerland) and having an inner diameter of 151 mm and effective length of 5040 mm, and 1-butanol purified with distillation column 101 was supplied to column-type reaction vessel 102 at the rate of 24717 g/hr from feed line 2. The liquid temperature inside the reaction vessel was controlled to 160° C. by a heater and reboiler 112, and the pressure was adjusted to about 250 kPa-G with a pressure control valve. The residence time in the reaction vessel was about 10 minutes. 1-Butanol containing water at the rate of 24715 g/hr from the top of the reaction vessel via transfer line 6, and 1-butanol at the rate of 824 g/hr via feed line 1, were pumped to distillation column 101 packed with Metal Gauze CY packing (Sulzer Chemtech Ltd., Switzerland) and provided with reboiler 111 and condenser 121 to carry out distillative purification. In the top of distillation column 101, a fraction containing a high concentration of water was condensed by condenser 121 and recovered from transfer line 3. Purified 1-butanol was pumped via transfer line 2 located in the bottom of distillation column 101. An alkyl tin alkoxide catalyst composition containing di-n-butyl tin di-n-butoxide and 1,1,3,3-tetra-n-butyl-1,3-di(n-butyloxy) distannoxane was obtained from the bottom of column-type reaction vessel 102, and supplied to thin film evaporator 103 (Kobelco Eco-Solutions Co., Ltd., Japan) via a transfer line 5. The 1-butanol was distilled off in thin film evaporator 103 and returned to column-type reaction vessel 102 via condenser 123, transfer line 8 and transfer line 4. The alkyl tin alkoxide catalyst composition was pumped from the bottom of thin film evaporator 103 via transfer line 7 and supplied to autoclave 104 while adjusting the flow rate of the active components in the form of dibutyl tin dibutoxide and 1,1,3,3-tetra-n-butyl-1,3-di(n-butyloxy) distannoxane to about 4812 g/hr. Carbon dioxide was supplied to the autoclave by feed line 9 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the alkyl tin alkoxide catalyst composition was carried out to obtain a reaction liquid containing dibutyl carbonate. This reaction liquid was transferred to decarbonization tank 105 via transfer line 10 and a control valve to remove residual carbon dioxide, and the carbon dioxide was recovered from transfer line 11. Subsequently, the reaction liquid was pumped to thin film evaporator 106 (Kobelco Eco-Solutions Co., Ltd., Japan) set to about 140° C. and about 1.4 kPa via transfer line 12 and supplied while adjusting the flow rate of the 1,1,3,3-tetra-n-butyl-1,3-di(n-butyloxy) distannoxane to about 4201 g/hr to obtain a fraction containing dibutyl carbonate. On the other hand, the evaporation residue was circulated to column-type reaction vessel 102 via transfer line 13 and transfer line 4 while adjusting the flow rate of 1,1,3,3-tetra-n-butyl-1,3-di(n-butyloxy) distannoxane to about 4201 g/hr. The fraction containing dibutyl carbonate was supplied to distillation column 107 packed with Metal Gauze CY packing (Sulzer Chemtech Ltd., Switzerland) and equipped with reboiler 117 and condenser 127 via condenser 126 and a transfer line 14 at the rate of 830 g/hr followed by distillative purification to obtain 99 wt % bis(3-methylbutyl) carbonate from recovery line 16 at the rate of 814 g/hr. When the alkyl tin alkoxide catalyst composition of transfer line 13 was analyzed by $^{119}$Sn-, $^{1}$H- and $^{13}$C-NMR analysis, it was found to contain 1,1,3,3-tetra-n-butyl-1,3-di(n-butyloxy) distannoxane but not contain di-n-butyl tin di-n-butoxide. After carrying out the above-mentioned continuous operation for about 600 hours, alkyl tin alkoxide catalyst composition was extracted from extraction line 16 at the rate of 16 g/hr, while 1,1,3,3-tetra-n-butyl-1,3-di(n-butyloxy) distannoxane produced in step (II-1) was supplied from feed line 17 at the rate of 16 g/hr.

Example 1

Step (1-1): Production of N,N'-hexanediyl-bis-carbamic Acid Di(3-methylbutyl)Ester 1818 g (9.0 mol) of bis(3-methylbutyl)carbonate and 208.8 g (1.8 mol) of hexamethylene diamine (Aldrich Corp., USA) were placed in a 5 L volumetric fourth-mouth flask, a stirrer was placed in the flask, and a Dimroth condenser and three-way valve were attached to the flask. After replacing the inside of the system with nitrogen, the four-mouth flask was immersed in an oil bath (OBH-24, Masuda Corp., Japan) heated to 80° C. followed by the addition of 3.5 g of sodium methoxide (28% methanol solution, Wako Pure Chemical Industries, Ltd., Japan) to start the reaction. Samples of the reaction liquid were suitably collected and subjected to NMR analysis, and the reaction was terminated at the point hexamethylene diamine was no longer detected. As a result of analyzing the resulting solution by liquid chromatography, the solution was found to contain 29.9% by weight of N,N'-hexanediyl-bis-carbamic acid di(3-methylbutyl)ester.

Step (1-2): Distillation of Low Boiling Point Component

The solution obtained in step (1-1) was placed in a 5 L volumetric flask equipped with a three-way valve, condenser, distillate collector and thermometer, and the inside of the flask was replaced with nitrogen in a vacuum. The flask was immersed in an oil bath heated to about 130° C. Distillation was carried out while gradually reducing the pressure in the flask to a final pressure of 0.02 kPa. 1410 g of distillate were obtained. As a result of analyzing by gas chromatography, the distillate was found to be a solution containing 78.3% by weight of bis(3-methylbutyl)carbonate and 21.4% by weight of isoamyl alcohol. In addition, as a result of analyzing the resulting distillation residue in the flask by liquid chromatography, the distillation residue was found contain 98.0% by weight of N,N'-hexanediyl-bis-carbamic acid di(3-methylbutyl)ester.

Step (1-3): Production of N,N'-hexanediyl-bis-carbamic Acid Di(2,4-di-tert-amylphenyl)Ester by Transesterification A transesterification reaction was carried out in a reaction apparatus like that shown in FIG. 2.

111 g of dibutyl tin dilaurate (chemical grade, Wako Pure Chemical Industries, Ltd., Japan) and 4119 g of 2,4-di-tert-amylphenol (Tokyo Chemical Industry Co., Ltd., Japan) were added to 618 g of the distillation residue obtained in step (1-2) and stirred to obtain a homogeneous solution which was then placed in a feed tank 201. A thin film distillation apparatus 202 (Kobelco Eco-Solutions Co., Ltd., Japan) having heat-conducting surface area of 0.2 m² was heated to 240° C., and the inside of the thin film distillation apparatus was replaced with a nitrogen atmosphere at atmospheric pressure. The solution was supplied to the thin film distillation apparatus via supply line 21 at the rate of about 1200 g/hr. A mixed gas containing 3-methyl-1-butanol and 2,4-di-tert-amylphenol was extracted from a line 25 provided in the upper portion of the thin film distillation apparatus 202, and supplied to a distillation column 203 packed with Metal Gauze CY Packing (Sulzer Chemtech Ltd., Switzerland). The 3-methyl-1-butanol and 2,4-di-tert-amylphenol were separated in the distillation column 203, and the 2,4-di-tert-amylphenol was returned to the upper portion of thin film distillation apparatus 202 by a line 26 provided in the bottom of distillation column 203. The reaction liquid was extracted from a line 22 provided in the bottom of thin film distillation apparatus 202 and returned to feed tank 201 via a line 23.

After carrying out this step for 62 hours, the reaction liquid was extracted from a line 24. 4532 g of extracted liquid were extracted, and 304 g of solution were recovered from a line 27 provided in the upper portion of distillation column 203.

As a result of analyzing the extracted reaction liquid by liquid chromatography, the reaction liquid was found to contain 24.2% by weight of N,N'-hexanediyl-bis-carbamic acid di(2,4-di-tert-amylphenyl) ester. In addition, as a result of analyzing the solution recovered from line 27 by $^1$H- and $^{13}$C-NMR analysis, the solution was found to contain 98% by weight of 3-methyl-1-butanol.

Step (1-4): Production of Hexamethylene Diisocyanate by Thermal Decomposition of N,N'-hexanediyl-bis-carbamic Acid Di(2,4-di-tert-amylphenyl)Ester A thermal decomposition reaction was carried out in a reaction apparatus like that shown in FIG. 2.

A thin film distillation apparatus 302 (Kobelco Eco-Solutions Co., Ltd., Japan) having a heat-conducting surface area of 0.2 m² was heated to 200° C. and the pressure within the thin film distillation apparatus was set to about 1.3 kPa. The solution obtained in step (1-3) was placed in a feed tank 301 and supplied to the thin film distillation apparatus at the rate of about 980 g/hr via a line 31. A liquid component was extracted from a line 33 provided in the bottom of thin film distillation apparatus 302 and returned to feed tank 301 via a line 34. A gaseous component containing hexamethylene diisocyanate and 2,4-di-tert-amylphenol was extracted from a line 32 provided in the upper portion of a thin film distillation apparatus 302. The gaseous component was introduced into a distillation column 303 followed by separation into hexamethylene diisocyanate and 2,4-di-tert-amylphenol, and a portion of the 2,4-di-tert-amylphenol was returned to feed tank 301 through line 34 via a line 36 provided in the bottom of distillation column 303. When this reaction was carried out for 13 hours, 266 g of a solution were recovered from a line 35, and as a result of analyzing the solution by $^1$H- and $^{13}$C-NMR analysis, the solution was found to contain 99% by weight of hexamethylene diisocyanate. The yield based on hexamethylene diamine was 88%.

Example 2

Step (2-1): Production of N,N'-hexanediyl-bis-carbamic Acid Di(3-methylbutyl)Ester A solution containing 12.8% by weight of N,N'-hexanediyl-bis-carbamic acid di(3-methylbutyl)ester was obtained by carrying out the same method as step (1-1) of Example 1 with the exception of adding 2230 g of 3-methyl-1-butanol to a 5 L volumetric four-mouth flask and then adding 1515 g (7.5 mol) of bis(3-methylbutyl)carbonate and 174 g (1.5 mol) of hexamethylene diamine thereto and using 28.9 g of sodium methoxide. The solution was passed through a column packed with an ion exchange resin (Amberlyst 15 Dry, Rohm and Haas Co., USA) and 3919 g of solution were recovered.

Step (2-2): Distillation of Low Boiling Point Component 3373 g of a distillate were obtained by carrying out the same method as step (1-2) of Example 1 with the exception of using the solution obtained in step (2-1) instead of the solution obtained in step (1-1). As a result of analyzing by gas chromatography, the distillate was found to contain 27.0% by weight of bis(3-methylbutyl)carbonate and 72.9% by weight of 3-methyl-1-butanol. In addition, as a result of analyzing by liquid chromatography, the distillation residue in the flask was found to contain 92.1% by weight of N,N'-hexanediyl-bis-carbamic acid di(3-methylbutyl)ester.

Step (2-3): Production of N,N'-hexanediyl-bis-carbamic Acid Di(2,4-di-tert-butylphenyl)Ester by Transesterification 3351 g of a reaction liquid were extracted from line 24 by carrying out the same method as step (1-3) of Example 1 with the exception of using 544 g of the distillation residue obtained in step (2-2) instead of the distillation residue obtained in step (1-2), using 92 g of dibutyl tin dilaurate, using 2999 g of 2,4-di-tert-butylphenol (Wako Pure Chemical Industries, Ltd., Japan) instead of 2,4-di-tert-amylphenol, and carrying out the reaction for 70 hours. In addition, 246 g of a solution were recovered from line 27 provided in the upper portion of distillation column 203. The extracted reaction liquid contained 24.2% by weight of N,N'-hexanediyl-bis-carbamic acid di(2,4-di-tert-butylphenyl) ester.

Step (2-4): Production of Hexamethylene Diisocyanate by Thermal Decomposition of N,N'-hexanediyl-bis-carbamic Acid Di(2,4-di-tert-butylphenyl)Ester 225 g of a solution were recovered from line 35 by carrying out the same method as step (1-4) of Example 1 in a reaction apparatus like that shown in FIG. 2 with the exception of heating thin film distillation apparatus 302 to 200° C., setting the pressure within the thin film distillation apparatus to about 1.3 kPa, supplying the solution obtained in step (2-3) to the thin film distillation apparatus at the rate of about 980 g/hr via line 31, and carrying out the reaction for 11 hours. As a result of analyzing the solution by $^1$H- and $^{13}$C-NMR analysis, the solution was found to contain 99% by weight of hexamethylene diisocyanate. The yield based on hexamethylene diamine was 89%.

Example 3

Step (3-1): Production of N,N'-hexanediyl-bis-carbamic Acid Di(3-methylbutyl)Ester 2754 g of a solution containing 21.6% by weight of N,N'-hexanediyl-bis-carbamic acid di(3-methylbutyl)ester were obtained by carrying out the same method as step (1-1) of Example 1 with the exception of using 2545 g (12.6 mol) of bis(3-methylbutyl)carbonate and 209 g (1.8 mol) of hexamethylene diamine along with the stirrer, and using 3.5 g of sodium methoxide.

Step (3-2): Distillation of Low Boiling Point Component 2150 g of a distillate were obtained by carrying out the same method as step (1-2) of Example 1 with the exception of using the solution obtained in step (3-1) instead of the solution obtained in step (1-1). As a result of analyzing the distillate by gas chromatography, the distillate was found to contain 85.6% by weight of bis(3-methylbutyl)carbonate and 14.0% by weight of 3-methyl-1-butanol. In addition, as a result of analyzing by liquid chromatography, the distillation residue in the flask was found to contain 98.4% by weight of N,N'-hexanediyl-bis-carbamic acid di(3-methylbutyl)ester.

Step (3-3): Production of N,N'-hexanediyl-bis-carbamic Acid Di(2,4-di-tert-amylphenyl)Ester by Transesterification 4834 g of a reaction liquid were extracted from line 24 by carrying out the same method as step (1-3) of Example 1 with the exception of using 602 g of the distillation residue obtained in step (3-2) instead of the distillation residue obtained in step (1-2), using 109 g of dibutyl tin dilaurate, using 4431 g of 2,4-di-tert-amylphenol and carrying out the reaction for 70 hours. In addition, 297 g of a solution were recovered from line 27 provided in the upper portion of distillation column 203. The extracted reaction liquid contained 22.2% by weight of N,N'-hexanediyl-bis-carbamic acid di(2,4-di-tert-amylphenyl) ester.

Step (3-4): Distillation of 2,4-di-tert-amylphenol

A vacuum pump and a vacuum controller were attached to a molecular distillation apparatus having a jacketed heating unit operated by oil circulation (ϕ80 molecular distillation apparatus, Asahi Seisakusho Co., Ltd., Japan), and the purge line of the vacuum controller was connected to a nitrogen gas line. The air inside the molecular distillation apparatus was replaced with nitrogen and the heating unit was heated to 150° C. with an oil circulator. The pressure in the molecular distillation apparatus was reduced to 0.3 kPa, and the solution obtained in step (3-3) was fed to the molecular distillation apparatus at the rate of about 5 g/min while rotating the wiper of the molecular distillation apparatus at about 300 rpm to distill off the 2,4-di-tert-amylphenol. 1291 g of a high boiling point substance were recovered in a high boiling point sample collector held at 120° C. and as a result of analyzing by liquid chromatography, was found to contain 83.1% by weight of N,N'-hexanediyl-bis-carbamic acid di(2,4-di-tert-amylphenyl) ester.

Step (3-5): Production of Hexamethylene Diisocyanate by Thermal Decomposition of N,N'-hexanediyl-bis-carbamic Acid Di(2,4-di-tert-amylphenyl)Ester A thermal decomposition reaction was carried out in a reaction apparatus like that shown in FIG. 2.

290 g of a solution were recovered from line 35 by carrying out the same method as step (1-4) of Example 1 with the exception of feeding a mixed liquid in the form of a slurry comprising a mixture of 1289 g of the carbamic acid ester-containing substance obtained in step (3-4) and 3422 g of benzylbutyl phthalate (guaranteed reagent, Wako Pure Chemical Industries, Ltd., Japan) to feed tank 301, supplying to the thin film distillation apparatus at the rate of about 980 g/hr and reacting for 14 hours. As a result of analyzing the solution by $^1$H- and $^{13}$C-NMR analysis, the solution was found to contain 99% by weight of hexamethylene diisocyanate. The yield based on hexamethylene diamine was 83%.

Example 4

Step (4-1): Production of N,N'-hexanediyl-bis-carbamic Acid Dibutyl Ester

A solution containing 30.8% by weight of N,N'-hexanediyl-bis-carbamic acid dibutyl ester was obtained by carrying out the same method as step (1-1) of Example 1 with the exception of using 1479 g (8.5 mol) of dibutyl carbonate produced according to the method of Reference Example 2 and 197 g (1.7 mol) of hexamethylene diamine (Aldrich Corp., USA), and using 3.3 g of sodium methoxide (28% methanol solution, Wako Pure Chemical Industries, Ltd., Japan) in a 5 L volumetric four-mouth flask.

Step (4-2): Distillation of Low Boiling Point Component 1156 g of a distillate were obtained by carrying out the same method as step (1-2) of Example 1 with the exception of using the solution obtained in step (4-1) instead of the solution obtained in step (1-1). As a result of analyzing by gas chromatography, the distillate was found to contain 78.5% by weight of dibutyl carbonate and 20.8% by weight of n-butanol. In addition, as a result of analyzing by liquid chromatography, the distillation residue in the flask was found to contain 98.8% by weight of N,N'-hexanediyl-bis-carbamic acid dibutyl ester.

Step (4-3): Production of N,N'-hexanediyl-bis-carbamic Acid Di(2,4-di-tert-amylphenyl)Ester by Transesterification 4929 g of a reaction liquid were extracted from line 24 by carrying out the same method as step (1-3) of Example 1 with the exception of using the distillation residue obtained in step (4-2) instead of the distillation residue obtained in step (1-2), using 82 g of dibutyl tin dilaurate, adding 4566 g of 2,4-di-tert-amylphenol followed by stirring to obtain a homogeneous solution that was then fed to feed tank 201, heating thin film distillation apparatus 202 having a heat-conducting surface area of 0.2 m$^2$ to 240° C. and reacting for 86 hours. 233 g of a solution were recovered from line 27 provided in the upper portion of distillation column 203.

When the extracted reaction liquid was analyzed by liquid chromatography, the reaction liquid was found to contain 20.4% by weight of N,N'-hexanediyl-bis-carbamic acid di(2,4-di-tert-amylphenyl) ester. In addition, when the solution recovered from line 27 was analyzed by $^1$H- and $^{13}$C-NMR analysis, the solution was found to contain 99.9% by weight 1-butanol.

Step (4-4): Production of Hexamethylene Diisocyanate by Thermal Decomposition of N,N'-hexanediyl-bis-carbamic Acid Di(2,4-di-tert-amylphenyl)Ester A thermal decomposition reaction was carried out in a reaction apparatus like that shown in FIG. 2.

248 g of a solution were recovered from line 35 by carrying out the same method as step (1-4) of Example 1 with the exception of using the solution extracted from line 24 in step (4-3) instead of the solution extracted from line 24 in step (1-3) and reacting for 14 hours. As a result of analyzing the solution by $^1$H- and $^{13}$C-NMR analysis, the solution was found to contain 99% by weight of hexamethylene diisocyanate. The yield based on hexamethylene diamine was 87%.

Example 5

Step (5-1): Production of N,N'-hexanediyl-bis-carbamic Acid Dibutyl Ester 2091 g of a solution containing 26.2% by weight of N,N'-hexanediyl-bis-carbamic acid dibutyl ester was obtained by carrying out the same method as step (1-1) of Example 1 with the exception of using 1879 g (10.8 mol) of dibutyl carbonate and 209 g (1.8 mol) of hexamethylene diamine, adding a stirrer and adding 3.5 g of sodium methoxide.

Step (5-2): Distillation of Low Boiling Point Component 1537 g of a distillate were obtained by carrying out the same method as step (1-2) of Example 1 with the exception of using the solution obtained in step (5-1) instead of the solution obtained in step (1-1). As a result of analyzing by gas chromatography, the distillate was found to contain 82.9% by weight of dibutyl carbonate and 16.6% by weight of n-butanol. In addition, as a result of analyzing by liquid chromatography, the distillation residue in the flask was found to contain 99.0% by weight of N,N'-hexanediyl-bis-carbamic acid dibutyl ester.

Step (5-3): Production of N,N'-hexanediyl-bis-carbamic Acid Di(2,6-dimethylphenyl)Ester by Transesterification 3554 g of a reaction liquid were extracted from line 24 by carrying out the same method as step (1-3) of Example 1 with the exception of using 548 g of the distillation residue obtained in step (5-2) instead of the distillation residue obtained in step (1-2), using 3142 g of 2,6-dimethylphenol (Aldrich Corp., USA) instead of 2,4-di-tert-amylphenol, using 109 g of dibutyl tin dilaurate, making the temperature of thin film distillation apparatus 202 200° C. and carrying out the reaction for 225 hours. In addition, 239 g of a solution was recovered from line 27 provided in the upper portion of distillation column 203. The extracted reaction liquid contained 18.7% by weight of N,N'-hexanediyl-bis-carbamic acid di(2,6-dimethylphenyl)ester.

Step (5-4): Production of Hexamethylene Diisocyanate by Thermal Decomposition of N,N'-hexanediyl-bis-carbamic Acid Di(2,6-dimethylphenyl)Ester A thermal decomposition reaction was carried out in a reaction apparatus like that shown in FIG. 4.

A thin film distillation apparatus 402 (Kobelco Eco-Solutions Co., Ltd., Japan) having a heat-conducting surface area of 0.2 m$^2$ was heated to 200° C. and the pressure within the thin film distillation apparatus was set to about 1.3 kPa. The solution obtained in step (5-3) was placed in a feed tank 401 and supplied to the thin film distillation apparatus at the rate of about 680 g/hr via a line 41. A liquid component was extracted from a line 43 provided in the bottom of thin film distillation apparatus 402 and returned to feed tank 401 via a line 44. A gaseous component containing hexamethylene diisocyanate and 2,6-dimethylphenol was extracted from a line 42 provided in the upper portion of thin film distillation apparatus 402. The gaseous component was introduced into a distillation column 403 followed by separation into hexamethylene diisocyanate and 2,6-dimethylphenol, the 2,6-dimethylphenol was extracted from a line 45 via the top of the distillation column 403, and a gaseous component containing hexamethylene diisocyanate was extracted from a line 47 provided in the distillation column 403. On the other hand, a high boiling point substance was extracted from a line 46 provided in the bottom of the distillation column, and a portion was returned feed tank 401 through line 44. The gaseous component containing hexamethylene diisocyanate extracted from line 47 was pumped to a distillation column 404, and the hexamethylene diisocyanate was distilled off and separated in the distillation column 404. A high boiling point substance was extracted from a line 48 provided in the distillation column 404, and a portion was returned to feed tank 401 through line 44. On the other hand, a gaseous component was extracted from a line 49, and hexamethylene diisocyanate was extracted from a line 52 via a condenser. After reacting for 11 hours, 249 g of a solution containing 99% by weight of hexamethylene diisocyanate was recovered from line 47. The yield based on hexamethylene diamine was 82%.

Example 6

Step (6-1): Production of N,N'-hexanediyl-bis-carbamic Acid Dimethyl Ester

A solution containing 39.0% by weight of N,N'-hexanediyl-bis-carbamic acid dimethyl ester therein was obtained by carrying out the same method as step (1-1) of Example 1 with the exception of using 765 g (8.5 mol) of dimethyl carbonate (Aldrich Corp., USA) and 197 g (1.7 mol) of hexamethylene diamine, and using 3.3 g of sodium methoxide in a 2 L volumetric four-mouth flask.

Step (6-2): Distillation of Low Boiling Point Component 582 g of a distillate were obtained by carrying out the same method as step (1-2) of Example 1 with the exception of using the solution obtained in step (6-1) instead of the solution obtained in step (1-1). As a result of analyzing by gas chromatography, the distillate was found to contain 80.8% by weight of dimethyl carbonate and 17.9% by weight of methanol. In addition, as a result of analyzing by liquid chromatography, the distillation residue in the flask was found to contain 98.9% by weight of N,N'-hexanediyl-bis-carbamic acid dimethyl ester.

Step (6-3): Production of N,N'-hexanediyl-bis-carbamic Acid Di(2,4-di-tert-amylphenyl)Ester by Transesterification 4517 g of a reaction liquid were extracted from line 24 by carrying out the same method as step (1-3) of Example 1 with the exception of using 376 g of the distillation residue in the flask obtained in step (6-2) instead of the distillation residue in the flask obtained in step (1-2), using 82 g of dibutyl tin dilaurate, using 4161 g of 2,4-di-tert-amylphenol and carrying out the reaction for 86 hours. 100 g of a solution were recovered from line 27 provided in the upper portion of distillation column 203.

When the extracted reaction liquid was analyzed by liquid chromatography, the reaction liquid was found to contain 22.1% by weight of N,N'-hexanediyl-bis-carbamic acid di(2,4-di-tert-amylphenyl) ester. In addition, when the solution recovered from line 27 was analyzed by $^1$H- and $^{13}$C-NMR analysis, the solution was found to contain 99.4% by weight methanol.

Step (6-4): Production of Hexamethylene Diisocyanate by Thermal Decomposition of N,N'-hexanediyl-bis-carbamic Acid Di(2,4-di-tert-amylphenyl)Ester 242 g of a solution were recovered from line 35 by carrying out the same method as step (1-4) of Example 1 with the exception of using the solution extracted from line 24 in step (6-3) instead of the solution extracted from line 24 in step (1-3), and carrying out the reaction for 13 hours. As a result of analyzing the solution by $^1$H- and $^{13}$C-NMR analysis, the solution was found to contain 99% by weight of hexamethylene diisocyanate. The yield based on hexamethylene diamine was 85%.

Example 7

Step (7-1): Production of N,N'-hexanediyl-bis-carbamic Acid Dimethyl Ester 934 g of a solution containing 42.4% by weight of N,N'-hexanediyl-bis-carbamic acid dimethyl ester was obtained by carrying out the same method as step (1-1) of Example 1 with the exception of using 729 g (8.1 mol) of dimethyl carbonate and 209 g (1.8 mol) of hexamethylene diamine, and using 0.35 g of sodium methoxide.

Step (7-2): Distillation of Low Boiling Point Component 533 g of a distillate were obtained by carrying out the same method as step (1-2) of Example 1 with the exception of using the solution obtained in step (7-1) instead of the solution obtained in step (1-1). As a result of analyzing by gas chromatography, the distillate was found to contain 77.8% by weight of dimethyl carbonate and 20.6% by weight of methanol. In addition, as a result of analyzing by liquid chromatography, the distillation residue in the flask was found to contain 99.7% by weight of N,N'-hexanediyl-bis-carbamic acid dimethyl ester.

Step (7-3): Production of N,N'-hexanediyl-bis-carbamic Acid Di(2,6-di-methylphenyl)Ester by Transesterification 3537 g of a reaction liquid were extracted from line 24 by carrying out the same method as step (1-3) of Example 1 with the exception of using 395 g of the distillation residue obtained in step (7-2) instead of the distillation residue obtained in step (1-2), using 108 g of dibutyl tin dilaurate, using 3133 g of 2,6-dimethylphenol instead of 2,4-di-tert-amylphenol, heating the thin film distillation apparatus 202 to 200° C. and carrying out the reaction for 250 hours. In addition, 100 g of a solution were recovered from line 27 provided in the upper portion of distillation column 203. The extracted reaction liquid contained 18.3% by weight of N,N'-hexanediyl-bis-carbamic acid di(2,6-di-methylphenyl) ester.

Step (7-4): Production of Hexamethylene Diisocyanate by Thermal Decomposition of N,N'-hexanediyl-bis-carbamic Acid Di(2,6-di-methylphenyl)Ester 243 g of a solution containing 99% by weight of hexamethylene diisocyanate were recovered from line 52 by carrying out the same method as step (5-4) of Example 5 with the exception of using the reaction liquid obtained from line 24 in step (7-3) instead of the solution obtained in step (5-3), and carrying out the reaction for 16 hours. The yield with respect to hexamethylene diamine was 81%.

Example 8

Step (8-1): Production of 3-((3-methylbutyl)oxycarbonylamino-methyl)-3,5,5-trimethylcyclohexylcarbamic Acid (3-methylbutyl)Ester 1980 g (9.8 mol) of bis(3-methylbutyl)carbonate and 239 g (1.8 mol) of 3-aminomethyl-3,5,5-trimethylcyclohexylamine (Aldrich Corp., USA) were placed in a 5 L volumetric fourth-mouth flask, a stirrer was placed in the flask, and a Dimroth condenser and three-way valve were attached to the flask. After replacing the inside of the system with nitrogen, the four-mouth flask was immersed in an oil bath (OBH-24, Masuda Corp., Japan) heated to 100° C. followed by the addition of 2.7 g of sodium methoxide (28% methanol solution, Wako Pure Chemical Industries, Ltd., Japan) to start the reaction. Samples of the reaction liquid were suitably collected and subjected to NMR analysis, and the reaction was terminated at the point 3-aminomethyl-3,5,5-trimethylcyclohexylamine was no longer detected. As a result of analyzing the resulting solution by liquid chromatography, the solution was found to contain 23.9% by weight of 3-((3-methylbutyl)oxycarbonylamino-methyl)-3,5,5-trimethylcyclohexyl carbamic acid (3-methylbutyl)ester.

Step (8-2): Distillation of Low Boiling Point Component 1683 g of a distillate were obtained by carrying out the same method as step (1-2) of Example 1 with the exception of using the solution obtained in step (8-1) instead of the solution obtained in step (1-1). As a result of analyzing by gas chromatography, the distillate was found to contain 85.4% by weight of bis(3-methylbutyl)carbonate and 13.8% by weight of 3-methyl-1-butanol. In addition, as a result of analyzing by liquid chromatography, the distillation residue in the flask was found to contain 99.4% by weight of 3-((3-methylbutyl)oxycarbonylamino-methyl)-3,5,5-trimethylcyclohexylcarbamic acid (3-methylbutyl)ester.

Step (8-3): Production of 3-((2,4-di-tert-amylphenyl)oxycarbonylamino-methyl)-3,5,5-trimethylcyclohexyl carbamic Acid (2,4-di-tert-amylphenyl)Ester by Transesterification 5034 g of a reaction liquid were extracted from line 24 and 221 g of a solution were recovered from line 27 provided in the upper portion of distillation column 203 by carrying out the same method as step (1-3) of Example 1 with the exception of using 530 g of the distillation residue obtained in step (8-2) instead of the distillation residue obtained in step (1-2), using 84 g of dibutyl tin dilaurate, using 4645 g of 2,4-di-tert-amylphenol, heating the thin film distillation apparatus 202 to 240° C., supplying the solution to the thin film distillation apparatus via feed line 21 at the rate of about 1200 g/hr, and carrying out the reaction for 75 hours.

When the extracted reaction liquid was analyzed by liquid chromatography, the reaction liquid was found to contain 17.2% by weight of 3-((2,4-di-tert-amylphenyl)oxycarbonylamino-methyl)-3,5,5-trimethylcyclohexyl carbamic acid (2,4-di-tert-amylphenyl)ester. In addition, when the solution recovered from line 27 was analyzed by $^1$H- and $^{13}$C-NMR analysis, the solution was found to contain 99% by weight of 3-methyl-1-butanol.

Step (8-4): Production of Isophorone Diisocyanate by Thermal Decomposition of 3-((2,4-di-tert-amylphenyl)oxycarbonylamino-methyl)-3,5,5-trimethylcyclohexylcarbamic Acid (2,4-di-tert-amylphenyl)Pentyl Ester 257 g of a solution containing 99% by weight of isophorone diisocyanate were recovered from line 52 by carrying out the same method as step (5-4) of Example 5 with the exception of heating the thin film distillation apparatus 402 to 200° C., making the pressure in the thin film distillation apparatus about 1.3 kPa, feeding the solution obtained in step (8-3) to feed tank 401, supplying to the thin film distillation apparatus via line 41 at the rate of about 680 g/hr, and carrying out the reaction for 11 hours. The yield based on 3-aminomethyl-3,5,5-trimethylcyclohexylamine was 83%.

Example 9

Step (9-1): Production of 3-(butyloxycarbonylamino-methyl)-3,5,5-trimethylcyclohexylcarbamic Acid Butyl Ester The same method as step (8-1) of Example 8 was carried out with the exception of using 2349 g (13.5 mol) of dibutyl carbonate, 255 g (1.5 mol) of 3-aminomethyl-3,5,5-trimethylcyclohexylamine and 2.9 g of sodium methoxide. As a result of analyzing the resulting solution by liquid chromatography, the solution was found to contain 20.0% by weight of 3-(butyloxycarbonylamino-methyl)-3,5,5-trimethylcyclohexylcarbamic acid butyl ester therein.

Step (9-2): Distillation of Low Boiling Point Component 2075 g of a distillate were obtained by carrying out the same method as step (1-2) of Example 1 with the exception of using the solution obtained in step (9-1) instead of the solution obtained in step (1-1). As a result of analyzing by gas chromatography, the distillate was found to contain 89.2% by weight of dibutyl carbonate and 10.0% by weight of n-butanol. In addition, as a result of analyzing by liquid chromatography, the distillation residue in the flask was found to contain 98.7% by weight of 3-(butyloxycarbonylamino-methyl)-3,5,5-trimethylcyclohexylcarbamic acid butyl ester.

Step (9-3): Production of 3-((2,4-di-tert-butylphenyl)oxycarbonylamino-methyl)-3,5,5-trimethylcyclohexyl carbamic Acid (2,4-di-tert-butylphenyl)Ester by Transesterification 4077 g of a reaction liquid were extracted from line 24 and 197 g of a solution were recovered from line 27 provided in the upper portion of distillation column 203 by carrying out the same method as step (1-3) of Example 1 with the exception of using 525 g of the distillation residue obtained in step (9-2), using 89 g of dibutyl tin dilaurate, using 3751 g of 2,4-di-tert-butylphenol to obtain a homogeneous solution, heating the thin film distillation apparatus 202 to 240° C., replacing the inside of the thin film distillation apparatus with nitrogen at atmospheric pressure, supplying the solution to the thin film distillation apparatus via supply line 21 at the rate of about 1200 g/hr and carrying out the reaction for 84 hours.

When the recovered reaction liquid was analyzed by liquid chromatography, the reaction liquid was found to contain 20.7% by weight of 3-((2,4-di-tert-butylphenyl)oxycarbonylamino-methyl)-3,5,5-trimethylcyclohexyl carbamic acid (2,4-di-tert-butylphenyl) ester. In addition, when the solution recovered from line 27 was analyzed by $^1$H- and $^{13}$C-NMR analysis, the solution was found to contain 98% by weight of 1-butanol.

Step (9-4): Production of Isophorone Diisocyanate by Thermal Decomposition of 3-((2,4-di-tert-butylphenyl)oxycarbonylamino-methyl)-3,5,5-trimethylcyclohexylcarbamic Acid (2,4-di-tert-butylphenyl) Ester 271 g of a solution containing 99% by weight of isophorone diisocyanate were recovered from line 52 by carrying out the same method as step (5-4) of Example 5 with the exception of heating the thin film distillation apparatus 402 to 200° C., making the pressure in the thin film distillation apparatus about 1.3 kPa, feeding the solution obtained in step (9-3) to feed tank 401, supplying to the thin film distillation apparatus via line 41 at the rate of about 680 g/hr, and carrying out the reaction for 11 hours. The yield based on 3-aminomethyl-3,5,5-trimethylcyclohexylamine was 82%.

Example 10

Step (10-1): Production of 3-(butyloxycarbonylamino-methyl)-3,5,5-trimethylcyclohexylcarbamic acid Butyl Ester A solution containing 25.1% by weight of 3-(butyloxycarbonylamino-methyl)-3,5,5-trimethylcyclohexylcarbamic acid butyl ester was obtained by carrying out the same method as step (8-1) of Example 8 with the exception of using 1949 g (11.2 mol) of dibutyl carbonate, 272 g (1.6 mol) of 3-aminomethyl-3,5,5-trimethylcyclohexylamine and 3.1 g of sodium methoxide.

Step (10-2): Distillation of Low Boiling Point Component 1657 g of a distillate were obtained by carrying out the same method as step (1-2) of Example 1 with the exception of using the solution obtained in step (10-1) instead of the solution obtained in step (1-1). As a result of analyzing by gas chromatography, the distillate was found to contain 85.7% by weight of dibutyl carbonate and 13.4% by weight of n-butanol. In addition, as a result of analyzing by liquid chromatography, the distillation residue in the flask was found to contain 98.9% by weight of 3-(butyloxycarbonylamino-methyl)-3,5,5-trimethylcyclohexylcarbamic acid butyl ester.

Step (10-3): Production of 3-((2,4,6-tri-methylphenyl)oxycarbonylamino-methyl)-3,5,5-trimethylcyclohexylcarbamic Acid (2,4,6-tri-methylphenyl)Ester by Transesterification 3067 g of a reaction liquid were extracted from line 24 and 208 g of a solution were recovered from line 27 provided in the upper portion of distillation column 203 by carrying out the same method as step (1-3) of Example 1 with the exception of adding 76 g of dibutyl tin dilaurate to 560 g of the distillation residue obtained in step (10-2), adding 2645 g of 2,4,6-trimethylphenol (Aldrich Corp., USA) and using in the form of a homogeneous solution, heating the thin film distillation apparatus 202 to 220° C., replacing the inside of the thin film distillation apparatus with nitrogen at atmospheric pressure, supplying the solution to the thin film distillation apparatus via supply line 21 at the rate of about 120 g/hr and carrying out the reaction for 180 hours.

When the extracted reaction liquid was analyzed by liquid chromatography, the reaction liquid was found to contain 22.7% by weight of 3-((2,4,6-tri-methylphenyl)oxycarbonylamino-methyl)-3,5,5-trimethylcyclohexylcarbamic acid (2,4,6-trimethylphenyl) ester. In addition, when the solution recovered from line 27 was analyzed by $^1$H- and $^{13}$C-NMR analysis, the solution was found to contain 99% by weight of 1-butanol.

Step (10$^{-4}$): Production of Isophorone Diisocyanate by Thermal Decomposition of 3-((2,4,6-trimethylphenyl)oxycarbonylamino-methyl)-3,5,5-trimethylcyclohexylcarbamic Acid (2,4,6-trimethylphenyl) Ester 286 g of a solution containing 99% by weight of isophorone diisocyanate were recovered from line 52 by carrying out the same method as step (5-4) of Example 5 with the exception of heating the thin film distillation apparatus 402 to 200° C., making the pressure in the thin film distillation apparatus about 1.3 kPa, feeding the solution obtained in step (10-3) to feed tank 401, supplying to the thin film distillation apparatus via line 41 at the rate of about 680 g/hr, and carrying out the reaction for 14 hours. The yield based on 3-aminomethyl-3,5,5-trimethylcyclohexylamine was 81%.

Example 11

Step (11-1): Production of 3-(methyloxycarbonylamino-methyl)-3,5,5-trimethylcyclohexylcarbamic acid Methyl Ester A solution containing 33.6% by weight of 3-(methyloxycarbonylamino-methyl)-3,5,5-trimethylcyclohexylcarbamic acid methyl ester was obtained by carrying out the same method as step (8-1) of Example 8 with the exception of using 1323 g (14.7 mol) of dimethyl carbonate, 357 g (2.1 mol) of 3-aminomethyl-3,5,5-trimethylcyclohexylamine and 4.1 g of sodium methoxide.

Step (11-2): Distillation of Low Boiling Point Component 1111 g of a distillate were obtained by carrying out the same method as step (1-2) of Example 1 with the exception of using the solution obtained in step (11-1) instead of the solution obtained in step (1-1). As a result of analyzing by gas chromatography, the distillate was found to contain 86.7% by weight of dimethyl carbonate and 11.3% by weight of methanol. In addition, as a result of analyzing by liquid chromatography, the distillation residue in the flask was found to contain 99.1% by weight of 3-(methyloxycarbonylamino-methyl)-3,5,5-trimethylcyclohexylcarbamic acid methyl ester.

Step (11-3): Production of 3-((2,4,6-tri-methylphenyl)oxycarbonylamino-methyl)-3,5,5-trimethylcyclohexylcarbamic Acid (2,4,6-tri-methylphenyl)Ester by Transesterification A transesterification reaction was carried out in a reaction apparatus like that shown in FIG. 2.

4457 g of a reaction liquid were extracted from line 24 and 118 g of a solution were recovered from line 27 provided in the upper portion of distillation column 203 by carrying out the same method as step (1-3) of Example 1 with the exception of adding 99 g of dibutyl tin dilaurate and 4006 g of 2,4,6-trimethylphenol to 567 g of the distillation residue obtained in step (11-2) and using in the form of a homogeneous solution, heating the thin film distillation apparatus 202 to 220° C., replacing the inside of the thin film distillation apparatus with nitrogen at atmospheric pressure, supplying the solution to the thin film distillation apparatus via supply line 21 at the rate of about 1200 g/hr and carrying out the reaction for 90 hours.

When the reaction liquid was analyzed by liquid chromatography, the reaction liquid was found to contain 20.5% by weight of 3-((2,4,6-tri-methylphenyl)oxycarbonylamino-methyl)-3,5,5-trimethylcyclohexylcarbamic acid (2,4,6-trimethylphenyl) ester. In addition, when the solution recovered from line 27 was analyzed by $^1$H- and $^{13}$C-NMR analysis, the solution was found to contain 99% by weight of methanol.

Step (11-4): Production of Isophorone Diisocyanate by Thermal Decomposition of 3-((2,4,6-trimethylphenyl)oxycarbonylamino-methyl)-3,5,5-trimethylcyclohexylcarbamic Acid (2,4,6-trimethylphenyl) Ester 368 g of a solution containing 99% by weight of isophorone diisocyanate were recovered from line 47 by carrying out the same method as step (5-4) of Example 5 with the exception of heating the thin film distillation apparatus 402 to 200° C., making the pressure in the thin film distillation apparatus about 1.3 kPa, feeding the solution obtained in step (11-3) to feed tank 401, supplying to the thin film distillation apparatus via line 41 at the rate of about 900 g/hr, and carrying out the reaction for 13 hours. The yield based on 3-aminomethyl-3,5,5-trimethylcyclohexylamine was 79%.

Example 12

Step (12-1): Production of Bis(3-methylbutyl)-4,4'-methylene-dicyclohexyl Carbamate 1313 g (6.5 mol) of bis(3-methylbutyl)carbonate and 273 g (1.3 mol) of 4,4'-methylenebis(cyclohexylamine) (Aldrich Corp., USA) were placed in a 5 L volumetric fourth-mouth flask, a stirrer was placed in the flask, and a Dimroth condenser and three-way valve were attached to the flask. After replacing the inside of the system with nitrogen, the four-mouth flask was immersed in an oil bath (OBH-24, Masuda Corp., Japan) heated to 10° C. followed by the addition of 2.5 g of sodium methoxide to start the reaction. Samples of the reaction liquid were suitably collected and subjected to NMR analysis, and the reaction was terminated at the point 4,4'-methylenebis(cyclohexylamine) was no longer detected. As a result of analyzing the resulting solution by liquid chromatography, the solution was found to contain 34.3% by weight of bis(3-methylbutyl)-4,4'-methylene-dicyclohexyl carbamate.

Step (12-2): Distillation of Low Boiling Point Component 1034 g of a distillate were obtained by carrying out the same method as step (1-2) of Example 1 with the exception of using the solution obtained in step (12-1) instead of the solution obtained in step (1-1). As a result of analyzing by gas chromatography, the distillate was found to contain 77.8% by weight of bis(3-methylbutyl)carbonate and 21.2% by weight of 3-methyl-1-butanol. In addition, as a result of analyzing by liquid chromatography, the distillation residue in the flask was found to contain 99.0% by weight of bis(3-methylbutyl)-4,4'-methylene-dicyclohexyl carbamate.

Step (12-3): Production of Bis(2,4-di-tert-amylphenyl)-4,4'-methylene-dicyclohexyl Carbamate by Transesterification 4702 g of a reaction liquid were extracted from line 24 and 210 g of a solution were recovered from line 27 provided in the upper portion of distillation column 203 by carrying out the same method as step (1-3) of Example 1 with the exception of adding 79 g of dibutyl tin dilaurate and 4358 g of 2,4-di-tert-amylphenol to 547 g of the distillation residue obtained in step (12-2) and using in the form of a homogeneous solution, heating the thin film distillation apparatus 202 to 260° C., replacing the inside of the thin film distillation apparatus with nitrogen at atmospheric pressure, supplying the solution to the thin film distillation apparatus via supply line 21 at the rate of about 1200 g/hr and carrying out the reaction for 58 hours.

When the reaction liquid was analyzed by liquid chromatography, the reaction liquid was found to contain 18.2% by weight of bis(2,4-di-tert-amylphenyl)-4,4'-methylene-dicyclohexyl carbamate. In addition, when the solution recovered from line 27 was analyzed by $^1$H- and $^{13}$C-NMR analysis, the solution was found to contain 99% by weight of 3-methyl-1-butanol.

Step (12-4): Production of Hexamethylene Diisocyanate by Thermal Decomposition of Bis(2,4-di-tert-amylphenyl)-4,4'-methylene-dicyclohexyl Carbamate 287 g of a substance containing 99% by weight of 4,4'-methylene-di(cyclohexylisocyanate) were recovered from line 47 by carrying out the same method as step (5-4) of Example 5 with the exception of heating the thin film distillation apparatus 402 to 210° C., making the pressure in the thin film distillation apparatus about 0.13 kPa, feeding the solution obtained in step (12-3) to feed tank 401, supplying to the thin film distillation apparatus via line 41 at the rate of about 680 g/hr, and carrying out the reaction for 11 hours. The yield based on 4,4'-methylenebis(cyclohexylamine) was 84%.

Example 13

Step (13-1): Production of Bis(3-methylbutyl)-4,4'-methylene-dicyclohexyl Carbamate A solution containing 29.4% by weight of bis(3-methylbutyl)-4,4'-methylene-dicyclohexyl carbamate was obtained by carrying out the same method as step (12-1) of Example 12 with the exception of using 1818 g (9.0 mol) of bis(3-methylbutyl)carbonate, 315 g (1.5 mol) of 4,4'-methylenebis(cyclohexylamine) and 2.9 g of sodium methoxide.

Step (13-2): Distillation of Low Boiling Point Component 1490 g of a distillate were obtained by carrying out the same method as step (1-2) of Example 1 with the exception of using the solution obtained in step (13-1) instead of the solution obtained in step (1-1). As a result of analyzing by gas chromatography, the distillate was found to contain 82.6% by weight of bis(3-methylbutyl)carbonate and 16.8% by weight of 3-methyl-1-butanol. In addition, as a result of analyzing by liquid chromatography, the distillation residue in the flask was found to contain 98.0% by weight of bis(3-methylbutyl)-4,4'-methylene-dicyclohexyl carbamate.

Step (13-3): Production of Bis(2,4-di-tert-butylphenyl)-4,4'-methylene-dicyclohexyl Carbamate by Transesterification 4987 g of a reaction liquid were extracted from line 24 and 238 g of a solution were recovered from line 27 provided in the upper portion of distillation column 203 by carrying out the same method as step (1-3) of Example 1 with the exception of adding 90 g of dibutyl tin dilaurate and 4511 g of 2,4-di-tert-butylphenol to 633 g of the distillation residue obtained in step (13-2) and using in the form of a homogeneous solution, heating the thin film distillation apparatus 202 to 240° C., replacing the inside of the thin film distillation apparatus with nitrogen at atmospheric pressure, supplying the solution to the thin film distillation apparatus via supply line 21 at the rate of about 1200 g/hr and carrying out the reaction for 78 hours.

When the reaction liquid was analyzed by liquid chromatography, the reaction liquid was found to contain 18.3% by weight of bis(2,4-di-tert-butylphenyl)-4,4'-methylene-dicyclohexyl carbamate. In addition, when the solution recovered from line 27 was analyzed by $^1$H- and $^{13}$C-NMR analysis, the solution was found to contain 99% by weight of 3-methyl-1-butanol.

Step (13-4): Production of 4,4'-methylene-di(cyclohexylisocyanate) by Thermal Decomposition of Bis(2,4-di-tert-butylphenyl)-4,4'-methylene-dicyclohexyl Carbamate 325 g of a substance containing 99% by weight of 4,4'-methylene-di(cyclohexylisocyanate) were recovered from line 52 by carrying out the same method as step (5-4) of Example 5 with the exception of heating the thin film distillation apparatus 402 to 210° C., making the pressure in the thin film distillation apparatus about 0.13 kPa, feeding the solution obtained in step (13-3) to feed tank 401, supplying to the thin film distillation apparatus via line 41 at the rate of about 680 g/hr, and carrying out the reaction for 14 hours. The yield based on 4,4'-methylenebis(cyclohexylamine) was 83%.

Example 14

Step (14-1): Production of Dibutyl-4,4'-methylene-dicyclohexyl Carbamate

A solution containing 29.0% by weight of dibutyl-4,4'-methylene-dicyclohexyl carbamate was obtained by carrying out the same method as step (12-1) of Example 12 with the exception of using 1696 g (9.8 mol) of dibutyl carbonate, 315 g (1.5 mol) of 4,4'-methylenebis(cyclohexylamine) and 2.9 g of sodium methoxide.

Step (14-2): Distillation of Low Boiling Point Component 1409 g of a distillate were obtained by carrying out the same method as step (1-2) of Example 1 with the exception of using the solution obtained in step (14-1) instead of the solution obtained in step (1-1). As a result of analyzing by gas chromatography, the distillate was found to contain 84.0% by weight of dibutyl carbonate and 14.9% by weight of n-butanol. In addition, as a result of analyzing by liquid chromatography, the distillation residue in the flask was found to contain 97.3% by weight of dibutyl-4,4'-methylene-dicyclohexyl carbamate.

Step (14-3): Production of Bis(2,6-dimethylphenyl)-4,4'-methylene-dicyclohexyl Carbamate by Transesterification 3923 g of a reaction liquid were extracted from line 24 and 194 g of a solution were recovered from line 27 provided in the upper portion of distillation column 203 by carrying out the same method as step (1-3) of Example 1 with the exception of adding 89 g of dibutyl tin dilaurate and 3447 g of 2,6-dimethylphenol to 595 g of the distillation residue obtained in step (14-2) and using in the form of a homogeneous solution, heating the thin film distillation apparatus 202 to 200° C., replacing the inside of the thin film distillation apparatus with nitrogen at atmospheric pressure, supplying the solution to the thin film distillation apparatus via supply line 21 at the rate of about 1200 g/hr and carrying out the reaction for 350 hours.

When the reaction liquid was analyzed by liquid chromatography, the reaction liquid was found to contain 16.8% by weight of bis(2,6-dimethylphenyl)-4,4'-methylene-dicyclohexyl carbamate. In addition, when the solution recovered from line 27 was analyzed by $^1$H- and $^{13}$C-NMR analysis, the solution was found to contain 97% by weight of 1-butanol.

Step (14-4): Production of 4,4'-methylene-di(cyclohexylisocyanate) by Thermal Decomposition of Bis (2,6-dimethylphenyl)-4,4'-methylene-dicyclohexyl Carbamate 313 g of a solution containing 99% by weight of 4,4'-methylene-di(cyclohexylisocyanate) were recovered from line 52 by carrying out the same method as step (5-4) of Example 5 with the exception of heating the thin film distillation apparatus 402 to 210° C., making the pressure in the thin film distillation apparatus about 0.13 kPa, feeding the solution obtained in step (14-3) to feed tank 401, supplying to the thin film distillation apparatus via line 41 at the rate of about 700 g/hr, and carrying out the reaction for 15 hours. The yield based on 4,4'-methylenebis(cyclohexylamine) was 80%.

Example 15

Step (15-1): Production of Dibutyl-4,4'-methylene-dicyclohexyl Carbamate

A solution containing 27.0% by weight of dibutyl-4,4'-methylene-dicyclohexyl carbamate was obtained by carrying out the same method as step (12-1) of Example 12 with the exception of using 1705 g (9.8 mol) of dibutyl carbonate, 294 g (1.4 mol) of 4,4'-methylenebis(cyclohexylamine) and 0.27 g of sodium methoxide (28% methanol solution, Wako Pure Chemical Industries, Ltd.).

Step (15-2): Distillation of Low Boiling Point Component 1643 g of a distillate were obtained by carrying out the same method as step (1-2) of Example 1 with the exception of using the solution obtained in step (15-1) instead of the solution obtained in step (1-1). As a result of analyzing by gas chromatography, the distillate was found to contain 87.7% by weight of dibutyl carbonate and 11.7% by weight of n-butanol. In addition, as a result of analyzing by liquid chromatography, the distillation residue in the flask was found to contain 99% by weight of dibutyl-4,4'-methylene-dicyclohexyl carbamate.

Step (15-3): Production of Bis(2-tert-butylphenyl)-4,4'-methylene-dicyclohexyl Carbamate by Transesterification 4256 g of a reaction liquid were extracted from line 24 and 181 g of a solution were recovered from line 27 provided in the upper portion of distillation column 203 by carrying out the same method as step (1-3) of Example 1 with the exception of adding 84 g of dibutyl tin dilaurate and 3980 g of 2-tert-butylphenol to 562 g of the distillation residue obtained in step (15-2) and using in the form of a homogeneous solution, heating the thin film distillation apparatus 202 to 220° C., replacing the inside of the thin film distillation apparatus with nitrogen at atmospheric pressure, supplying the solution to the thin film distillation apparatus via supply line 21 at the rate of about 1200 g/hr and carrying out the reaction for 180 hours.

When the reaction liquid was analyzed by liquid chromatography, the reaction liquid was found to contain 15.5% by weight of bis(2-tert-butylphenyl)-4,4'-methylene-dicyclohexyl carbamate. In addition, when the solution recovered from line 27 was analyzed by $^1$H- and $^{13}$C-NMR analysis, the solution was found to contain 99% by weight of 1-butanol.

Step (15-4): Production of 4,4'-methylene-di(cyclohexylisocyanate) by Thermal Decomposition of Bis (2-tert-butylphenyl)-4,4'-methylene-dicyclohexyl Carbamate 287 g of a solution containing 99% by weight of 4,4'-methylene-di(cyclohexylisocyanate) were recovered from line 52 by carrying out the same method as step (5-4) of Example 5 with the exception of heating the thin film distillation apparatus 402 to 210° C., making the pressure in the thin film distillation apparatus about 0.13 kPa, feeding the solution obtained in step (15-3) to feed tank 401, supplying to the thin film distillation apparatus via line 41 at the rate of about 710 g/hr, and carrying out the reaction for 14 hours. The yield based on 4,4'-methylenebis(cyclohexylamine) was 78%.

Example 16

Step (16-1): Production of Dimethyl-4,4'-methylene-dicyclohexyl Carbamate

A solution containing 28.2% by weight of dimethyl-4,4'-methylene-dicyclohexyl carbamate was obtained by carrying out the same method as step (1-1) of Example 1 with the exception of using 1440 g (16.0 mol) of dimethyl carbonate, 336 g (1.6 mol) of 4,4'-methylenebis(cyclohexylamine) and 1.5 g of sodium methoxide (28% methanol solution, Wako Pure Chemical Industries, Ltd.).

Step (16-2): Distillation of Low Boiling Point Component 1271 g of a distillate were obtained by carrying out the same method as step (1-2) of Example 1 with the exception of using the solution obtained in step (16-1) instead of the solution obtained in step (1-1). As a result of analyzing by gas chromatography, the distillate was found to contain 91.3% by weight of dimethyl carbonate and 7.7% by weight of methanol. In addition, as a result of analyzing by liquid chromatography, the distillation residue in the flask was found to contain 99.4% by weight of dibutyl-4,4'-methylene-dicyclohexyl carbamate.

Step (16-3): Production of Bis(2,4-di-tert-amylphenyl)-4,4'-methylene-dicyclohexyl Carbamate by Transesterification 5151 g of a reaction liquid were extracted from line 24 and 88 g of a solution were recovered from line 27 provided in the upper portion of distillation column 203 by carrying out the same method as step (1-3) of Example 1 with the exception of adding 97 g of dibutyl tin dilaurate and 4645 g of 2,4-di-tert-amylphenol to 501 g of the distillation residue obtained in step (16-2) and using in the form of a homogeneous solution, heating the thin film distillation apparatus 202 to 240° C., replacing the inside of the thin film distillation apparatus with nitrogen at atmospheric pressure, supplying the solution to the thin film distillation apparatus via supply line 21 at the rate of about 1200 g/hr and carrying out the reaction for 80 hours.

When the reaction liquid was analyzed by liquid chromatography, the reaction liquid was found to contain 19.5% by weight of bis(2,4-di-tert-amylphenyl)-4,4'-methylene-dicyclohexyl carbamate. In addition, when the solution recovered from line 27 was analyzed by $^1$H- and $^{13}$C-NMR analysis, the solution was found to contain 99% by weight of methanol.

Step (16-4): Production of Hexamethylene Diisocyanate by Thermal Decomposition of Bis(2,4-di-tert-amylphenyl)-4,4'-methylene-dicyclohexyl Carbamate The same method as step (5-4) of Example 5 was carried out with the exception of heating the thin film distillation apparatus 402 to 210° C., making the pressure in the thin film distillation apparatus about 0.13 kPa, feeding the solution obtained in step (16-3) to feed tank 401, supplying to the thin film distillation apparatus via line 41 at the rate of about 680 g/hr, and carrying out the reaction for 16 hours. 323 g of a solution containing 99% by weight of 4,4'-methylene-di(cyclohexylisocyanate) were recovered from line 52. The yield based on 4,4'-methylenebis(cyclohexylamine) was 77%.

Example 17

Step (17-1): Production of Toluene-2,4-dicarbamic Acid Bis(3-methylbutyl)Ester 1818 g (9.0 mol) of bis(3-methylbutyl)carbonate and 220 g (1.8 mol) of 2,4-toluene diamine (Aldrich Corp., USA) were placed in a 5 L volumetric fourth-mouth flask, a stirrer was placed in the flask, and a Dimroth condenser and three-way valve were attached to the flask. After replacing the inside of the system with nitrogen, the four-mouth flask was immersed in an oil bath (OBH-24, Masuda Corp., Japan) heated to 80° C. followed by the addition of 0.35 g of sodium methoxide (28% methanol solution, Wako Pure Chemical Industries, Ltd.) to start the reaction. Samples of the reaction liquid were suitably collected and subjected to NMR analysis, and the reaction was terminated at the point 2,4-toluenediamine was no longer detected. As a result of analyzing the resulting solution by liquid chromatography, the solution was found to contain 29.7% by weight of toluene-2,4-dicarbamic acid bis(3-methylbutyl)ester.

Step (17-2): Distillation of Low Boiling Point Component 1422 g of a distillate were obtained by carrying out the same method as step (1-2) of Example 1 with the exception of using the solution obtained in step (17-1) instead of the solution obtained in step (1-1). As a result of analyzing by gas chromatography, the distillate was found to contain 78.2% by weight of bis(3-methylbutyl)carbonate and 21.2% by weight of 3-methyl-1-butanol. In addition, as a result of analyzing by liquid chromatography, the distillation residue in the flask was found to contain 98.0% by weight of toluene-2,4-dicarbamic acid bis(3-methylbutyl)ester.

Step (17-3): Production of Toluene-2,4-dicarbamic acid bis(2,4-di-tert-amylphenyl)Ester by Transesterification 5258 g of a reaction liquid were extracted from line 24 and 289 g of a solution were recovered from line 27 provided in the upper portion of distillation column 203 by carrying out the same method as step (1-3) of Example 1 with the exception of adding 109 g of dibutyl tin dilaurate and 4835 g of 2,4-di-tert-amylphenol to 615 g of the distillation residue obtained in step (17-2) and using in the form of a homogeneous solution, heating the thin film distillation apparatus 202 to 240° C., replacing the inside of the thin film distillation apparatus with nitrogen at atmospheric pressure, supplying the solution to the thin film distillation apparatus via supply line 21 at the rate of about 1200 g/hr and carrying out the reaction for 70 hours.

When the reaction liquid was analyzed by liquid chromatography, the reaction liquid was found to contain 20.0% by weight of toluene-2,4-dicarbamic acid bis(2,4-di-tert-amylphenyl) ester. In addition, when the solution recovered from line 27 was analyzed by $^1$H- and $^{13}$C-NMR analysis, the solution was found to contain 98% by weight of 3-methyl-1-butanol.

Step (17-4): Production of Toluene-2,4-diisocyanate by Thermal Decomposition of Toluene-2,4-dicarbamic Acid Bis(2,4-di-tert-amylphenyl)Ester The same method as step (1-4) of Example 1 was carried out with the exception of heating the thin film distillation apparatus 302 to 200° C., making the pressure in the thin film distillation apparatus about 1.3 kPa, feeding the solution obtained in step (17-3) to feed tank 301, supplying to the thin film distillation apparatus via line 31 at the rate of about 1000 g/hr, and carrying out the reaction for 15 hours. 267 g of a solution were recovered from line 35, and as a result of analyzing the solution by $^1$H- and $^{13}$C-NMR analysis, the solution was found to contain 99% by weight of toluene-2,4-diisocyanate. The yield based on 2,4-toluene diamine was 85%.

Example 18

Step (18-1): Production of N,N'-(4,4'-methanediyl-diphenyl)-biscarbamic Acid Dibutyl Ester 1774 g (10.2 mol) of dibutyl carbonate and 336 g (1.7 mol) of 4,4'-methylene dianiline (Aldrich Corp., USA) were placed in a 5 L volumetric fourth-mouth flask, a stirrer was placed in the flask, and a Dimroth condenser and three-way valve were attached to the flask. After replacing the inside of the system with nitrogen, the four-mouth flask was immersed in an oil bath (OBH-24, Masuda Corp., Japan) heated to 80° C. followed by the addition of 3.3 g of sodium methoxide (28% methanol solution, Wako Pure Chemical Industries, Ltd.) to start the reaction. Samples of the reaction liquid were suitably collected and subjected to NMR analysis, and the reaction was terminated at the point 4,4'-methylene dianiline was no longer detected. As a result of analyzing the resulting solution by liquid chromatography, the solution was found to contain 30.8% by weight of N,N'-(4,4'-methanediyl-diphenyl)-biscarbamic acid dibutyl ester.

Step (18-2): Distillation of Low Boiling Point Component 1452 g of a distillate were obtained by carrying out the same method as step (1-2) of Example 1 with the exception of using the solution obtained in step (18-1) instead of the solution obtained in step (1-1). As a result of analyzing by gas chromatography, the distillate was found to contain 82.7% by weight of dibutyl carbonate and 16.6% by weight of 1-butanol. In addition, as a result of analyzing by liquid chromatography, the distillation residue in the flask was found to contain 98.5% by weight of N,N'-(4,4'-methanediyl-diphenyl)-biscarbamic acid dibutyl ester.

Step (18-3): Production of N,N'-(4,4'-methanediyl-diphenyl)-biscarbamic Acid Bis(2,4-di-tert-amylphenyl)Ester by Transesterification 4322 g of a reaction liquid were extracted from line 24 and 226 g of a solution were recovered from line 27 provided in the upper portion of distillation column 203 by carrying out the same method as step (1-3) of Example 1 with the exception of adding 103 g of dibutyl tin dilaurate and 3799 g of 2,4-di-tert-amylphenol to 656 g of the distillation residue obtained in step (18-2) and using in the form of a homogeneous solution, heating the thin film distillation apparatus 202 to 240° C., replacing the inside of the thin film distillation apparatus with nitrogen at atmospheric pressure, supplying the solution to the thin film distillation apparatus via supply line 21 at the rate of about 1200 g/hr and carrying out the reaction for 62 hours.

When the reaction liquid was analyzed by liquid chromatography, the reaction liquid was found to contain 25.3% by weight of N,N'-(4,4'-methanediyl-diphenyl)-biscarbamic acid bis(2,4-di-tert-amylphenyl) ester. In addition, when the solution recovered from line 27 was analyzed by $^1$H- and $^{13}$C-NMR analysis, the solution was found to contain 99% by weight of 1-butanol.

Step (18-4): Production of 4,4'-diphenylmethane Diisocyanate by Thermal Decomposition of N,N'-(4,4'-methanediyl-diphenyl)-biscarbamic Acid Bis(2,4-di-tert-amylphenyl)Ester When the thin film distillation apparatus 402 was heated to 210° C., the pressure in the thin film distillation apparatus was made to be about 0.1 kPa, the solution obtained in step (18-3) was fed to feed tank 401, supplied to the thin film distillation apparatus via line 41 at the rate of about 680 g/hr, and the reaction was carried out for 11 hours, 351 g of a solution containing 99% by weight of 4,4'-diphenylmethane diisocyanate were recovered from line 52. The yield based on 4,4'-methylene dianiline was 83%.

Example 19

Step (19-1): Production of N,N'-(4,4'-methanediyl-diphenyl)-biscarbamic Acid Dibutyl Ester A solution containing 26.7% by weight of N,N'-(4,4'-methanediyl-diphenyl)-biscarbamic acid dibutyl ester was obtained by carrying out the same method as step (18-1) of Example 18 with the exception of using 1583 g (9.1 mol) of dibutyl carbonate, 257 g (1.3 mol) of 4,4'-methylene dianiline and 2.5 g of sodium methoxide (28% methanol solution, Wako Pure Chemical Industries, Ltd.).

Step (19-2): Distillation of Low Boiling Point Component 1342 g of a distillate were obtained by carrying out the same method as step (1-2) of Example 1 with the exception of using the solution obtained in step (19-1) instead of the solution obtained in step (1-1). As a result of analyzing by gas chromatography, the distillate was found to contain 85.5% by weight of dibutyl carbonate and 13.6% by weight of 1-butanol. In addition, as a result of analyzing by liquid chromatography, the distillation residue in the flask was found to contain 98.6% by weight of N,N'-(4,4'-methanediyl-diphenyl)-biscarbamic acid dibutyl ester.

Step (19-3): Production of N,N'-(4,4'-methanediyl-diphenyl)-biscarbamic Acid Bis(2,6-dimethylphenyl) Ester by Transesterification 2824 g of a reaction liquid were extracted from line 24 and 160 g of a solution were recovered from line 27 provided in the upper portion of distillation column 203 by carrying out the same method as step (1-3) of Example 1 with the exception of adding 74 g of dibutyl tin dilaurate and 2441 g of 2,6-dimethylphenol to 475 g of the distillation residue obtained in step (19-2) and using in the form of a homogeneous solution, heating the thin film distillation apparatus 202 to 200° C., replacing the inside of the thin film distillation apparatus with nitrogen at atmospheric pressure, supplying the solution to the thin film distillation apparatus via supply line 21 at the rate of about 1200 g/hr and carrying out the reaction for 662 hours.

When the reaction liquid was analyzed by liquid chromatography, the reaction liquid was found to contain 18.9% by weight of toluene-2,4-dicarbamic acid bis(2,6-dimethylphenyl) ester. In addition, when the solution recovered from line 27 was analyzed by $^1$H- and $^{13}$C-NMR analysis, the solution was found to contain 99% by weight of 1-butanol.

Step (19-4): Production of 4,4'-diphenylmethane Diisocyanate by Thermal Decomposition of N,N'-(4,4'-methanediyl-diphenyl)-biscarbamic Acid Bis(2,6-dimethylphenyl)Ester 244 g of a solution containing 99% by weight of 4,4'-diphenylmethane diisocyanate was recovered from line 52 by carrying out the same method as step (5-4) of Example 5 with the exception of heating the thin film distillation apparatus 402 to 210° C., making the pressure in the thin film distillation apparatus to be about 0.1 kPa, feeding the solution obtained in step (19-3) to feed tank 401, supplying to the thin film distillation apparatus via line 41 at the rate of about 700 g/hr, and carrying out the reaction for 13 hours. The yield based on 4,4'-methylene dianiline was 75%.

Example 20

Step (20-1): Production of N,N'-hexanediyl-bis-carbamic Acid Dibutyl Ester

A solution containing 22.7% by weight of N,N'-hexanediyl-bis-carbamic acid dibutyl ester was obtained by carrying out the same method as step (1-1) of Example 1 with the exception of using 2192 g (12.6 mol) of dibutyl carbonate, 209 g (1.8 mol) of hexamethylene diamine and 3.5 g of sodium methoxide (28% methanol solution, Wako Pure Chemical Industries, Ltd.).

Step (20-2): Distillation of Low Boiling Point Component 1845 g of a distillate were obtained by carrying out the same method as step (1-2) of Example 1 with the exception of using the solution obtained in step (20-1) instead of the solution obtained in step (1-1). As a result of analyzing by gas chromatography, the distillate was found to contain 85.9% by weight of dibutyl carbonate and 13.6% by weight of 1-butanol. In addition, as a result of analyzing by liquid chromatography, the distillation residue in the flask was found to contain 98.6% by weight of N,N'-(4,4'-methanediyl-diphenyl)-biscarbamic acid dibutyl ester.

Step (20-3): Production of N,N'-hexanediyl-bis-carbamic Acid Di(2,6-di-tert-butylphenyl)Ester by Transesterification 5395 g of a reaction liquid were extracted from line 24 and 206 g of a solution were recovered from line 27 provided in the upper portion of distillation column 203 by carrying out the same method as step (1-3) of Example 1 with the exception of obtaining a homogeneous solution of 550 g of the distillation residue obtained in step (20-3), 109 g of dibutyl tin dilaurate and 4950 g of 2,6-di-tert-butylphenol, heating the thin film distillation apparatus 202 to 240° C., and carrying out the reaction for 86 hours.

When the reaction liquid was analyzed by liquid chromatography, the reaction liquid was found to contain 14.9% by weight of N,N'-hexanediyl-bis-carbamic acid di(2,6-di-tert-butylphenyl) ester. In addition, when the solution recovered from line 27 was analyzed by $^1$H- and $^{13}$C-NMR analysis, the solution was found to contain 99% by weight of 1-butanol.

Step (20-4): Production of Hexamethylene Diisocyanate by Thermal Decomposition of N,N'-hexanediyl-bis-carbamic Acid Di(2,6-di-tert-butylphenyl)Ester The same method as step (1-4) of Example 1 was carried out with the exception of heating the thin film distillation apparatus 302 was heated to 200° C., making the pressure in the thin film distillation apparatus to be about 1.3 kPa, feeding the solution obtained in step (20-3) was fed to feed tank 301, supplying to the thin film distillation apparatus via line 31 at the rate of about 980 g/hr, and carrying out the reaction for 13 hours. 210 g of a solution were recovered from line 35. As a result of analyzing the solution by $^1$H- and $^{13}$C-NMR analysis, the solution was found to contain 99% by weight of hexamethylene diisocyanate. The yield based on hexamethylene diamine was 70%.

Example 21

Step (21-1): Production of N,N'-hexanediyl-bis-carbamic Acid Di(3-methylbutyl)Ester A solution containing 24.0% by weight of N,N'-hexanediyl-bis-carbamic acid di(3-methylbutyl)ester was obtained by carrying out the same method as step (1-1) of Example 1 with the exception of using 2290 g (11.3 mol) of bis(3-methylbutyl)carbonate, 208.8 g (1.8 mol) of hexamethylene diamine and 3.5 g of sodium methoxide (28% methanol solution, Wako Pure Chemical Industries, Ltd.).

Step (21-2): Distillation of Low Boiling Point Component 1891 g of a distillate were obtained by carrying out the same method as step (1-2) of Example 1 with the exception of using the solution obtained in step (21-1) instead of the solution obtained in step (1-1). As a result of analyzing by gas chromatography, the distillate was found to contain 83.6% by weight of bis(3-methylbutyl)carbonate and 16.1% by weight of 3-methyl-1-butanol. In addition, as a result of analyzing by liquid chromatography, the distillation residue in the flask was found to contain 98.6% by weight of N,N'-hexanediyl-bis-carbamic acid di(3-methylbutyl)ester.

Step (21-3): Production of N,N'-hexanediyl-bis-carbamic Acid Di(2-phenylphenyl)Ester by Transesterification 3977 g of a reaction liquid were extracted from line 24 and 276 g of a solution were recovered from line 27 provided in the upper portion of distillation column 203 by carrying out the same method as step (1-3) of Example 1 with the exception of adding 110 g of dibutyl tin dilaurate and 3545 g of 2-phenylphenol to 606 g of the distillation residue obtained in step (21-2) and using in the form of a homogeneous solution, heating the thin film distillation apparatus 202 to 240° C., replacing the inside of the thin film distillation apparatus with nitrogen at atmospheric pressure, supplying the solution to the thin film distillation apparatus via supply line 21 at the rate of about 1200 g/hr and carrying out the reaction for 80 hours.

When the reaction liquid was analyzed by liquid chromatography, the reaction liquid was found to contain 20.0% by weight of N,N'-hexanediyl-bis-carbamic acid di(2-phenylphenyl) ester. In addition, when the solution recovered from line 27 was analyzed by $^1$H- and $^{13}$C-NMR analysis, the solution was found to contain 99% by weight of 3-methyl-1-butanol.

Step (21-4): Production of Hexamethylene Diisocyanate by Thermal Decomposition of N,N'-hexanediyl-bis-carbamic Acid Di(2-phenylphenyl)Ester 241 g of a solution were recovered from line 35 by carrying out the same method as step (1-4) of Example 1 with the exception of heating the thin film distillation apparatus 302 to 200° C., making the pressure in the thin film distillation apparatus to be about 1.3 kPa, feeding the solution obtained in step (21-3) to feed tank 301, supplying to the thin film distillation apparatus via line 31 at the rate of about 980 g/hr, and carrying out the reaction for 13 hours. As a result of analyzing the solution by $^1$H- and $^{13}$C-NMR analysis, the solution was found to contain 99% by weight of hexamethylene diisocyanate. The yield based on hexamethylene diamine was 80%.

Example 22

Step (22-1): Production of N,N'-hexanediyl-bis-carbamic Acid Di(3-methylbutyl)Ester A solution containing 23.8% by weight of N,N'-hexanediyl-bis-carbamic acid di(3-methylbutyl)ester was obtained by carrying out the same method as step (1-1) of Example 1 with the exception of using 2163 g (10.7 mol) of bis(3-methylbutyl)carbonate, 197 g (1.7 mol) of hexamethylene diamine and 3.3 g of sodium methoxide (28% methanol solution, Wako Pure Chemical Industries, Ltd.).

Step (22-2): Distillation of Low Boiling Point Component 1783 g of a distillate were obtained by carrying out the same method as step (1-2) of Example 1 with the exception of using the solution obtained in step (22-1) instead of the solution obtained in step (1-1). As a result of analyzing by gas chromatography, the distillate was found to contain 83.5% by weight of bis(3-methylbutyl)carbonate and 16.0% by weight of 3-methyl-1-butanol. In addition, as a result of analyzing by liquid chromatography, the distillation residue in the flask was found to contain 97.1% by weight of N,N'-hexanediyl-bis-carbamic acid di(3-methylbutyl)ester.

Step (22-3): Production of N,N'-hexanediyl-bis-carbamic Acid Di(2,4-bis(α,α-dimethylbenzyl)phenyl) Ester by Transesterification 4689 g of a reaction liquid were extracted from line 24 and 259 g of a solution were recovered from line 27 provided in the upper portion of distillation column 203 by carrying out the same method as step (1-3) of Example 1 with the exception of adding 103 g of dibutyl tin dilaurate and 4385 g of 2,4-bis(α,α-dimethylbenzyl)phenol (Aldrich Corp., USA) to 575 g of the distillation residue obtained in step (22-2) and using in the form of a homogeneous solution, heating the thin film distillation apparatus 202 to 240° C., replacing the inside of the thin film distillation apparatus with nitrogen at atmospheric pressure, supplying the solution to the thin film distillation apparatus via supply line 21 at the rate of about 1200 g/hr and carrying out the reaction for 80 hours.

When the reaction liquid was analyzed by liquid chromatography, the reaction liquid was found to contain 25.8% by weight of N,N'-hexanediyl-bis-carbamic acid di(2,4-bis(α,α-dimethylbenzyl)phenyl ester. In addition, when the solution recovered from line 27 was analyzed by $^1$H- and $^{13}$C-NMR analysis, the solution was found to contain 99% by weight of 3-methyl-1-butanol.

Step (22-4): Production of Hexamethylene Diisocyanate by Thermal Decomposition of N,N'-hexanediyl-bis-carbamic Acid Di(2,4-bis(α-dimethylbenzyl)phenyl)Ester 220 g of a solution were recovered from line 35 by carrying out the same method as step (1-4) of Example 1 with the exception of heating the thin film distillation apparatus 302 to 200° C., making the pressure in the thin film distillation apparatus to be about 1.3 kPa, feeding the solution obtained in step (22-3) to feed tank 301, supplying to the thin film distillation apparatus via line 31 at the rate of about 980 g/hr, and carrying out the reaction for 18 hours. As a result of analyzing the solution by $^1$H- and $^{13}$C-NMR analysis, the solution was found to contain 99% by weight of hexamethylene diisocyanate. The yield based on hexamethylene diamine was 77%.

Example 23

Figure 5:
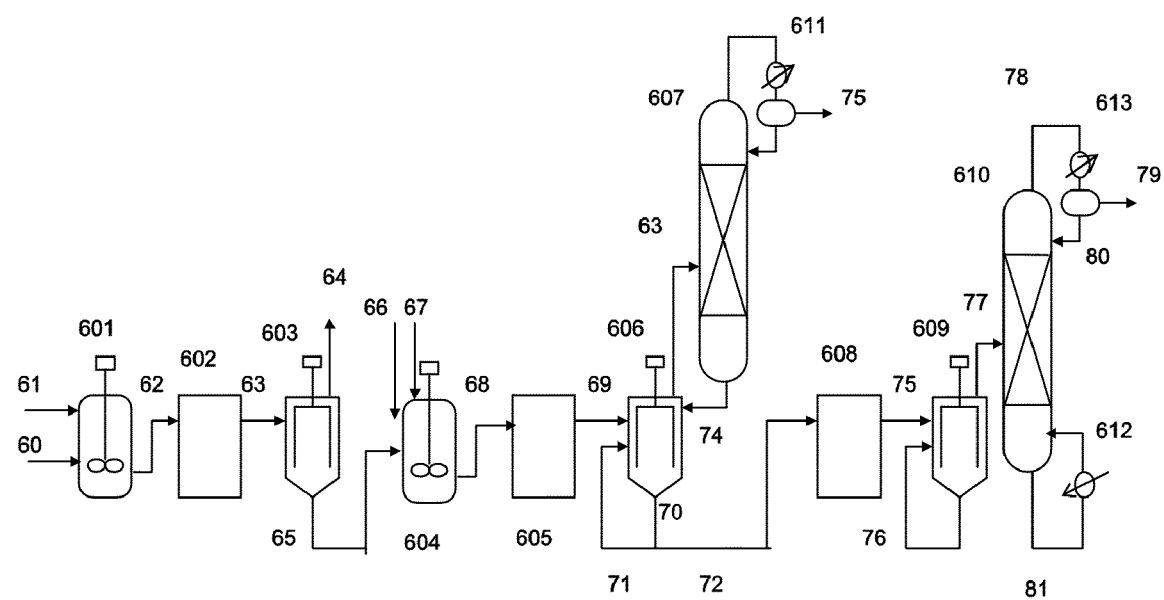
FIG. 5 shows a conceptual drawing showing an isocyanate production apparatus according to an embodiment of the present invention.
Figure 6:
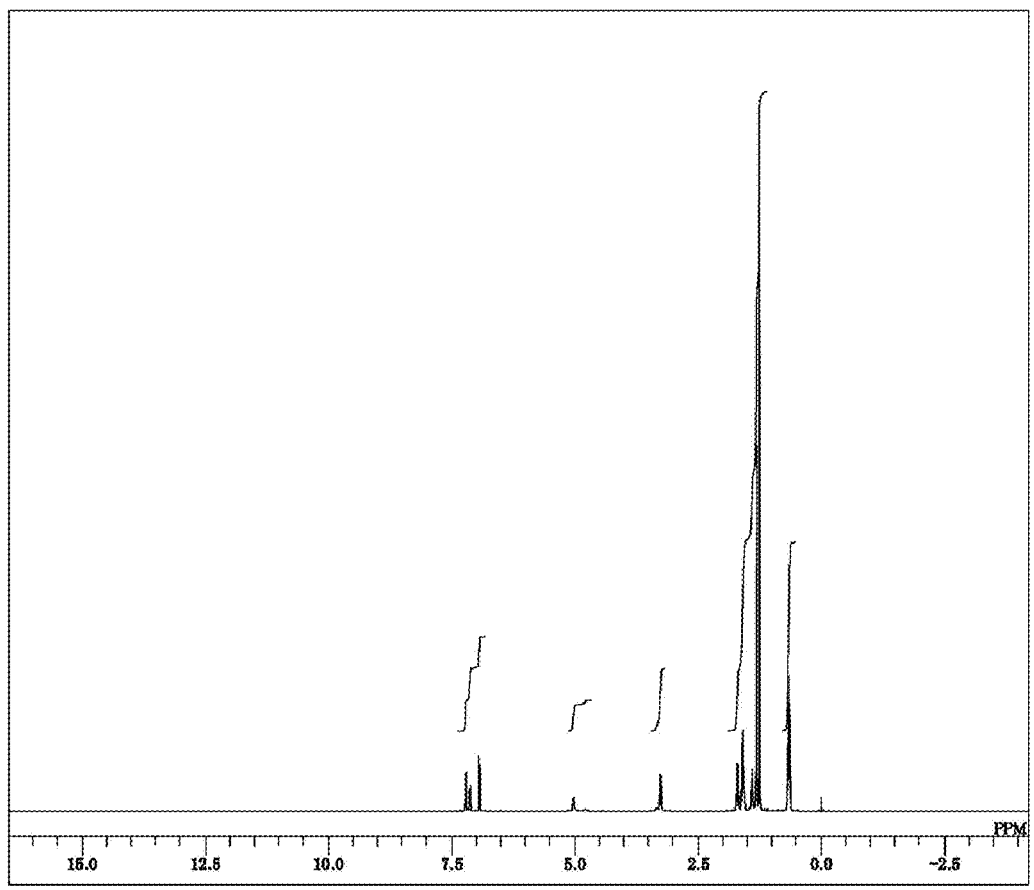
FIG. 6 shows the $^1$H-NMR spectrum of N,N'-hexanediyl-bis-carbamic acid di(2,4-di-tert-butylphenyl) ester obtained in step (3-4) of Example 3 of the present invention; and, FIG. 7 shows the $^{13}$C-NMR spectrum of N,N'-hexanediyl-bis-carbamic acid di(2,4-di-tert-butylphenyl) ester obtained in step (3-4) of Example 3 of the present invention.
Figure 7:
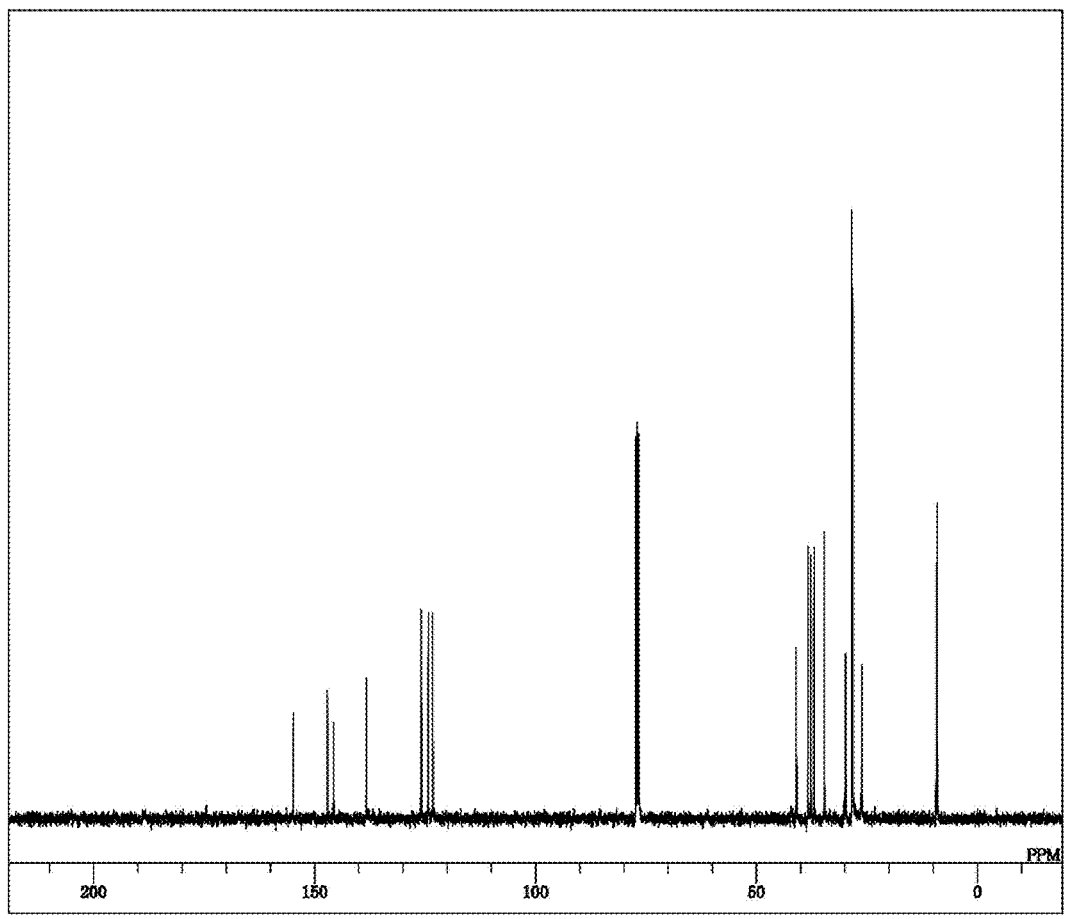

Hexamethylene diisocyanate was produced in a reaction apparatus like that shown in FIG. 5.

Step (23-1): Production Process of N,N'-hexanediyl-bis-carbamic Acid Di(3-methylbutyl)Ester A stirring tank 601 (internal volume: 5 L) was heated to 80° C. Bis(3-methylbutyl)carbonate was transferred to the stirring tank 601 from a line 60 at the rate of 678 g/hr with a line 62 closed, and a mixed solution of hexamethylene diamine, 3-methyl-1-butanol and sodium methoxide (28% methanol solution) (mixing ratio: hexamethylene diamine 50 parts/3-methyl-1-butanol 50 parts/sodium methoxide 0.42 parts) was simultaneously transferred from a line 61 at the rate of 112 g/hr. After 4 hours, line 62 was opened with a line 63 closed, and transfer of the reaction liquid to a tank 602 was started at the rate of 790 g/hr. Line 62 was maintained at 80° C. to prevent precipitation of solids from the reaction liquid.

When the reaction liquid transferred to a line 602 was analyzed by liquid chromatography, the reaction liquid was found to contain 20.3% by weight of N,N'-hexanediyl-bis-carbamic acid di(3-methylbutyl)ester.

Step (23-2): Low Boiling Point Component Distillation Process

A thin film distillation apparatus 603 (heat-conducting surface area of 0.2 m$^2$, Kobelco Eco-Solutions Co., Ltd., Japan) was heated to 150° C. and the pressure inside the apparatus was made to be about 0.02 kPa.

The solution stored in tank 602 was transferred to thin film distillation apparatus 603 from line 63 at the rate of 790 g/hr where a low boiling point component contained in the solution were distilled off. The low boiling point component that had been distilled off was extracted from the thin film distillation apparatus 603 via a line 64. On the other hand, a high boiling point component was extracted from the thin film distillation apparatus 603 via a line 65 maintained at 150° C., and transferred to a stirring tank 604 maintained at 120° C. At the same time, 2,4-di-tert-amylphenol was transferred via a line 66 to stirring tank 604 at the rate of 1306 g/hr, and dibutyl tin dilaurate was transferred to stirring tank 604 via a line 67 at the rate of 29 g/hr.

The mixed liquid prepared in stirring tank 604 was transferred to a tank 605 via a line 68 with a line 69 closed, and stored in the tank 605. When the solution stored in the tank 605 was analyzed by liquid chromatography, the solution was found to contain 10.7% by weight of N,N'-hexanediyl-bis-carbamic acid di(3-methylbutyl)ester.

Step (23-3): Production Process of N,N'-hexanediyl-bis-carbamic Acid Di(2,4-di-tert-amylphenyl)Ester by Transesterification A thin film distillation apparatus 606 (heat-conducting surface area of 0.2 m², Kobelco Eco-Solutions Co., Ltd., Japan) was heated to 240° C.

A transesterification reaction was carried out by transferring a mixed liquid of N,N'-hexanediyl-bis-carbamic acid di(3-methylbutyl)ester, 2,4-di-tert-amylphenol and dibutyl tin dilaurate stored in tank 605 to thin film distillation apparatus 606 via a line 69 at the rate of 1496 g/hr with a line 72 closed. A mixed gas containing 3-methyl-1-butanol and 2,4-di-tert-amylphenol was extracted from a line 73 provided in the upper portion of the thin film distillation apparatus 606, and supplied to a distillation column 607. The 3-methyl-1-butanol and 2,4-di-tert-amylphenol were separated in the distillation column 607, and the 2,4-di-tert-amylphenol was returned to the upper portion of thin film distillation apparatus 606 via a line 74 provided in the bottom of distillation column 607. A reaction liquid was extracted from a line 70 provided in the bottom of the thin film distillation apparatus 606, and supplied to thin film distillation apparatus 606 via a line 71. When the N,N'-hexanediyl-bis-carbamic acid di(2,4-di-tert-amylphenyl) ester in the reaction liquid extracted from line 70 reached 20.3% by weight, line 72 was opened with line 75 closed and the reaction liquid was transferred to a tank 608.

Step (23-4): Production Process of Hexamethylene Diisocyanate by Thermal Decomposition of N,N'-hexanediyl-bis-carbamic Acid Di(2,4-di-tert-amylphenyl)Ester The solution stored in tank 608 was supplied to a thin film distillation apparatus 609 (heat-conducting surface area of 0.2 m², Kobelco Eco-Solutions Co., Ltd., Japan) heated to 200° C. and set to an internal pressure of about 1.3 kPa via line 75 at the rate of 1395 g/hr. A gaseous component containing hexamethylene diisocyanate was extracted from a line 77 provided in the upper portion of the thin film distillation apparatus 609 and supplied to a distillation column 610. Distillative separation was carried out in distillation column 610, and hexamethylene diisocyanate was recovered from a line 79 at the rate of 72 g/hr.

Comparative Example 1

Step (A-1): Production of N,N'-hexanediyl-bis-carbamic Acid Dimethyl Ester 1044 g of a solution containing 29.6% by weight of N,N-hexanediyl-bis-carbamic acid methyl ester were obtained by carrying out the same method as step (1-1) of Example 1 with the exception of using 882 g (9.8 mol) of dimethyl carbonate and 162 g (1.4 mol) of hexamethylene diamine, adding a stirrer, and using 2.7 g of sodium methoxide.

Step (A-2): Distillation of Low Boiling Point Component 729 g of a distillate were obtained by carrying out the same method as step (1-2) of Example 1 with the exception of using the solution obtained in step (A-1) instead of the solution obtained in step (1-1). As a result of analyzing by gas chromatography, the distillate was found to contain 87.5% by weight of dimethyl carbonate and 11.7% by weight of methanol. As a result of analyzing by liquid chromatography, the distillation residue in the flask was found to contain 98.2% by weight of N,N'-hexanediyl-bis-carbamic acid dimethyl ester.

Step (A-3): Production of N,N'-hexanediyl-bis-carbamic Acid Diphenyl Ester by Transesterification 4101 g of a reaction liquid were extracted from line 24 and 65 g of a solution were recovered from line 27 provided in the upper portion of distillation column 203 by carrying out the same method as step (1-3) of Example 1 with the exception of using 316 g of the distillation residue obtained in step (A-2) instead of the distillation residue obtained in step (1-2), using 85 g of dibutyl tin dilaurate and 3770 g of phenol (for nucleic acid extraction, Wako Pure Chemical Industries, Ltd., Japan), setting the heating unit of the thin film distillation apparatus to 180° C. and carrying out the reaction for 430 hours. The extracted reaction liquid contained 8.7% by weight of N,N'-hexanediyl-bis-carbamic acid diphenyl ester.

Step (A-4): Production of Hexamethylene Diisocyanate by Thermal Decomposition of N,N'-hexanediyl-bis-carbamic Acid Diphenyl Ester The same method as step (5-4) of Example 5 was carried out with the exception of heating thin film distillation apparatus 402 to 200° C., making the pressure inside the thin film distillation apparatus about 1.3 kPa, feeding the solution obtained in step (A-3) to feed tank 401, supplying to the thin film distillation apparatus via line 41 at the rate of about 680 g/hr, and carrying out the reaction for 11 hours. 134 g of a solution containing 99% by weight of hexamethylene diisocyanate was recovered from line 47. The yield based on hexamethylene diamine was 57%. In addition, a black solid was adhered to the sidewalls of the thin film distillation apparatus 402 following completion of step (A-4).

Comparative Example 2

Step (B-1): Production of N,N'-hexanediyl-bis-carbamic Acid Di(3-methylbutyl)Ester 2146 g of a solution containing 23.1% by weight of N,N-hexanediyl-bis-carbamic acid di(3-methylbutyl)ester were obtained by carrying out the same method as step (1-1) of Example 1 with the exception of using 1970 g (9.8 mol) of bis(3-methylbutyl)carbonate and 174 g (1.5 mol) of hexamethylene diamine, adding a stirrer, and using 2.9 g of sodium methoxide.

Step (B-2): Distillation of Low Boiling Point Component 1631 g of a distillate were obtained by carrying out the same method as step (1-2) of Example 1 with the exception of using the solution obtained in step (B-1) instead of the solution obtained in step (1-1). As a result of analyzing by gas chromatography, the distillate was found to contain 84.2% by weight of bis(3-methylbutyl)carbonate and 15.4% by weight of 3-methyl-1-butanol. In addition, as a result of analyzing by liquid chromatography, the distillation residue in the flask was found to contain 96.7% by weight of N,N'-hexanediyl-bis-carbamic acid bis(3-methylbutyl)ester.

Step (B-3): Production of N,N'-hexanediyl-bis-carbamic Acid Di(4-methylphenyl)Ester by Transesterification 4978 g of a reaction liquid were extracted from line 24 and 185 g of a solution were recovered from line 27 provided in the upper portion of distillation column 203 by carrying out the same method as step (1-3) of Example 1 with the exception of using 510 g of the distillation residue obtained in step (B-2) instead of the distillation residue obtained in step (1-2), using 91 g of dibutyl tin dilaurate and 4645 g of 4-methylphenol (Aldrich Corp., USA), and carrying out the reaction for 58 hours. The extracted reaction liquid contained 8.1% by weight of N,N'-hexanediyl-bis-carbamic acid di(4-methylphenyl) ester.

Step (B-4): Production of Hexamethylene Diisocyanate by Thermal Decomposition of N,N'-hexanediyl-bis-carbamic Acid Di(4-methylphenyl)Ester A thermal decomposition reaction was carried out in a reaction apparatus like that shown in FIG. 4.

Thin film distillation apparatus 402 (Kobelco Eco-Solutions Co., Ltd., Japan) having a heat-conducting surface area of 0.2 m$^2$ was heated to 200° C. and the pressure inside the thin film distillation apparatus was made to be about 1.3 kPa. The solution obtained in step (B-3) was fed to feed tank 401 and supplied to the thin film distillation apparatus via line 41 at the rate of about 680 g/hr. A liquid component was extracted from line 43 provided in the bottom of the thin film distillation apparatus 402, and returned to feed tank 401 via line 44. A gaseous component containing hexamethylene diisocyanate and 4-methylphenol was extracted from line 42 provided in the upper portion of thin film distillation apparatus 402. The gaseous component was fed to distillation column 403 where the hexamethylene diisocyanate and 4-methylphenol were separated, the 4-methylphenol was extracted from line 45 connected to the top of distillation column 403, the hexamethylene diisocyanate was extracted from line 47 provided at an intermediate stage of distillation column 403, a high boiling point substance was extracted from line 46 provided in the bottom of distillation column 403, and a portion was returned to feed tank 401 via line 44. When the reaction was carried out for 11 hours, 114 g of a solution containing 99% by weight of hexamethylene diisocyanate was recovered from line 47. The yield based on hexamethylene diamine was 57%. In addition, a black solid was adhered to the sidewalls of the thin film distillation apparatus 402 following completion of step (B-4).

Comparative Example 3

Step (C-1): Production of N,N'-hexanediyl-bis-carbamic Acid Dibutyl Ester 1818 g (10.5 mol) of dibutyl carbonate produced using the method of Reference Example 2 and 220 g (1.9 mol) of hexamethylene diamine were placed in a 5 L volumetric fourth-mouth flask, a stirrer was placed in the flask, and a Dimroth condenser and three-way valve were attached to the flask. After replacing the inside of the system with nitrogen, the four-mouth flask was immersed in an oil bath (OBH-24, Masuda Corp.) heated to 80° C. followed by the addition of 3.7 g of sodium methoxide (28% methanol solution, Wako Pure Chemical Industries, Ltd.) to start the reaction. Samples of the reaction liquid were suitably collected and subjected to NMR analysis, and the reaction was terminated at the point hexamethylene diamine was no longer detected. As a result of analyzing the resulting solution by liquid chromatography, the solution was found to contain 28.3% by weight of N,N'-hexanediyl-bis-carbamic acid dibutyl ester.

Step (C-2): Distillation of Low Boiling Point Component 1444 g of a distillate were obtained by carrying out the same method as step (1-2) of Example 1 with the exception of using the solution obtained in step (C-1) instead of the solution obtained in step (1-1). As a result of analyzing by gas chromatography, the distillate was found to contain 80.9% by weight of dibutyl carbonate and 18.6% by weight of 1-butanol. In addition, as a result of analyzing by liquid chromatography, the distillation residue in the flask was found to contain 98.0% by weight of N,N'-hexanediyl-bis-carbamic acid dibutyl ester.

Step (C-3): Production of N,N'-hexanediyl-bis-carbamic Acid Di(4-octylphenyl)Ester by Transesterification 6122 g of a reaction liquid were extracted from line 24 and 182 g of a solution were recovered from line 27 provided in the upper portion of distillation column 203 by carrying out the same method as step (1-3) of Example 1 with the exception of using 594 g of the distillation residue obtained in step (6-3) instead of the distillation residue obtained in step (1-2), adding 114 g of dibutyl tin dilaurate and 5611 g of 4-octylphenol and using in the form of a homogeneous solution, feeding to feed tank 201, heating the thin film distillation apparatus 202 having a heat-conducting surface area of 0.2 m$^2$ to 240° C., and carrying out the reaction for 86 hours.

When the extracted reaction liquid was analyzed by liquid chromatography, the reaction liquid was found to contain 11.5% by weight of N,N'-hexanediyl-bis-carbamic acid di(4-octylphenyl) ester. In addition, when the solution recovered from line 27 was analyzed by $^1$H- and $^{13}$C-NMR analysis, the solution was found to contain 99.0% by weight of 1-butanol.

Step (C-4): Production of Hexamethylene Diisocyanate by Thermal Decomposition of N,N'-hexanediyl-bis-carbamic Acid Di(4-octylphenyl)Ester A thermal decomposition reaction was carried out in a reaction apparatus like that shown in FIG. 3.

Thin film distillation apparatus 302 having a heat-conducting surface area of 0.2 m² was heated to 200° C. and the pressure inside the thin film distillation apparatus was made to be about 1.3 kPa. The solution obtained in step (C-3) was fed to feed tank 301 and supplied to the thin film distillation apparatus via line 31 at the rate of about 980 g/hr. A liquid component was extracted from line 33 provided in the bottom of the thin film distillation apparatus 302, and returned to feed tank 301 via line 34. A gaseous component containing hexamethylene diisocyanate and 4-octylphenol was extracted from line 32 provided in the upper portion of thin film distillation apparatus 302. The gaseous component was fed to distillation column 303 where the hexamethylene diisocyanate and 4-octylphenol were separated, and a portion of 4-octylphenol was returned to feed tank 301 through line 34 via line 36 provided in the bottom of distillation column 303. When the reaction was carried out for 13 hours, 167 g of a solution were recovered from line 35, and as a result of analyzing the solution by $^1$H- and $^{13}$C-NMR analysis, the solution was found to contain 99% by weight of hexamethylene diisocyanate. The yield based on hexamethylene diamine was 53%. In addition, a black solid was adhered to the sidewalls of the thin film distillation apparatus 302 following completion of step (C-4).

Comparative Example 4

Step (D-1): Production of
N,N'-hexanediyl-bis-carbamic Acid Dibutyl Ester 1914 g (11.0 mol) of dibutyl carbonate produced using the method of Reference Example 2 and 232 g (2.0 mol) of hexamethylene diamine were placed in a 5 L volumetric fourth-mouth flask, a stirrer was placed in the flask, and a Dimroth condenser and three-way valve were attached to the flask. After replacing the inside of the system with nitrogen, the four-mouth flask was immersed in an oil bath heated to 80° C. followed by the addition of 0.37 g of sodium methoxide (28% methanol solution, Wako Pure Chemical Industries, Ltd.) to start the reaction. Samples of the reaction liquid were suitably collected and subjected to NMR analysis, and the reaction was terminated at the point hexamethylene diamine was no longer detected. As a result of analyzing the resulting solution by liquid chromatography, the solution was found to contain 28.3% by weight of N,N'-hexanediyl-bis-carbamic acid dibutyl ester.

Step (D-2): Distillation of Low Boiling Point
Component 1532 g of a distillate were obtained by carrying out the same method as step (1-2) of Example 1 with the exception of using the solution obtained in step (D-1) instead of the solution obtained in step (1-1). As a result of analyzing by gas chromatography, the distillate was found to contain 80.9% by weight of dibutyl carbonate and 18.5% by weight of 1-butanol. In addition, as a result of analyzing by liquid chromatography, the distillation residue in the flask was found to contain 99.5% by weight of N,N'-hexanediyl-bis-carbamic acid dibutyl ester.

Step (D-3): Production of
N,N'-hexanediyl-bis-carbamic Acid
Di(3-octyloxy)Ester by Transesterification 4203 g of a reaction liquid were extracted from line 24 and 250 g of a solution were recovered from line 27 provided in the upper portion of distillation column 203 by carrying out the same method as step (1-3) of Example 1 with the exception of using 605 g of the distillation residue obtained in step (6-3) instead of the distillation residue obtained in step (1-2), adding 120 g of dibutyl tin dilaurate and 3727 g of 3-octanol (Aldrich Corp., USA) and using in the form of a homogeneous solution, feeding to feed tank 201, heating the thin film distillation apparatus 202 having a heat-conducting surface area of 0.2 m² to 175° C., and carrying out the reaction for 180 hours.

When the extracted reaction liquid was analyzed by liquid chromatography, the reaction liquid was found to contain 17.1% by weight of N,N'-hexanediyl-bis-carbamic acid di(3-octyloxy) ester. In addition, when the solution recovered from line 27 was analyzed by $^1$H- and $^{13}$C-NMR analysis, the solution was found to contain 99.0% by weight of 1-butanol.

Step (D-4): Production of Hexamethylene
Diisocyanate by Thermal Decomposition of
N,N'-hexanediyl-bis-carbamic Acid
Di(3-octyloxy)Ester A thermal decomposition reaction was carried out in a reaction apparatus like that shown in FIG. 4.

Thin film distillation apparatus 402 (Kobelco Eco-Solutions Co., Ltd., Japan) having a heat-conducting surface area of 0.2 m² was heated to 200° C. and the pressure inside the thin film distillation apparatus was made to be about 1.3 kPa. The solution obtained in step (D-3) was fed to feed tank 401 and supplied to the thin film distillation apparatus via line 41 at the rate of about 680 g/hr. A liquid component was extracted from line 43 provided in the bottom of the thin film distillation apparatus 402, and returned to feed tank 401 via line 44. A gaseous component containing hexamethylene diisocyanate and 3-octanol was extracted from line 42 provided in the upper portion of thin film distillation apparatus 402. The gaseous component was fed to distillation column 403 where the hexamethylene diisocyanate and 3-octanol were separated, the 3-octanol was extracted from line 45 connected to the top of distillation column 403, hexamethylene diisocyanate was extracted from line 47 provided in an intermediate stage of distillation column 403, a high boiling point substance was extracted from line 46 provided in the bottom of distillation column 403, and a portion was returned to feed tank 401 via line 44. When the reaction was carried out for 11 hours, 149 g of a solution containing 99% by weight of hexamethylene diisocyanate were recovered from line 47. The yield based on hexamethylene diamine was 45%. In addition, a black solid was adhered to the sidewalls of the thin film distillation apparatus 402 following completion of step (D-4).

INDUSTRIAL APPLICABILITY

Since the isocyanate production process according to the present invention enables isocyanates to be efficiently produced without using extremely toxic phosgene, the production process of the present invention is extremely useful industrially and has high commercial value.

The invention claimed is:
1. A process for producing an isocyanate, comprising the steps of:
reacting a carbamic acid ester and an aromatic hydroxy compound to obtain an aryl carbamate having a group derived from the aromatic hydroxy compound; and
subjecting the aryl carbamate to a decomposition reaction, wherein the aromatic hydroxy compound is an aromatic hydroxy compound which is represented by the following formula (1) and which has a substituent R1 at least one ortho position of a hydroxyl group:

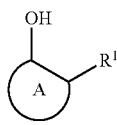

(1)

(wherein ring A represents an aromatic hydrocarbon ring in a form of a single or multiple rings which may have a substituent and which have 6 to 20 carbon atoms;

R1 represents a group other than a hydrogen atom in a form of an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the group containing an atom selected from a carbon atom, an oxygen atom and a nitrogen atom; and R1 may bond with A to form a ring structure).

2. The process according to claim 1, wherein the aromatic hydroxy compound is a compound represented by the following formula (2):

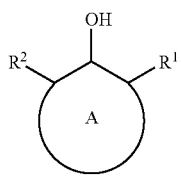

(2)

(wherein ring A and R1 are the same as defined above,

R2 represents a hydrogen atom or an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or aralkyloxy group having 7 to 20 atoms, the aliphatic alkyl, the aliphatic alkoxy, the aryl, the aryloxy, the aralkyl and the aralkyloxy groups containing an atom selected from a carbon atom, an oxygen atom and a nitrogen atom, and R2 may bond with A to form a ring structure).

3. The process according to claim 2, wherein in the formula (2), a total number of the carbon atoms constituting R1 and R2 is 2 to 20.

4. The process according to claim 1, wherein the ring A of the aromatic hydroxy compound comprises a structure containing at least one structure selected from the group consisting of a benzene ring, a naphthalene ring and an anthracene ring.

5. The process according to claim 4, wherein the aromatic hydroxy compound is a compound represented by the following formula (3):

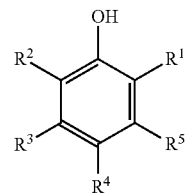

(3)

(wherein R1 and R2 are the same as defined above, and each of R3, R4 and R5 independently represents a hydrogen atom or an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the aliphatic alkyl, the aliphatic alkoxy, the aryl, the aryloxy, the aralkyl and the aralkyloxy groups containing an atom selected from a carbon atom, an oxygen atom and a nitrogen atom).

6. The process according to claim 5, wherein the aromatic hydroxy compound is such that in the formula (3), each of R1 and R4 independently represents a group represented by the following formula (4), and R2, R3 and R5 represent a hydrogen atom:

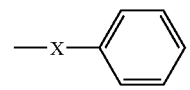

(4)

(wherein X represents a branched structure selected from the structures represented by the following formulas (5) and (6):

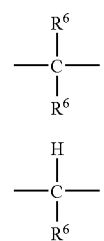

(5)

(6)

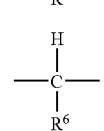

(wherein R6 represents a linear or branched alkyl group having 1 to 3 carbon atoms).

7. The process according to claim 5, wherein the aromatic hydroxy compound is such that in the formula (3), R1 represents a linear or branched alkyl group having 1 to 8 carbon atoms, and each of R2 and R4 independently represents a hydrogen atom or a linear or branched alkyl group having 1 to 8 carbon atoms.

8. The process according to claim 1, wherein the carbamic acid ester is an aliphatic carbamic acid ester, and a low boiling point component formed with the aryl carbamate is an aliphatic alcohol.

9. The process according to claim 8, wherein the aliphatic carbamic acid ester is an aliphatic polycarbamic acid ester.

10. The process according to claim 8, further comprising the steps of:
continuously supplying the aliphatic carbamic acid ester and the aromatic hydroxy compound to a reaction vessel so as to react the aliphatic carbamic acid ester and the aromatic hydroxy compound inside the reaction vessel;
recovering a formed low boiling point component in a form of a gaseous component; and
continuously extracting a reaction liquid containing the aryl carbamate and the aromatic hydroxy compound from a bottom of the reaction vessel.

11. The process according to claim 1, wherein the decomposition reaction is a thermal decomposition reaction, and is a reaction in which a corresponding isocyanate and aromatic hydroxy compound are formed from the aryl carbamate.

12. The process according to claim 11, wherein at least one compound of the isocyanate and aromatic hydroxy compound formed by the thermal decomposition reaction of the aryl carbamate is recovered in a form of a gaseous component.

13. The process according to claim 8, wherein the aliphatic carbamic acid ester is a compound represented by the following formula (7):

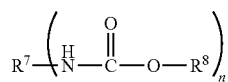
(7)

(wherein R7 represents a group selected from the group consisting of an aliphatic group having 1 to 20 carbon atoms and an aromatic group having 6 to 20 carbon atoms, the group containing an atom selected from a carbon atom, an oxygen atom and a nitrogen atoms, and having a valence of n,
R8 represents an aliphatic group which has 1 to 8 carbon atoms and which contains an atom selected from a carbon atom, an oxygen atom and a nitrogen atom, and
n represents an integer of 1 to 10).

14. The process according to claim 13, wherein the aliphatic carbamic acid ester is such that R8 in the compound represented by the formula (7) is a group selected from the group consisting of an alkyl group having 1 to 20 carbon atoms and a cycloalkyl group having 5 to 20 carbon atoms.

15. The process according to claim 14, wherein the aliphatic carbamic acid ester is at least one compound selected from the group consisting of compounds represented by the following formulas (8), (9) and (10):

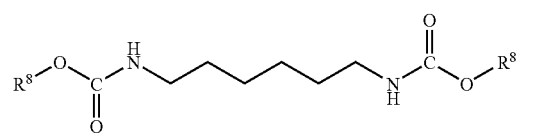
(8)

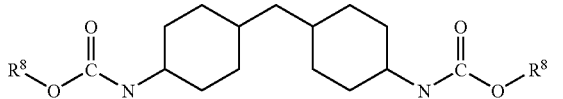
(9)

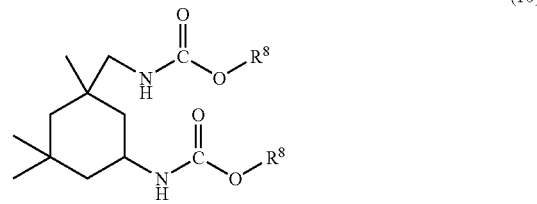
(10)

(wherein R8 is the same as defined above).

16. The process according to claim 15, wherein the aromatic hydroxy compound is selected from a group consisting of 2,4-di-tert-amylphenol; 2,4-di-tert-butylphenol; 2,6-dimethylphenol; 2-phenylphenol; and 2,4-bis(α,α-dimethylbenzyl)phenol.

* * * * *